(12) United States Patent
Ildefonso et al.

(10) Patent No.: US 11,053,291 B2
(45) Date of Patent: Jul. 6, 2021

(54) DELIVERY OF NRF2 AS THERAPY FOR PROTECTION AGAINST REACTIVE OXYGEN SPECIES

(71) Applicant: University of Florida Research Foundation, Inc., Gainesville, FL (US)

(72) Inventors: Cristhian J. Ildefonso, Gainesville, FL (US); Alfred S. Lewin, Gainesville, FL (US); Qiuhong Li, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/120,318

(22) PCT Filed: Feb. 19, 2015

(86) PCT No.: PCT/US2015/016638
§ 371 (c)(1),
(2) Date: Aug. 19, 2016

(87) PCT Pub. No.: WO2015/127094
PCT Pub. Date: Aug. 27, 2015

(65) Prior Publication Data
US 2017/0088593 A1 Mar. 30, 2017

Related U.S. Application Data

(60) Provisional application No. 61/941,885, filed on Feb. 19, 2014.

(51) Int. Cl.
| | | |
|---|---|---|
| *C07K 14/47* | (2006.01) | |
| *A61K 38/17* | (2006.01) | |
| *A61K 9/00* | (2006.01) | |
| *A61K 48/00* | (2006.01) | |

(52) U.S. Cl.
CPC ........ *C07K 14/4702* (2013.01); *A61K 9/0048* (2013.01); *A61K 38/1709* (2013.01); *A61K 48/0075* (2013.01); *C07K 2319/00* (2013.01); *C07K 2319/02* (2013.01); *C07K 2319/10* (2013.01); *C07K 2319/50* (2013.01)

(58) Field of Classification Search
None
See application file for complete search history.

(56) References Cited

U.S. PATENT DOCUMENTS

| | | |
|---|---|---|
| 5,643,758 A | 7/1997 | Guan et al. |
| 6,451,594 B1 | 9/2002 | Chien et al. |
| 7,071,172 B2 | 7/2006 | McCown et al. |
| 7,306,944 B2 | 12/2007 | Choi et al. |
| 8,962,567 B2 | 2/2015 | Choi et al. |
| 2003/0045498 A1 | 3/2003 | Kovesdi et al. |
| 2003/0236396 A1 | 12/2003 | Fasel et al. |
| 2004/0063635 A1 | 4/2004 | Yu et al. |
| 2005/0142130 A1 | 6/2005 | Roks et al. |
| 2007/0031410 A1 | 2/2007 | Harton et al. |
| 2009/0239259 A1 | 9/2009 | Hsieh |
| 2010/0029012 A1 | 2/2010 | Kern et al. |
| 2010/0120665 A1 | 5/2010 | Kaleko et al. |
| 2010/0209447 A1 | 8/2010 | Kumar-Singh et al. |
| 2012/0157513 A1 | 6/2012 | Li et al. |
| 2016/0376325 A1 | 12/2016 | McFadden et al. |

FOREIGN PATENT DOCUMENTS

| | | | |
|---|---|---|---|
| WO | WO 02/26780 A2 | 4/2002 | |
| WO | WO 2007/014162 A2 | 2/2007 | |
| WO | WO 2008/000445 A1 | 1/2008 | |
| WO | WO 2008/057434 A2 | 5/2008 | |
| WO | WO-2010138555 A2 * | 12/2010 | .............. C07K 7/14 |
| WO | WO 2013/012806 A2 | 1/2013 | |
| WO | WO 2013/067036 A1 | 5/2013 | |
| WO | WO 2013/090318 A1 | 6/2013 | |
| WO | WO 2014/005219 A1 | 1/2014 | |
| WO | WO 2014/076702 A1 | 5/2014 | |

OTHER PUBLICATIONS

Steel et al.,"Anti-inflammatory Effect of a Cell-Penetrating Peptide Targeting the Nrf2/Keap1 Interaction", ACS Med. Chem. Lett., 2012, pp. 407-410.*
Kanninen et al., Intrahippocampal injection of a lentiviral vector expression Nrf2 improves spatial learning in a mouse model of Alzheimer's disease, PNSA, 2009, 16505-16510 (Year: 2009).*
Chumanov et al., Expression, purification, and refolding of active Nrf2 transcription factor fused to protein transduction TAT tag, Protein Expression and Purification, 2010, 280-288 (Year: 2010).*
Lee et al., NF-E2-related Factor-2 Mediates Neuroprotection against Mitochondrial Complex I Inhibitors and Increased Concentrations of Intracellular Calcium in Primary Cortical Neurons, The Journal of Biological Chemistry, 2003, p. 37948-37956 (Year: 2003).*
Daya et al., Gene Therapy Using Adeno-Associated Virus Vectors, Clinical Microbiology reviews, 2008, p. 583-593 (Year: 2008).*
Foti et al., Delivering multiple gene products in the brain from a single adeno-associated virus vector, Gene Therapy, 2009, p. 1314-1319 (Year: 2009).*
Waehler et al., Engineering targeted viral vectors for gene therapy, Nature Reviews—Genetics, 2007, p. 573-587 (Year: 2007).*

(Continued)

*Primary Examiner* — Lianko G Garyu
(74) *Attorney, Agent, or Firm* — Wolf, Greenfield & Sacks, P.C.

(57) ABSTRACT

The present invention provides methods and compositions for treating and/or preventing age related macular degeneration and other conditions involving macular degeneration, ocular neovascularization, or inflammation, including ocular inflammation. In some embodiments, the methods comprise administering an expression vector that delivers a secretable and cell penetrating Nrf2 to a subject in need thereof.

13 Claims, 25 Drawing Sheets
Specification includes a Sequence Listing.

(56) References Cited

OTHER PUBLICATIONS

Zhao et al. "A novel strategy to activate cytoprotective genes in the injured brain", Biochemical and Biophysical Research Communications, 2011, pp. 501-506 (Year: 2011).*
Déglon et al. "Self-Inactivating Lentiviral Vectors with Enhanced Transgene Expression as Potential Gene Transfer System in Parkinson's Disease", Human Gene Therapy, 2000, pp. 179-190 (Year: 2000).*
Naso et al., "Adeno-Associated Virus (AAV) as a Vector for Gene Therapy", BioDrugs, 2017, 317-334 (Year: 2017).*
Zhao et al., "Age-Related Retinopathy in NRF2-Deficient Mice", PLOS Ones, 2011, pp. 1-10 (Year: 2011).*
Steel et al., "Anti-inflammatory Effect of a Cell-Penetrating Peptide Targeting the Nrf2/Keap1 Interaction", ACS Med. Chem. Lett., 2012, pp. 407-410 (Year: 2012).*
Daya et al., "Gene Therapy Using Adeno-Associated Virus Vectors", Clinical Microbiology Reviews, 2008, pp. 583-593 (Year: 2008).*
Petrs-Silva et al., "High-efficiency Transduction of the Mouse Retina by Tyrosine-mutant AAV Serotype Vectors", Molecular Therapy, 2009, pp. 463-471 (Year: 2009).*
Petrs-Silva et al., "Novel Properties of Tyrosine-mutant AAV2 Vectors in the Mouse Retina", Molecular Therapy, 2011, pp. 293-301 (Year: 2011).*
Kay et al., "Targeting Photoreceptors via Intravitreal Delivery Using Novel, Capsid-Mutated AAV Vectors" PLOS One, 2013 1-12 (Year: 2013).*
International Search Report and Written Opinion for International Application No. PCT/US2015/016638 dated May 18, 2015.
International Preliminary Report on Patentability for International Application No. PCT/US2015/016638 dated Sep. 1, 2016.
Chumanov et al., Expression, purification, and refolding of active Nrf2 transcription factor fused to protein transduction TAT tag. Protein Expr Purif. Dec. 2010;74(2):280-8. doi: 10.1016/j.pep.2010.06.017. Epub Jul. 1, 2010.
Steel et al., Anti-inflammatory Effect of a Cell-Penetrating Peptide Targeting the Nrf2/Keap1 Interaction. ACS Med Chem Lett. May 10, 2012;3(5):407-410. Epub Mar. 12, 2012.
Extended European Search Report for Application No. EP 15752059.4 dated Jul. 7, 2017.
Abed et al., Discovery of direct inhibitors of Keap1-Nrf2 protein-protein interaction as potential therapeutic and preventive agents. Acta Pharm Sin B. Jul. 2015;5(4):285-99. doi: 10.1016/j.apsb.2015.05.008. Epub Jul. 2, 2015. Review.
Alhakamy et al., Noncovalently associated cell-penetrating peptides for gene delivery applications. Ther Deliv. Jun. 2013;4(6):741-57. doi: 10.4155/tde.13.44. Review.
Handa et al., How does the macula protect itself from oxidative stress? Mol Aspects Med. Aug. 2012;33(4):418-35. doi: 10.1016/j.mam.2012.03.006. Epub Apr. 5, 2012. Author manuscript.
Ildefonso et al., Targeting the Nrf2 Signaling Pathway in the Retina With a Gene-Delivered Secretable and Cell-Penetrating Peptide. Invest Ophthalmol Vis Sci. Feb. 2016;57(2):372-86. doi: 10.1167/iovs.15-17703.
Koren et al., Cell-penetrating peptides: breaking through to the other side. Trends Mol Med. Jul. 2012;18(7):385-93. doi: 10.1016/j.molmed.2012.04.012. Epub Jun. 7, 2012.

Chan et al., IL-2/B7.1 (CD80) fusagene transduction of AML blasts by a self-inactivating lentiviral vector stimulates T cell responses in vitro: a strategy to generate whole cell vaccines for AML. Mol Ther. Jan. 2005;11(1):120-31.
Jacobson et al., Safety of recombinant adeno-associated virus type 2-RPE65 vector delivered by ocular subretinal injection. Mol Ther. Jun. 2006;13(6):1074-84. Epub Apr. 27, 2006.
Johnston et al., A poxvirus-encoded pyrin domain protein interacts with ASC-1 to inhibit host inflammatory and apoptotic responses to infection. Immunity. Dec. 2005;23(6):587-98. Erratum in: Immunity. Oct. 2006;25(4):687. Ricuttio, Dan [corrected to Ricciuto, Dan].
Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.
Le et al., Pyrin- and CARD-only Proteins as Regulators of NLR Functions. Front Immunol. Sep. 17, 2013;4:275. doi: 10.3389/fimmu.2013.00275.
Liu et al., The immunoregulatory properties of oncolytic myxoma virus and their implications in therapeutics. Microbes Infect. Dec. 2010;12(14-15):1144-52. doi: 10.1016/j.micinf.2010.08.012. Epub Sep. 9, 2010. Author manuscript.
Lucas et al., Secreted immunomodulatory viral proteins as novel biotherapeutics. J Immunol. Oct. 15, 2004;173(8):4765-74.
Rahman et al., Co-regulation of NF-kappaB and inflammasome-mediated inflammatory responses by myxoma virus pyrin domain-containing protein M013. PLoS Pathog. Oct. 2009;5(10):e1000635. doi: 10.1371/journal.ppat.1000635. Epub Oct. 23, 2009.
Rahman et al., Myxoma virus lacking the pyrin-like protein M013 is sensed in human myeloid cells by both NLRP3 and multiple Toll-like receptors, which independently activate the inflammasome and NF-κB innate response pathways. J Virol. Dec. 2011;85(23):12505-17. doi: 10.1128/JVI.00410-11. Epub Sep. 28, 2011.
Rahman et al., Myxoma virus protein M029 is a dual function immunomodulator that inhibits PKR and also conscripts RHA/DHX9 to promote expanded host tropism and viral replication. PLoS Pathog. 2013;9(7):e1003465. doi: 10.1371/journal.ppat.1003465. Epub Jul. 4, 2013.
Smith et al., Vaccinia virus immune evasion: mechanisms, virulence and immunogenicity. J Gen Virol. Nov. 2013;94(Pt 11):2367-92. doi: 10.1099/vir.0.055921-0. Epub Sep. 2, 2013.
Stöckli et al., Molecular cloning, expression and regional distribution of rat ciliary neurotrophic factor. Nature. Dec. 21-28, 1989;342(6252):920-3.
Taxman et al., Inflammasome inhibition as a pathogenic stealth mechanism. Cell Host Microbe. Jul. 22, 2010;8(1):7-11. doi: 10.1016/j.chom.2010.06.005.
Giove et al., Transduction of the inner mouse retina using AAVrh8 and AAVrh10 via intravitreal injection. Exp Eye Res. Nov. 2010;91(5):652-9. doi: 10.1016/j.exer.2010.08.011. Epub Aug. 17, 2010. Author manuscript.
Pang et al., Comparative analysis of in vivo and in vitro AAV vector transduction in the neonatal mouse retina: effects of serotype and site of administration. Vision Res. Feb. 2008;48(3):377-85. Epub Oct. 22, 2007.
Chen et al., Distribution, markers, and functions of retinal microglia. Ocul Immunol Inflamm. Mar. 2002;10(1):27-39. doi: 10.1076/ocii.10.1.27.10328.

* cited by examiner

Detection of TatNrf2-14 mer cDNA by PCR

DELIVERY OF NRF2 AS THERAPY FOR PROTECTION AGAINST REACTIVE OXYGEN SPECIES

CROSS-REFERENCE TO RELATED APPLICATIONS

This application is a national stage filing under 35 U.S.C. § 371 of International PCT application PCT/US2015/016638, filed Feb. 19, 2015 which claims the benefit of the filing date of U.S. Provisional Application No. 61/941,885 filed Feb. 19, 2014, the entire contents of which are incorporated by reference herein.

GOVERNMENT FUNDING

The invention was made with government support under R01 EY020825 awarded by the National Institutes of Health. The federal government has certain rights in this invention.

BACKGROUND

Sustained oxidative stress is known to be involved in the pathophysiology of diseases like Diabetic Retinopathy (DR), Amyotrophic Lateral Sclerosis (ALS), and Age-related Macular Degeneration (AMD). The overproduction of reactive oxygen species (ROS) and reactive nitrogen species (RNS) leads to the oxidation or nitration of proteins, lipids and DNA. These changes are deleterious to the cell since they lead to the degradation of modified proteins, accumulation of oxidized lipids and mutations in the DNA sequence. Furthermore, some of these modified molecules can become immunogenic and induce an inflammatory process.

SUMMARY OF THE INVENTION

Aspects of the disclosure relate to polypeptides comprising one or more peptide or protein domains for delivery of an Nrf2 peptide to a cell. In some embodiments, the polypeptide comprises an Nrf2 peptide in combination with one or more of a secretion signal, a carrier protein, and a cell penetrating peptide.

In some aspects, the disclosure provides a method for the prevention, amelioration, or treatment of a disease or condition associated with oxidative stress or inflammation in a subject comprising administration of a therapeutically effective amount of a recombinant polypeptide to a subject, wherein the recombinant polypeptide comprises a cell penetrating peptide and an Nrf2 peptide.

In some embodiments, the recombinant polypeptide comprises a secretion signal, a cell penetrating peptide, and an Nrf2 peptide. In some embodiments, the polypeptide comprises a secretion signal, a carrier protein, a cell penetrating peptide, and an Nrf2 peptide. In some embodiments, the Nrf2 peptide has the amino acid sequence LQLDEETGEFLPIQ (SEQ ID NO: 1). In some embodiments, the secretion signal, if present, is selected from a secretion signal provided in Table 1, the cell penetrating peptide is selected from a cell penetrating peptide provided in Table 2, and the carrier protein, if present, is selected from a carrier protein provided in Table 3. In some embodiments, the carrier protein and cell penetrating peptide are linked to one another by an enzyme cleavage site. In some embodiments, the enzyme cleavage site is a furin cleavage site.

In some embodiments, said administration comprises secretion of the recombinant polypeptide from cells transfected with a vector comprising a nucleotide sequence encoding the recombinant polypeptide. In some embodiments, said inflammation is ocular inflammation. In some embodiments, the vector is administered to cells in the subject via intravitreal injection, subretinal injection, injection into the anterior chamber of the eye, injection or application locally to the cornea, subconjunctival injection, subtenon injection, or eye drops.

In some embodiments, the disease or condition associated with oxidative stress comprises an ocular disease and the recombinant polypeptide reduces secretion of IL-1β. In some embodiments, the disease or condition is selected from the group consisting of macular degeneration, age-related macular degeneration (AMD), geographic atrophy, wet AMD, dry AMD, drusen formation, dry eye, diabetic retinopathy, vitreoretinopathy, corneal inflammation, uveitis, ocular hypertension or glaucoma.

Other aspects of the disclosure relate to a composition comprising a pharmaceutically acceptable carrier and a recombinant polypeptide or viral vector comprising an expression construct comprising a nucleotide sequence encoding the recombinant polypeptide, wherein the recombinant polypeptide comprises a cell penetrating peptide and an Nrf2 peptide.

In some embodiments, the recombinant polypeptide comprises a secretion signal, a cell penetrating peptide, and an Nrf2 peptide. In some embodiments, the polypeptide comprises a secretion signal, a carrier protein, a cell penetrating peptide, and an Nrf2 peptide. In some embodiments, the Nrf2 peptide has the amino acid sequence LQLDEETGEFLPIQ (SEQ ID NO: 1). In some embodiments, the secretion signal, if present, is selected from a secretion signal provided in Table 1, the cell penetrating peptide is selected from a cell penetrating peptide provided in Table 2, and the carrier protein, if present, is selected from a carrier protein provided in Table 3. In some embodiments, the carrier protein and cell penetrating peptide are linked to one another by an enzyme cleavage site. In some embodiments, the enzyme cleavage site is a furin cleavage site.

In some embodiments, the composition is contained in a syringe. In some embodiments, the composition comprises the viral vector and the viral vector is a AAV vector or lentiviral vector.

Other aspects of the disclosure relate to a viral vector comprising an expression construct comprising a nucleotide sequence encoding a recombinant polypeptide, wherein the recombinant polypeptide comprises a cell penetrating peptide and an Nrf2 peptide.

In some embodiments, the recombinant polypeptide comprises a secretion signal, a cell penetrating peptide, and an Nrf2 peptide. In some embodiments, the polypeptide comprises a secretion signal, a carrier protein, a cell penetrating peptide, and an Nrf2 peptide. In some embodiments, the Nrf2 peptide has the amino acid sequence LQLDEETGEFLPIQ (SEQ ID NO: 1). In some embodiments, the secretion signal, if present, is selected from a secretion signal provided in Table 1, the cell penetrating peptide is selected from a cell penetrating peptide provided in Table 2, and the carrier protein, if present, is selected from a carrier protein provided in Table 3. In some embodiments, the carrier protein and cell penetrating peptide are linked to one another by an enzyme cleavage site. In some embodiments, the enzyme cleavage site is a furin cleavage site. In some embodiments, said viral vector is an AAV vector or lentiviral vector.

Yet other aspects of the disclosure relate to a cell engineered to express a recombinant polypeptide, wherein the recombinant polypeptide comprises a cell penetrating peptide and an Nrf2 peptide. In some embodiments, the recombinant polypeptide is a recombinant polypeptide as described in any one of the embodiments above or provided herein. In some embodiments, the cell is transfected with a viral vector of any one of the embodiments above or provided herein.

Other aspects of the disclosure relate to an ocular device loaded with a viral vector of any one of the embodiments above or provided herein.

DESCRIPTION OF DRAWINGS

FIG. 21A. Plasmid containing the TatNrf2mer sequence. FIG. 21B. Detection of TatNrf2mer mRNA in stably transfected ARPE-19 cells expressing TatNrf2mer. FIG. 21C. ARPE-19 stably expressing TatNrf2mer had greater expression of ARE genes. FIG. 21D. TatNrf2mer expression protects ARPE-19 cells from H2O2 induced oxidative stress. In FIGS. 21C and D, the bars are grouped from left to right as, untransfected, vector, TatNrf2mer.

FIG. 23A. A diagram of two lentiviral vectors delivering a secretable GFP (sGFP) or a sGFP fused to the TatNrf2mer by a furin cleavage site (FCS) were designed. FIG. 23B. Photographs of distribution of GFP and sGFP-TatNrf2mer in stable HEK293T cells. FIG. 23C. A graph showing that the conditioned media from sGFP-TatNrf2mer increased the expression of two ARE genes in ARPE-19 cells.

FIGS. 24A-B. Mice injected with the sGFP-TatNrf2mer had higher levels of two antioxidant genes (HO-1 and GSTM1) when compared to GFP injected control eyes. FIGS. 24C-D. After sodium iodate injury, eyes injected with the sGFP-TatNrf2mer had partial protection of the ERG a- and b-wave when compared to GFP injected eyes.

FIG. 25A is a graph that shows ARPE-19 stably expressing puroR (Vector) or TatNrf2mer-puroR (TatNrf2mer) incubated with or without 30 μM of 4-hydroxynonenal (4-HNE) for 18 hours. The concentration of interleukin 1β (IL-1β) in their conditioned media was quantified by ELISA. FIG. 25B is a series of photographs showing eyes of C57BL/6J mice injected intravitreally with 3×10^9 vgc of AAV vector delivering either GFP or sGFP-TatNrf2mer (TatNrf2mer). Three weeks later, gene expression was determined by fluorescence fundoscopy using a micron III camera. Eyes injected with the GFP vector showed a fluorescence signaling that correlates with the retina ganglionic cell layer, however the eyes injected with the TatNrf2mer showed a diffused GFP fluorescence thus suggesting the secretion of the transgene. This diffuse pattern is not due to autofluorescence since non-injected animals showed no fluorescent signal when subjected to the same exposure times (No injection). FIG. 25C is a photograph and a graph showing eye data from mice were injected intravitreally with 25 ng of LPS one week after fundus evaluation and were euthanized 24 hours later. Their eyes were harvested and analyzed by histology. Representative images of H&E stained sections of eyes injected with either GFP or TatNrf2mer vectors are shown (FIG. 25C, left). The number of cells within the vitreous of at least two sections per eye were quantified by two independent subjects who were not aware of the treatments (FIG. 25C, right). Eyes injected with the TatNrf2mer AAV vector had significantly lower numbers of infiltrating cells within the vitreous body than the eyes injected with the GFP AAV vector.

DETAILED DESCRIPTION

Figure 1:
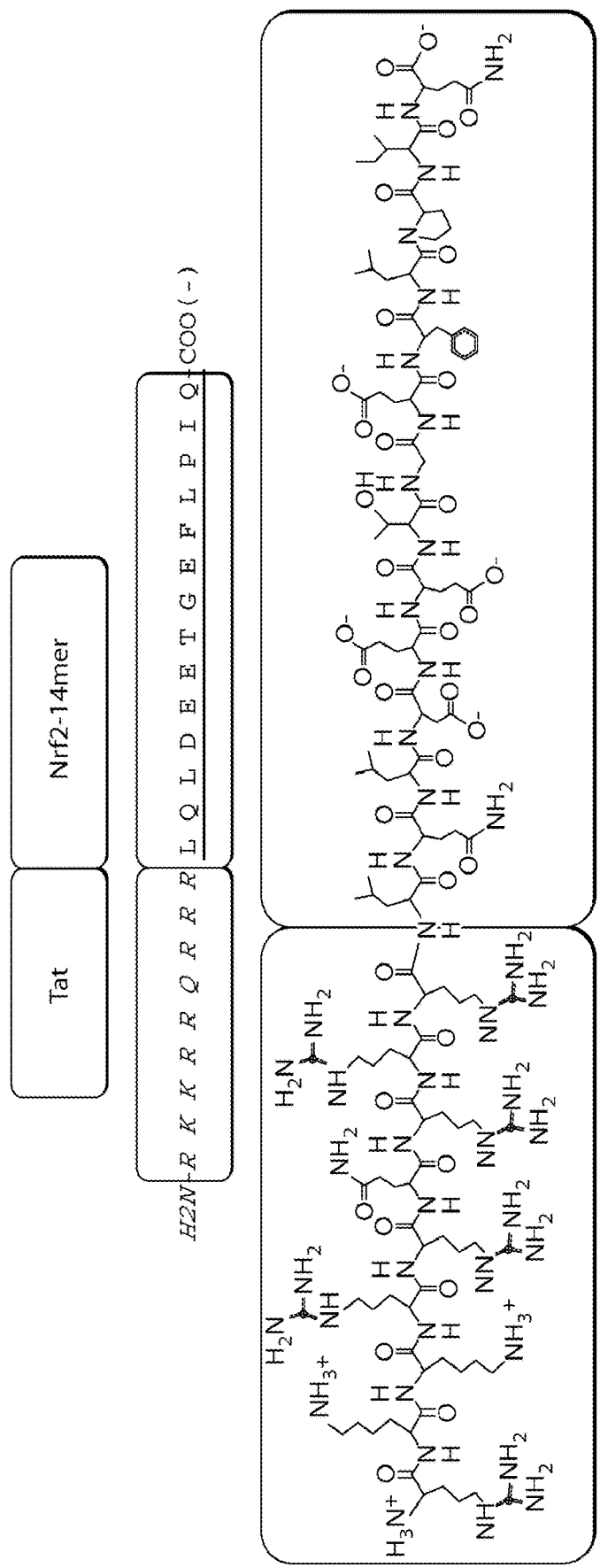
FIG. 1 is a diagram that shows an exemplary TatNrf2-14mer. The Tat peptide is derived from HIV-1 and is used to transport the Nrf2 peptide (14mer) into cells. The sequence corresponds to SEQ ID NO: 131.

The Nrf2-Keap-1 signaling pathway is known to regulate the expression of detoxifying enzymes. In turn these enzymes degrade ROS therefore decreasing the oxidative stress within the cell. Embodiments of this disclosure involve an adeno-associated viral (AAV) vector that delivers a secretable and cell penetrating Nrf2-14 mer peptide that inhibits the interaction of Nrf2 with its inhibitor Keap-1. This Nrf2-14 mer peptide mimics the Keap-1 binding region of Nrf2 and binds with high affinity to the repressor Keap-1. The liberated transcription factor Nrf2 then translocates to the nucleus and induces the expression of the detoxifying enzymes regulated by the antioxidant response element (ARE) sequence. Using molecular techniques, the Nrf2-14 mer peptide was fused at its amino terminus to the HW-1 Tat protein cell penetrating sequence and to a secretable GFP trough a furin cleavage site. In cell culture experiments, it has been demonstrated that expression of the TatNrf2-14 mer peptide leads to an increase in the ARE controlled GSTM1 mRNA levels.

Also, in a cell culture model of oxidative stress these cells have shown increase viability when exposed to H2O2 when compared to control cells. Also measured were the levels of nitrotyrosine (a RNS modification of proteins associated with increase oxidative stress) and found that cells expressing the TatNrf2-14 mer peptide have lower levels of nitrotyrosine equivalents when compared to control cells upon H2O2 incubation. The data provided herein indicates that this AAV vector may serve as a treatment for diseases or conditions caused by oxidative stress, or more generally inflammation, like dry Age-related Macular Degeneration (AMD), Diabetic Retinopathy (DR), Amyotrophic Lateral Sclerosis (ALS), Arthritis, Uveitis (e.g., autoimmune or recurrent uveitis), Vasculitis, Behçet's Disease, Lupus erythematosus, and Nephritis.

Additionally, the TatNrf2-14 mer peptide was shown to be effective in vivo. The secretable form of the TatNrf2-14 mer peptide was shown to be expressed outside of vector transduced cells, demonstrating that the peptide could be secreted and targeted to neighboring cells not expressing the peptide.

Accordingly, aspects of the disclosure relate to methods and compositions for delivery of secreted recombinant polypeptides (e.g., recombinant polypeptides comprising a Nrf2 peptide as described herein) from cells transduced with a nucleic acid vector that encodes the recombinant polypeptide to adjacent non-transduced cells, thereby achieving delivery of the polypeptides to a population of cells, even if only a subset of the population expresses the recombinant polypeptides.

Definitions

"Biocompatible" refers to a material that is substantially non-toxic to cells in vitro, e.g., if its addition to cells in culture results in less than or equal to 20% cell death. A material is considered biocompatible with respect to a recipient if it is substantially nontoxic to the recipient's cells in the quantities and at the location used, and also does not elicit or cause a significant deleterious or untoward effect on the recipient's body, e.g., an immunological or inflammatory reaction, unacceptable scar tissue formation, etc.

"Biodegradable" means that a material is capable of being broken down physically and/or chemically within cells or within the body of a subject, e.g., by hydrolysis under physiological conditions, by natural biological processes such as the action of enzymes present within cells or within the body, etc., to form smaller chemical species which can be metabolized and, optionally, reused, and/or excreted or otherwise disposed of. In some embodiments, a biodegradable compound is biocompatible.

"Concurrent administration" as used herein with respect to two or more agents, e.g., therapeutic agents, is administration performed using doses and time intervals such that the administered agents are present together within the body, or at a site of action in the body such as within the eye) over a time interval in less than de minimis quantities, i.e., in quantities sufficient to have a detectable biological effect or response. The time interval can be minutes, hours, days, weeks, etc. Accordingly, the agents may, but need not be, administered together as part of a single composition. In addition, the agents may, but need not be, administered simultaneously (e.g., within less than 5 minutes, or within less than 1 minute) or within a short time of one another (e.g., less than 1 hour, less than 30 minutes, less than 10 minutes, approximately 5 minutes apart). According to various embodiments of the disclosure agents administered within such time intervals may be considered to be administered at substantially the same time. One of ordinary skill in the art will be able to readily determine appropriate doses and time interval between administration of the agents so that they will each be present at more than de minimis levels within the body or at effective concentrations within the body. When administered concurrently, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

An "effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, an effective amount may be an amount sufficient to achieve one or more of the following: (i) prevent drusen formation; (ii) cause a reduction in drusen number and/or size (drusen regression); (iii) cause a reduction in or prevent lipofuscin deposits; (iv) prevent visual loss or slow the rate of visual loss; (v) prevent or slow the rate of choroidal neovascularization; (vi) cause a reduction in size and/or number of lesions characterized by choroidal neovascularization; (vii) improve visual acuity and/or contrast sensitivity; (viii) prevent or reduce the rate of photoreceptor or RPE (retina pigmented epithelium) cell atrophy or apoptosis; (ix) prevent or slow progression from the wet to the dry form of AMD.

"Local administration" or "local delivery", in reference to delivery of a composition, formulation, or device of the disclosure, refers to delivery that does not rely upon transport of the agent to its intended target tissue via the vascular or lymphatic system from a site of administration that is remote from the intended target tissue. The agent is delivered directly to its intended target tissue or in the vicinity thereof, e.g. by injection or implantation. It will be appreciated that a small amount of the delivered agent may enter the vascular system and may ultimately reach the target tissue via the vascular system.

"Macular degeneration related condition" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and capillary endothelial cells. AMD is the major macular degeneration related condition, but a number of others are known including, but not limited to, Best macular dystrophy, Sorsby fundus dystrophy, Mallatia Leventinese and Doyne honeycomb retinal dystrophy. Subjects with AMD and other macular degeneration related conditions may be identified by the skilled practitioner, e.g., using methods known in the art including a visual acuity test, pupil dilation, ophthalmoscopy or fundus photography, fundus fluorescein angiography (FFA), and optical coherence tomography (OCT).

"Ocular device" refers to a drug delivery device that has appropriate structure, dimensions, shape, and/or configuration and is made of appropriate materials so that it may be placed in or on the surface of the eye without causing unacceptable interference with the physiology or functioning of the eye. In some embodiments, placement of an ocular device does not significantly disrupt vision. An ocular device is typically a solid or semi-solid article of manufacture and is typically macroscopic, i.e., visible with the naked eye.

"Ocular neovascularization" (ONV) is used herein to refer to choroidal neovascularization or retinal neovascularization, or both.

"Polypeptide", as used herein, refers to a polymer of amino acids and/or amino acid analogs which may or may not be modified. Various amino acid analogs and modifications are described herein. A polypeptide may be cyclic or linear and may be branched or unbranched. The term "amino acid sequence" or "polypeptide sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. For purposes of the disclosure the use of the term "polypeptide" and "protein" are interchangeable unless specifically noted otherwise.

"Purified", as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular polypeptides and/or nucleic acids.

"Retinal neovascularization" (RNV) refers to the abnormal development, proliferation, and/or growth of retinal blood vessels, e.g., on the retinal surface.

"Sequential administration" of two or more agents refers to administration of two or more agents to a subject such that the agents are not present together in the subject's body at greater than de minimis concentrations. Administration of the agents may, but need not, alternate. Each agent may be administered multiple times.

"Subject", as used herein, refers to an individual to whom an agent is to be delivered, e.g., for experimental, diagnostic, and/or therapeutic purposes. In some embodiments, subjects are mammals, particularly domesticated mammals (e.g., dogs, cats, etc.), primates, or humans.

"Significant sequence homology" as applied to an amino acid sequence means that the sequence displays at least approximately 20% identical or conservatively replaced amino acids, preferably at least approximately 30%, at least approximately 40%, at least approximately 50%, at least approximately 60% identical or conservatively replaced amino acids, desirably at least approximately 70% identical or conservatively replaced amino acids, more desirably at least approximately 80% identical or conservatively replaced amino acids, and most desirably at least approximately 90% amino acid identical or conservatively replaced amino acids relative to a reference sequence. When two or more sequences are compared, any of them may be considered the reference sequence. % identity can be calculated using a FASTA or BLASTP algorithm, using default parameters. A PAM250 or BLOSUM62 matrix may be used. For purposes of calculating % identical or conservatively replaced residues, a conservatively replaced residue is considered identical to the residue it replaces. Conservative replacements may be defined in accordance with Stryer, L, Biochemistry, 3rd ed., 1988, according to which amino acids in the following groups possess similar features with respect to side chain properties such as charge, hydrophobicity, aromaticity, etc. (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; (7) Cyclic aliphatic side chain: P. Other exemplary conservative replacements include Ala to Gly or Ser; Arg to Lys; Asn to Gln or His; Cys to Ser; Gln to Asn; Glu to Asp; Gly to Ala or Pro; His to Asn or Gln; Ile to Leu or Val; Leu to Ile or Val; Lys to Arg, Gln, or Glu; Met to Leu, Tyr, or Ile; Phe to Met, Leu, or Tyr; Ser to Thr; Thr to Ser; Trp to Tyr; Tyr to Trp or Phe; or Val to Ile or Leu.

"Substantial sequence homology" as applied to a sequence means that the sequence displays at least approximately 60% identity, desirably at least approximately 70% identity, more desirably at least approximately 80% identity, and most desirably at least approximately 90% identity relative to a reference sequence. When two or more sequences are compared, any of them may be considered the reference sequence. % identity can be calculated using a FASTA, BLASTN, or BLASTP algorithm, depending on whether amino acid or nucleotide sequences are being compared. Default parameters may be used. A PAM250 or BLOSUM62 matrix may be used.

A "sustained release formulation" is a composition of matter that comprises a therapeutic agent as one of its components and further comprises one or more additional components, elements, or structures effective to provide sustained release of the therapeutic agent, optionally in part as a consequence of the physical structure of the formulation. Sustained release is release or delivery that occurs either continuously or intermittently over a period of time e.g., at least 1, 2, 4, or 6 weeks, at least 1, 2, 3, 4, 6, 8, 10, 12, 15, 18, or 24 months, or longer.

"Treating" or "treatment of" as used herein, refers to providing any type of medical or surgical management to a subject. Treating can include, but is not limited to, administering a composition comprising a therapeutic agent to a subject. "Treating" includes any administration or application of a compound or composition of the disclosure to a subject for purposes such as curing, reversing, alleviating, reducing the severity of, inhibiting the progression of, or reducing the likelihood of a disease, disorder, or condition or one or more symptoms or manifestations of a disease, disorder or condition. A composition of this disclosure can be administered to a subject who has developed a macular degeneration related condition risk of developing an infection relative to a member of the general population. A composition of this disclosure can be administered to a subject who has developed an eye disorder such as exudative or non-exudative AMD or diabetic retinopathy or is at increased risk of developing such a disorder relative to a member of the general population. A composition of this disclosure can be administered to a subject who has developed or is at increased risk of developing a disease or condition characterized by or involving inflammation, such as dry AMD, diabetic retinopathy (DR), ALS, Arthritis, Uveitis (e.g., autoimmune or recurrent uveitis), Vasculitis, Behçet's Disease, Lupus erythematosus, or Nephritis. A composition of this disclosure can be administered prophylactically, i.e., before development of any symptom or manifestation of the condition. Typically in this case the subject will be at risk of developing the condition.

A variety of factors including oxidative stress, inflammation with a possible autoimmune component, genetic background (e.g., mutations), and environmental or behavioral features such as smoking and diet may contribute to the pathogenesis of AMD in manners that are as yet poorly understood (Zarbin, M A, Arch Opthalmol. 122:598-614, 2004). Regardless of the underlying etiology, the clinical hallmark of AMD is the appearance of drusen, localized deposits of lipoproteinaceous material that accumulate in the space between the RPE and Bruch's membrane, which separates the RPE from the choroidal vessels (choriocapillaris). Drusen are typically the earliest clinical finding in AMD. The existence of macular drusen is a strong risk factor for the development of both wet and dry forms of AMD (Ambati, J., et al., Surv. Opthalmol., 48(3): 257-293, 2003).

Ocular inflammation can affect a large number of eye structures including the conjunctiva, cornea, episclera, sclera, uveal tract, retina, vasculature, optic nerve, and orbit. Evidence of ocular inflammation can include the presence of inflammation-associated cells such as white blood cells (e.g., neutrophils, macrophages) in the eye, the presence of endogenous inflammatory mediators known in the art, one or more symptoms such as eye pain, redness, light sensitivity, blurred vision and floaters, etc. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. Uveitis can arise from a number of different causes and is associated with a number of different diseases, including, but not limited to, rheumatic diseases such as rheumatic diseases (e.g., ankylosing spondylitis and juvenile rheumatoid arthritis), certain infectious diseases such as tuberculosis and syphilis, other conditions such as sarcoidosis, systemic lupus erythematosus, chemical injury, trauma, surgery, etc. Keratis refers to inflammation of the cornea. Keratitis has a diverse array of causes including bacterial, viral, or fungal infection, trauma, and allergic reaction. Amoebic infection of the cornea, e.g., caused by *Acanthamoeba*, is a particular problem for contact lens wearers. Scleritis refers to inflammation of the sclera. Uveitis, keratitis, and scleritis, and methods for their diagnosis are well known in the art. Symptoms of the various inflammatory conditions that affect the eye can include, but are not limited to, eye pain, redness, light sensitivity, tearing, blurred vision, floaters. Ocular inflammation of various types is well known to occur in association with a variety of local or systemic diseases, some of which are noted above. In some instances the cause may remain unknown.

Diabetic retinopathy (DR) is a retinopathy that is a complication of diabetes. DR is caused by inflammation, intramural pericyte death and thickening of the basement membrane induced by hyperglycemia, which leads to weakening of the vascular walls and permeabilization of retinal blood vessels. DR may progress to proliferative DR, where blood vessels begin to proliferate, leading to bleeding, cloudy vision, and retinal detachment. Subjects with DR may be identified by the skilled practitioner, e.g., using methods known in the art including a visual acuity test, pupil dilation, ophthalmoscopy or fundus photography, fundus fluorescein angiography (FFA), and optical coherence tomography (OCT).

Amyotrophic lateral sclerosis (ALS) is a neurodegenerative disorder characterized by stiffness, muscle twitching, and progressive weakness due to neuronal death and muscle wasting. This results in problems with speaking, swallowing, and eventually breathing, leading to death. Inflammation is thought to play a role in ALS progression, e.g., by recruiting macrophages that destroy healthy neurons. Subjects with ALS may be identified by the skilled practitioner, e.g., using methods known in the art including signs and symptoms, electromyography, nerve conduction velocity, magnetic resonance imaging, or muscle biopsy.

Arthritis is a joint disorder that involves inflammation of one or more joint. The main symptom is pain in the affected joints. Swelling and stiffness of the joint is also common. Exemplary forms of arthritis include osteoarthritis, rheumatoid arthritis, and psoriatic arthritis. Subjects with arthritis may be identified by the skilled practitioner, e.g., using methods known in the art including x-rays and blood tests for biomarkers such as rheumatoid factor, antinuclear factor (ANF), and extractable nuclear antigen.

Autoimmune Uveitis: Uveitis is a complex group of sight threatening diseases that can result from infection, systemic inflammation, or an autoimmune response. Uveitis is estimated to cause 10-15% of all cases of blindness in United States. Histological analysis shows disorganized retinal architecture, damage to ganglion and photoreceptor cell layers, retinal folds, subretinal exudate, vasculitis, damage to retinal pigment epithelium, and choroiditis. Left untreated, it can lead to complications such as cystoid macular edema, cataract, secondary glaucoma, vitreous opacities, and retinal scars. Autoimmune uveitis can also be a part of a systemic autoimmune response involving multiple organs. There are many conditions that can be the cause of uveitis secondarily, including sarcoidosis, Behcet's disease, and Vogt-Koyanagi-Harada (VKH) syndrome. Autoimmune disorders such as rheumatoid arthritis and Crohn's disease can also have an overlapping uveitis. After the initial trigger, the immunogenic pathways in these different disease states share many common features. Thus, it is conceivable that treatments developed against uveitis will also provide benefits in these overlapping disorders. The current treatments for non-infectious uveitis include corticosteroids, general immunosuppressants, or specific antibodies. Although initial inflammation is suppressed, continued treatment with corticosteroids is associated with development of cataracts, glaucoma, retinopathy, and activation of herpes simplex virus. Immunosuppressant agents, such as Cyclosporine A (CsA), a T cell targeting drug that blocks IL-2 signaling has been used for ocular inflammation. FK-506 (tacrolimus) and rapamycin, which also target IL-2 signaling have been used. This line of treatment is discouraged, because of the involvement of IL-2 in maintenance of regulatory T cells (Tregs), and decreased levels of Tregs are undesirable. Furthermore, these treatments are not advised for a prolonged treatment. Antibodies targeting tumor necrosis factor α (TNF-α) or IL-1 that can suppress inflammatory signaling pathways are being currently tested. Because of the adverse side effects observed with these treatments, it is important to develop novel therapeutics that target the basic disease mechanisms in uveitis.

Vasculitis is a condition characterized by inflammation of blood vessels. There are several types of vasculitis as well as disorders that cause vasculitis including mostly large vessel vasculitis, Behçet's Disease, Cogan's Syndrome, Giant Cell Arteritis, Polymyalgia Rheumatica, Takayasu's Arteritis, mostly medium vessel vasculitis, Buerger's Disease, Central Nervous System vasculitis, Kawasaki Disease, Polyarteritis Nodosa, mostly small vessel vasculitis, Eosinophilic Granulomatosis with Polyangiitis, Cryoglobulinemia Vasculitis, IgA Vasculitis, Hypersensitivity Vasculitis, and Microscopic Polyangiitis. Subjects having vasculitis may be identified by the skilled practitioner, e.g., using methods known in the art including blood tests (e.g., hemoglobin and hematocrit, antineutrophil cytoplasmic antibodies, Erythrocyte sedimentation rate, and C-reactive protein (CRP) levels), biopsy, blood pressure test, urinalysis (e.g., to detect protein or blood cells), EKG (Electrocardiogram), Echocardiography, x-ray, Computed Tomography scan, Magnetic Resonance Imaging, Angiography, and positron emission tomography.

Behçet's Disease is an immune-mediated small-vessel systemic vasculitis. Behçet's may cause anterior uveitis (inflammation in the front of the eye) or posterior uveitis (inflammation in the back of the eye), as well as ulcers of the mouth, skin and/or genital lesions, joint swelling, CNS inflammation and abdominal pain. Subjects having Behçet's Disease may be identified by the skilled practitioner, e.g., using methods known in the art including the presence of mouth sores at least three times in 12 months along with at least two of genital sores, eye inflammation, sores on the skin, and a positive skin prick test.

Lupus erythematosus is an autoimmune disease characterized by attack of healthy tissue by the subject's own immune system. Lupus erythematosus is characterized into four main types: systemic (SLE), discoid, drug-induced and neonatal. SLE can affect the skin, joints, kidneys, brain, and other organs. Common symptoms include joint pain, swelling, and arthritis. Other symptoms include chest pain, fatigue, fever, hair loss, mouth sores, rashes, and swollen lymph nodes. Subjects having lupus erythematosus may be identified by the skilled practitioner, e.g., using methods known in the art including complete blood count, erythrocyte sedimentation rate, kidney and liver assessment. urinalysis (e.g., to detect protein or blood cells), antinuclear antibody (ANA) assay, x-ray, echocardiogram, and biopsy.

Nephritis is a form of inflammation of the kidneys that may involve the glomeruli, tubules, or interstitial tissue surrounding the glomeruli and tubule. There are several types of nephritis including glomerulonephritis (inflammation of the glomeruli), interstitial nephritis or tubulo-interstitial nephritis (inflammation of the spaces between renal tubules), Pyelonephritis (inflammation that results from a urinary tract infection), Lupus nephritis (inflammation caused by SLE), and Athletic nephritis (inflammation caused by strenuous exercise). Subjects having nephritis may be identified by the skilled practitioner, e.g., using methods known in the art including complete blood count (CBC), blood urea nitrogen (BUN), blood creatinine, blood gases (level of oxygen and carbon dioxide in the blood), urinalysis, kidney ultrasound, and kidney biopsy.

DESCRIPTION OF EXEMPLARY EMBODIMENTS

In some embodiments, a recombinant polypeptide is provided comprising a cell penetrating peptide and an Nrf2 peptide. In some embodiments, the polypeptide comprises a secretion signal, a cell penetrating peptide, and an Nrf2 peptide (e.g., from N- to C-terminus, respectively). In some embodiments, the recombinant polypeptide comprises a secretion signal, a carrier protein, a cell penetrating peptide, and an Nrf2 peptide (e.g., from N- to C-terminus, respectively). In some embodiments, the secretion signal, cell penetrating peptide, Nrf2 peptide and/or carrier protein are connected without any spacers. In some embodiments, the secretion signal, cell penetrating peptide, Nrf2 peptide and/or carrier protein are linked to one another by one or more spacers, e.g., one or more amino acids. In some embodiments, the spacer comprises an enzyme cleavage site, such as a furin cleavage site, e.g., between the carrier protein and the cell penetrating peptide. Exemplary enzymes with cleavage sites appropriate for a spacer are provided in Table 4. In some embodiments, the polypeptide has the below exemplary, non-limiting structure:
N-terminus—Secretion signal—Carrier protein—(Optional enzyme cleavage site)—Cell penetrating peptide—Nrf2 peptide—C-terminus It is to be understood that the recombinant polypeptide is not a full-length Nrf2 protein.

In some embodiments, a secretion signal is a peptide that enhances secretion of a polypeptide containing the signal from a cell compared to a polypeptide lacking the secretion signal. Secretion of a polypeptide from a cell can be detected using any method known in the art or described herein, e.g., by ELISA, mass spectrometry, Western blot, and other similar assays performed on a supernatant of the cell. In some embodiments, the cell is a ARPE-19 cell or HEK293T cell. In some embodiments, the secretion signal comprises or consists of a sequence in Table 1, or a fragment or variant thereof that is capable of enhancing secretion of the polypeptide (e.g., compared to a polypeptide not containing the secretion signal). In some embodiments, the cell penetrating peptide comprises or consists of the amino acid sequence METDTLLLWVLLLWVPGSTG (SEQ ID NO: 2), or a fragment or variant thereof that is capable of enhancing secretion of the polypeptide (e.g., compared to a polypeptide not containing the secretion signal). In some embodiments, the fragment has one, two or three amino acid deletions from the N and/or C terminus of an amino acid sequence provided in Table 1. In some embodiments, the variant has one, two or three amino acid substitutions (e.g., conservative amino acid substitutions) in an amino acid sequence provided in Table 1. In some embodiments, the signal sequence is no more than 50, no more than 40, no more than 30, no more than 25, or no more than 20 amino acids in length. In some embodiments, the signal sequence is between 5 and 50, 10 and 50, 5 and 40, 10 and 40, 5 and 30, 10 and 30, 5 and 25, 10 and 25, 5 and 10 or 10 and 10 amino acids in length.

In some embodiments, a cell penetrating peptide is a peptide that enhances penetration of a polypeptide containing the peptide into a cell compared to a polypeptide lacking the cell penetrating peptide. Penetration of a polypeptide into a cell can be detected using any method known in the art or described herein, e.g., Western blot, immunohistochemistry, immunofluorescence, and other similar assays performed, e.g., on a fixed cell or on a cell lysate. In some embodiments, the cell is a ARPE-19 cell or HEK293T cell. In some embodiments, the cell penetrating peptide comprises an amino acid sequence that includes two, three, four, five, six, seven, eight, nine, ten, eleven, twelve, or more arginine (R) residues, which may be consecutive or non-consecutive in the amino acid sequence. In some embodiments, the cell penetrating peptide comprises or consists of a sequence in Table 2, or a fragment or variant thereof that is capable of enhancing penetration of the polypeptide (e.g., compared to a polypeptide not containing the cell penetrating peptide). In some embodiments, the cell penetrating peptide comprises or consists of the amino acid sequence RKKRRQRRR (SEQ ID NO: 25), or a fragment or variant thereof that is capable of enhancing penetration of the polypeptide (e.g., compared to a polypeptide not containing the cell penetrating peptide). In some embodiments, the fragment has one, two or three amino acid deletions from the N and/or C terminus of an amino acid sequence provided in Table 2. In some embodiments, the variant has one, two or three amino acid substitutions (e.g., conservative amino acid substitutions) in an amino acid sequence provided in Table 2. In some embodiments, the cell penetrating peptide is no more than 70, no more than 60, no more than 50, no more than 40, no more than 30, no more than 25, or no more than 20 amino acids in length. In some embodiments, the cell penetrating peptide is between 5 and 70, 10 and 70, 5 and 60, 10 and 60, 5 and 50, 10 and 50, 5 and 40, 10 and 40, 5 and 30, 10 and 30, 5 and 25, 10 and 25, 5 and 20, or 10 and 20 amino acids in length.

In some embodiments, an Nrf2 peptide is a peptide that enhances binding of a polypeptide containing the peptide to Keap-1 compared to a polypeptide lacking the Nrf2 peptide. Binding of a polypeptide to Keap-1 can be detected using any method known in the art or described herein, e.g., co-immunoprecipitation, yeast-two hybrid, phage display and other similar assays, which may be performed in in vitro or in a cell ex vivo. In some embodiments, a level of mRNA of a downstream target of Keap-1 is measured, e.g., a level of Nqo1, GSTM1, or IL-1beta in a cell. In some embodiments, the cell is a ARPE-19 cell or HEK293T cell. In some embodiments, the Nrf2 peptide comprises or consists of the amino acid sequence LQLDEETGEFLPIQ (SEQ ID NO: 1), or a fragment or variant thereof that is capable of binding Keap-1. In some embodiments, the fragment has one, two or three amino acid deletions from the N and/or C terminus of the amino acid sequence LQLDEETGEFLPIQ (SEQ ID NO: 1). In some embodiments, the variant has one, two or three amino acid substitutions (e.g., conservative amino acid substitutions) in the amino acid sequence LQLDEETGEFLPIQ (SEQ ID NO: 1). In some embodiments, the Nrf2 peptide is no more than 50, no more than 40, no more than 30, no more than 25, or no more than 20 amino acids in length. In some embodiments, the Nrf2 peptide is between 5 and 50, 10 and 50, 5 and 40, 10 and 40, 5 and 30, 10 and 30, 5 and 25, 10 and 25, 5 and 10 or 10 and 10 amino acids in length.

In some embodiments, a carrier protein is a protein that stabilizes a polypeptide containing the protein in a cell or subject (e.g., by preventing degradation or clearance of the polypeptide) compared to a polypeptide not containing the protein. In some embodiments, a carrier protein is a protein that enhances expression of a polypeptide containing the protein in a cell or subject (e.g., by preventing degradation or increasing the efficiency of translation) compared to a polypeptide not containing the protein. In some embodiments a carrier protein contains a regulated protein destabilization domain (e.g., DHFR or FKBP). In some embodiments, the regulated protein destabilization domain permits regulation of protein stability by small molecules (e.g., trimethoprim or Shield-1), allowing for synthesis of the recombinant polypeptide to be regulated at the level of protein stability. In some embodiments, the carrier protein has one or more of the above-mentioned properties. Stability or expression of a polypeptide can be determined using any method known in the art or described herein, e.g., by measuring pharmacokinetics in a subject or by detection of polypeptide levels in a cell or tissue, e.g., by Western blot, ELISA, immunohistochemistry, and other similar assays. In some embodiments, the cell is a ARPE-19 cell or HEK293T cell. In some embodiments, the tissue is retina or another tissue of the eye. In some embodiments, the carrier protein is a human protein, such as a human protein that is expressed in the eye. In some embodiments, the carrier protein is a protein or domain (or combination thereof) described in Table 3, or a fragment or variant thereof that is capable of stabilizing a polypeptide (e.g., compared to a polypeptide not containing the carrier protein). In some embodiments, the fragment has one, two or three amino acid deletions from the N and/or C terminus of a protein or domain provided in Table 3. In some embodiments, the variant has one, two or three amino acid substitutions (e.g., conservative amino acid substitutions) in a protein or domain provided in Table 3. In some embodiments, the carrier protein has a size of between 20 kiloDaltons (KDa) and 60 KDa, 30 KDa and 60 KDa, 40 KDa and 60 KDa, 50 KDa and 60 KDa, 20 KDa and 50 KDa, 30 KDa and 50 KDa, 30 KDa and 40 KDa, 40 KDa and 60 KDa, or 40 KDa and 50 KDa.

Exemplary, non-limiting secretion signals, cell penetrating peptides, and carrier proteins are provided in Tables 1-3 below. Sequences of the carrier proteins in Table 3 can be determined by using the identifiers provided in public databases, such as the NCBI database.

TABLE 1

Exemplary Secretion Signals

| Protein | UniProt Number | SEQ ID NO. | Secretion Signal Sequence |
|---|---|---|---|
| Ig-kappa chain V-III region | P01658 | 2 | METDTLLLWVLLLWVPGSTG |
| CNTF | P26992 | 3 | MAAPVPWACCAVLAAAAAVVYA |
| PEDF | P36955 | 4 | MQALVLLLCIGALLGHSSC |
| FGF10 | O15520 | 5 | MWKWILTHCASAFPHLPGCCCCCFL LLFLVSSVPVTC |

TABLE 1-continued

Exemplary Secretion Signals

| Protein | UniProt Number | SEQ ID NO. | Secretion Signal Sequence |
|---|---|---|---|
| PDGF-A | P04085 | 6 | MRTLACLLLLGCYLAHVLA |
| Gas6 | Q14393 | 7 | MAPSLSPGPAALRRAPCILLLLLLA AECALA |
| TIMP3 | P35625 | 8 | MTPWLGLIVLLGSWSLGDWGAEA |
| VEGF-A | P15692 | 9 | MNFLLSWVHWSLALLLYLHHAKWSQA |
| TGF-b1 | P01137 | 10 | MPPSGLRLLLLLLPLLWLLVLTPGR PAAG |
| CFH | P08603 | 11 | MRLLAKIICLMLWAICVA |
| IL-8 | P10145 | 12 | MTSKLAVALLAAFLISAALC |
| MCP-1 | P13500 | 13 | MKVSAALLCLLLIAATFIPQGLA |
| GDNF | P39905 | 14 | MKLWDVVAVCLVLLHTASA |

TABLE 2

Exemplary Cell Penetrating Peptides

| Sequence | SEQ ID NO. | Origin |
|---|---|---|
| From Heparan Binding Proteins | | |
| RKKRRRESRKKRRRES | 15 | DPV3 |
| GRPRESGKKRKRKRLKP | 16 | DPV6 |
| GKRKKKGKLGKKRDP | 17 | DPV7 |
| GKRKKKGKLGKKRPRSR | 18 | DPV7b |
| RKKRRRESRRARRSPRHL | 19 | DPV3/10 |
| SRRARRSPRESGKKRKRKR | 20 | DPV10/6 |
| VKRGLKLRHVRPRVTRMDV | 21 | DPV1047 |
| SRRARRSPRHLGSG | 22 | DPV10 |
| LRRERQSRLRRERQSR | 23 | DPV15 |
| GAYDLRRRERQSRLRRRERQSR | 24 | DPV15b |
| From RNA Binding Proteins | | |
| RKKRRQRRR | 25 | HIV-1 Tat |
| RRRRNRTRRNRRRVR | 26 | FHV coat |
| TRQARRNRRRRWRERQR | 27 | HIV-1 Rev |
| TRRQRTRRARRNR | 28 | HTLV-II Rex |
| KMTRAQRRAAARRNRWTAR | 29 | BMV Gag |
| NAKTRRHERRRKLAIER | 30 | P22N |
| MDAQTRRRERRAEKQAQWKAAN | 31 | λN(1-22) |
| TAKTRYKARRAELIAERR | 32 | (φ21N(12-29) |
| TRRNKRNRIQEQLNRK | 33 | Yeast PrP6 |
| From DNA Binding Proteins | | |
| PRRRRSSSRPVRRRRRPRVSRRRRRGGRRRR | 34 | Protamine 1 |
| RIKAERKRMRNRIAASKSRKRKLERIAR | 35 | Human cJun |
| KRRIRRERNKMAAAKSRNRRRELTDT | 36 | Human cFos |
| KRARNTEAARRSRARKLQRMKQ | 37 | Yeast GCN4 |

TABLE 2-continued

Exemplary Cell Penetrating Peptides

| Sequence | SEQ ID NO. | Origin |
|---|---|---|
| RQIKIWFQNRRMKWKK | 38 | Penetratin |
| RVIRVWFQNRCKDKK | 39 | Islet-1 |
| SKRTRQTYTRYQTLELEKEFHFNRYITRRRIDIANAL SLSERQIKIWFQNRRMKSKKDR | 40 | Fushi-tarazu |
| SQIKIWFQNKRAKIKK | 41 | Engrailed-2 |
| RQVTIWFQNRRVKEKK | 42 | HoxA-13 |
| KQINNWFINQRKRHWK | 43 | Knotted-1 |
| RHIKIWFQNRRMKWKK | 44 | PDX-1 |
| From Signal Peptide | | |
| MGLGLHLLVLAAALQGAKKKRKV | 45 | Ig(v) |
| MVKSKIGSWILVLFVAMWSDVGLCKKRPKP | 46 | BPrPp(1-30) |
| MANLGYWLLALFVTMWTDVGLCKKRPKP | 47 | MPrPp(1-28) |
| AAVLLPVLLAAPVQRKRQKLP | 48 | K-FGF + NLS |
| AAVLLPVLLAAP | 49 | K-FGF + NLS |
| From antimicrobial peptides | | |
| RRIRPRPPRLPRPRPRPLPFPRPG | 50 | Bac7 |
| VDKGSYLPRPTPPRPIYNRN | 51 | Pyrrhocoricin |
| KCFQWQRNMRKVRGPPVSCIKR | 52 | Human Lactoferrin (19-40) |
| TRSSRAGLQWPVGRVHRLLRK | 53 | Buforin 2 |
| GIGAVLKVLTTGLPALISWIKRKRQQ | 54 | Melittin |
| GIGKWLHSAKKFGKAFVGEIMNS | 55 | Magainin 2 |
| LLGDFFRKSKEKIGKEFKRIVQRIKDFLRNLVPRTESC | 56 | LL-37 |
| RGGRLSYSRRRFSTSTGR | 57 | SynB1 |
| YKQCHKKGGKKGSG | 58 | Crotamine |
| ALWKTLLKKVLKAPKKKRKV | 59 | S4(13)-PV(rev) |
| HARIKPTFRRLKWKYKGKFW | 60 | L-2 |
| From Viral Proteins | | |
| TKRRITPKDVIDVRSVTTEINT | 61 | E(rns) |
| RQGAARVTSWLGRQLRIAGKRLEGRSK | 62 | VP22 |
| NAATATRGRSAASRPTQRPRAPARSASRPRRPVQ | 63 | HIV-1 VPR 77-92 |
| RHSRIGIIQQRRTRNG | 64 | Ribotoxin2 L3 loop |
| KLIKGRTPIKFGKADCDRPPKHSQNGMGK | 65 | PreS2-TLM |
| PLSSIFSRIGDP | 66 | VT5 |
| DPKGDPKGVTVTVTVTGKGDPKPD | 67 | |
| From Natural Proteins | | |
| RRIPNRRPRR | 68 | HRSV |
| RLRWR | 69 | A1P6 |
| MVRRFLVTLRIRRACGPPRVRV | 70 | ARF(1-22) |

TABLE 2-continued

Exemplary Cell Penetrating Peptides

| Sequence | SEQ ID NO. | Origin |
|---|---|---|
| MVTVLFRRLRIRRACGPPRVRV | 71 | M918 |
| LLIILRRRIRKQAHAHSK | 72 | pVEC |
| LSTAADMQGVVTDGMASG | 73 | Azurin p18 |
| LSTAADMQGVVTDGMASGLDKDYLKPDD | 74 | Azurin p28 |
| KFHTFPQTAIGVGAP | 75 | hCT18-32 |
| VPTLK (PMLKE, VPALR, VSALK, IPALK) | 76, 77, 78, 79, 80 | Bip |
| PFVYLI | 81 | C105Y |
| PIEVCMYREP | 82 | FGF12 |

From Peptide Libraries

| Sequence | SEQ ID NO. | Origin |
|---|---|---|
| R8, R9, R10, R12 | 83, 84, 85, 86 | Polyarginine |
| KETWWETWWTEWSQPKKRKV | 87 | Pep-1 |
| GLAFLGFLGAAGSTMGAWSQPKKKRKV | 88 | MPG |
| GWTLNSAGYLLGKINLKALAALAKKIL | 89 | Transportan |
| AGYLLGHINLHHLAHLAibHHIL | 90 | TH |
| KLALKALKALKAALKLA | 91 | MAP |
| RRWWRRWRR | 92 | W/R |
| GLWRALWRLLRSLWRLLWRA | 93 | CADY |
| LIRLWSHLIHIWFQNRRLKWKKK | 94 | EB-1 |
| WEAALAEALAEALAEHLAEALAEALEALAA | 95 | GALA |
| LKTLTETLKELTKTLTEL | 96 | MAP12 |
| QLALQLALQALQAALQLA | 97 | MAP17 |
| (PPR)3, (PPR)4, (PPR)5, (PPR)6 | 98, 99, 100, 101 | (PPR)n |
| (PRR)3, (PRR)4, (PRR)5, (PRR)6 | 102, 103, 104, 105 | (PRR)n |
| GPSQPTYPGDDAPVRDLIRFYRDLQRYLNVVTRHRY | 106 | aPP4R1 |
| GPSQPTYPGDDAPVRDLIRFYRDLRRYLNVVTRHRY | 107 | aPP5R1 |
| GPSQPTYPGDDAPVRDLRRFYRDLRRYLNVVTRHRY | 108 | aPP6R1 |
| G(PLXX)NPI | 109 | PoliProline-based |
| VRLPPPVRLPPPVRLPPP | 110 | SAP |
| VELPPPVELPPPVELPPP | 111 | SAP(E) |
| FKIYDKKVRTRVVKH | 112 | SVM1 |
| RASKRDGSWVKKLHRILE | 113 | SVM2 |
| KGTYKKKLMRIPLKGT | 114 | SVM3 |
| LYKKGPAKKGRPPLRGWFH | 115 | SVM4 |
| HSPIIPLGTRFVCHGVT | 116 | SVM5 |
| YTAIAWVKAFIRKLRK | 117 | YTA2 |
| IAWVKAFIRKLRKGPLG | 118 | YTA4 |

TABLE 2-continued

Exemplary Cell Penetrating Peptides

| Sequence | SEQ ID NO. | Origin |
|---|---|---|
| RLSGMNEVLSFRWL | 119 | SG3 |
| SDLWEMMMVSLACQY | 120 | Pep-7 |
| VTWTPQAWFQWV | 121 | |
| GSPWGLQHHPPRT | 122 | 439a |
| GPFHFYQFLFPPV | 123 | 435b |
| TSPLNIHNGQKL | 124 | HN-1 |
| CAYHRLRRC | 125 | |
| RCGRASRCRVRWMRRRRI | 126 | BEN_1079 |
| PYSRPHVQLWYPNRESCRSLIRSLGP | 127 | BEN_0805 |
| PLILLRLLRGQF | 128 | Pept1 |
| PLIYLRLLRGQF | 129 | Pept2 |
| KLWMRWYSPTTRRYG | 130 | IW-14 |

TABLE 3

Exemplary Carrier Proteins

| Protein | Description | References | Protein Sequence ID |
|---|---|---|---|
| Opticin | Ocular protein expressed within the retina | PMID: 10636917, PMID: 22669977 | CAB53459 |
| Human Serum Albumin | Carrier protein normally present in human serum | PMID: 6171778, PMID: 6275391 | NP_000468 |
| Dihidrofolate Reductase (DHFR) destabilization domain | Domain from E. coli DHFR that allows the stabilization of a fused protein only in the presence of trimethoprim | PMID: 20851347, PMID: 23029456 | AIW05158 |
| FK506 binding protein (FKBP) destabilization domain | Domain from the FK506 binding protein that allows the stabilization of a fused protein only in the presence of its ligand Shield-1 | PMID: 16959577, PMID: 18836461 | AAD40379 |

TABLE 4

Exemplary Enzymes having nucleic acid cleavage sites

| Protease | Description | UniProt |
|---|---|---|
| PCSK1 | Performs proteolytic cleavage of several prohormones | P29120 |
| PCSK2 | Performs proteolytic cleavage of several prohormones | P16519 |
| Furin | Protease enriched in the Golgi apparatus involved in the processing of precursor proteins | P09958 |
| PCSK4 | Proprotein convertase | Q6UW60 |
| PCSK5 | Proprotein convertase involved in the processing of sevral integrin alpha subunits | Q92824 |
| PCSK6 | Proprotein convertase known to cleave NODAL during development | P29122 |
| PCSK7 | Proprotein convertase enriched in the trans-Golgi network | Q16549 |
| MBTPS1 | Proprotein convertase which cleaves the ER loop of SREBP transcription factors | Q14703 |
| PCSK9 | Proprotein convertase that plays a major role in cholesterol homeostasis | Q8NBP7 |

According to some embodiments, provided is a method for the prevention, amelioration, or treatment of a disease or condition associated with oxidative stress or inflammation in a subject comprising administration of a therapeutically effective amount of a compound to the subject, wherein the compound is a recombinant polypeptide as described herein (e.g., comprising a cell penetrating peptide and an Nrf2 peptide as described herein). In some embodiments, the polypeptide comprises a secretion signal, a cell penetrating peptide, and an Nrf2 peptide as described herein. In some embodiments, the recombinant polypeptide comprises a secretion signal, a carrier protein, a cell penetrating peptide, and an Nrf2 peptide as described herein. In some embodiments, the secretion signal, cell penetrating peptide, Nrf2 peptide and/or carrier protein are connected without any spacers. In some embodiments, the secretion signal, cell penetrating peptide, Nrf2 peptide and/or carrier protein are linked to one another by one or more spacers, e.g., one or more amino acids. In some embodiments, the spacer comprises an enzyme cleavage site, such as a furin cleavage site, e.g., between the carrier protein and the cell penetrating peptide.

In some embodiments, provided is a method of preventing, ameliorating or treating inflammation, such as retinal and RPE inflammation, the method comprising administration of a recombinant polypeptide as described herein (e.g., comprising a cell penetrating peptide and an Nrf2 peptide as described herein). In some embodiments, the recombinant polypeptide comprises a secretion signal, a cell penetrating peptide, and an Nrf2 peptide as described herein. In some embodiments, the recombinant polypeptide comprises a secretion signal, a carrier protein, a cell penetrating peptide, and an Nrf2 peptide as described herein. In some embodiments, the secretion signal, cell penetrating peptide, Nrf2 peptide and/or carrier protein are connected without any spacers. In some embodiments, the secretion signal, cell penetrating peptide, Nrf2 peptide and/or carrier protein are linked to one another by one or more spacers, e.g., one or more amino acids. In some embodiments, the spacer comprises an enzyme cleavage site, such as a furin cleavage site, e.g., between the carrier protein and the cell penetrating peptide. In some embodiments, the recombinant polypeptide is secreted from cells transfected with an AAV vector engineered to express the recombinant polypeptide.

In some embodiments, provided is a viral vector engineered to express a recombinant polypeptide as described herein (e.g., comprising a cell penetrating peptide and an Nrf2 peptide as described herein). In some embodiments, the recombinant polypeptide comprises a secretion signal, a cell penetrating peptide, and an Nrf2 peptide as described herein. In some embodiments, the recombinant polypeptide comprises a secretion signal, a carrier protein, a cell penetrating peptide, and an Nrf2 peptide as described herein. In some embodiments, the secretion signal, cell penetrating peptide, Nrf2 peptide and/or carrier protein are connected without any spacers. In some embodiments, the secretion signal, cell penetrating peptide, Nrf2 peptide and/or carrier protein are linked to one another by one or more spacers, e.g., one or more amino acids. In some embodiments, the spacer comprises an enzyme cleavage site, such as a furin cleavage site, e.g., between the carrier protein and the cell penetrating peptide. In some embodiments, the viral vector is an AAV plasmid or a lentiviral plasmid. In some embodiments, the viral vector is a recombinant AAV or lentiviral genome, e.g., encapsidated in an AAV or lentiviral capsid.

In some embodiments, provided are cells stably transfected with a nucleotide sequence encoding a recombinant polypeptide as described herein. In some embodiments, the recombinant polypeptide comprises a secretion signal, a carrier protein, a cell penetrating peptide, and an Nrf2 peptide as described herein.

According to some embodiments, also provided is a method for the prevention, amelioration, or treatment of a disease or condition associated with oxidative stress or inflammation in a subject comprising administration of a therapeutically effective amount of a compound to the subject, wherein the compound is an Nrf2-14mer polypeptide. In a specific embodiment, the Nrf2 polypeptide (e.g., a recombinant Nrf2 polypeptide) is a TatNrf2mer polypeptide, or a polypeptide having substantial sequence homology therewith.

In some embodiments, provided is a method of preventing, ameliorating or treating retinal and RPE inflammation that involves administration of an Nrf2 polypeptide (e.g., a recombinant Nrf2 polypeptide). In some embodiments, the Nrf2 polypeptide is secreted from cells transfected with an AAV vector engineered to express Nrf2, and in particular TatNrf2mer.

In some embodiments, provided is a viral vector engineered to express TatNrf2mer. In specific embodiments, the viral vector is an AAV plasmid or a lentiviral plasmid.

In some embodiments, provided are cells stably transfected with a nucleotide sequence encoding an Nrf2 polypeptide (e.g., a recombinant Nrf2 polypeptide). In a specific embodiment, the Nrf2 polypeptide is TatNrf2mer.

Vectors

In some embodiments, viral vectors are used to transfect cells with a recombinant polypeptide or TatNrf2mer expression construct. In a particular embodiment, adeno-associated viral vectors are used. Other vectors of the disclosure used in vitro, in vivo, and ex vivo include viral vectors, such as retroviruses (including lentiviruses), herpes viruses, alphavirus, adenovirus, vaccinia virus, papillomavirus, or Epstein Barr virus (EBV).

Methods for constructing and using viral vectors are known in the art (see, e.g., Miller and Rosman, BioTechniques 1992, 7:980-990). In accordance with the present disclosure there may be employed conventional molecular biology, microbiology, and recombinant DNA techniques within the skill of the art. Such techniques are well-known and are explained fully in the literature. See, e.g., Sambrook, Fritsch and Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors) and Origene (Rockville, Md.).

In some embodiments, the viral vectors of the disclosure are replication defective, that is, they are unable to replicate autonomously in the target cell. In some embodiments, the replication defective virus is a minimal virus, i.e., it retains only the sequences of its genome which are necessary for target cell recognition and encapsidating the viral genome. Replication defective virus is not infective after introduction into a cell. Use of replication defective viral vectors allows for administration to cells in a specific, localized area, without concern that the vector can infect other cells. Thus, a specific tissue can be specifically targeted. Examples of particular vectors include, but are not limited to, defective herpes virus vectors (see, e.g., Kaplitt et al., Molec. Cell. Neurosci. 1991, 2:320-330; Patent Publication RD 371005 A; PCT Publications No. WO 94/21807 and WO 92/05263), defective adenovirus vectors (see, e.g., Stratford-Perricaudet et al., J. Clin. Invest. 1992, 90:626-630; La Salle et al., Science 1993, 259:988-990; PCT Publications No. WO 94/26914, WO 95/02697, WO 94/28938, WO 94/28152, WO 94/12649, WO 95/02697, and WO 96/22378), and defective adeno-associated virus vectors (Samulski et al., J. Virol. 1987, 61:3096-3101; Samulski et al., J. Virol. 1989, 63:3822-3828; Lebkowski et al., Mol. Cell. Biol. 1988, 8:3988-3996; PCT Publications No. WO 91/18088 and WO 93/09239; U.S. Pat. Nos. 4,797,368 and 5,139,941; European Publication No. EP 488 528).

Adeno-Associated Virus-Based Vectors.

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see PCT Publications No. WO 91/18088 and WO 93/09239; U.S. Pat. Nos. 4,797,368 and 5,139,941; EP Publication No. 488 528). The replication defective recombinant AAVs according to the disclosure can be prepared by cotransfecting a plasmid containing the nucleic acid sequence of interest (e.g., encoding a recombinant polypeptide as described herein) flanked by two AAV inverted terminal repeat (ITR) regions, and a plasmid carrying the AAV encapsidation genes (rep and cap genes), into a cell line which is infected with a human helper virus (e.g., an adenovirus). The AAV recombinants which are produced are then purified by standard techniques. In some embodiments, the AAV recombinant vector is an AAV2 quad vector encapsidated by a capsid comprising modified AAV2 capsid proteins having non-tyrosine residues (e.g., phenylalanines) corresponding to the positions Y272, Y444, Y500, and Y730 of a wild-type AAV2 capsid.

Adenovirus-Based Vectors.

Adenoviruses are eukaryotic DNA viruses that can be modified to efficiently deliver a nucleic acid of the disclosure to a variety of cell types. Various serotypes of adenovirus exist. Of these serotypes, in some embodiments, preference is given, within the scope of the present disclosure, to using type 2 or type 5 human adenoviruses (Ad 2 or Ad 5) or adenoviruses of animal origin (see PCT Publication No. WO94/26914). Those adenoviruses of animal origin which can be used within the scope of the present disclosure include adenoviruses of canine, bovine, murine (e.g., Mav1 [Beard et al., Virology, 1990, 75:81]), ovine, porcine, avian, and simian (e.g., SAV) origin. In some embodiments, the adenovirus of animal origin is a canine adenovirus, such as a CAV2 adenovirus (e.g., Manhattan or A26/61 strain [ATCC Accession No. VR-800]). Various replication defective adenovirus and minimum adenovirus vectors have been described (PCT Publications No. WO94/26914, WO95/02697, WO94/28938, WO94/28152, WO94/12649, WO95/02697, WO96/22378). The replication defective recombinant adenoviruses according to the disclosure can be prepared by any technique known to the person skilled in the art (Levrero et al., Gene, 1991, 101:195; EP Publication No. 185 573; Graham, EMBO J., 1984, 3:2917; Graham et al., J. Gen. Virol., 1977, 36:59). Recombinant adenoviruses are recovered and purified using standard molecular biological techniques, which are well known to one of ordinary skill in the art.

Retroviral Vectors.

In some embodiments, the disclosure provides retroviral vectors, e.g., as described in Mann et al., Cell 1983, 33:153; U.S. Pat. Nos. 4,650,764, 4,980,289, 5,124,263, and 5,399,346; Markowitz et al., J. Virol. 1988, 62:1120; EP Publications No. 453 242 and 178 220; Bernstein et al. Genet. Eng. 1985, 7:235; McCormick, BioTechnology 1985, 3:689; and Kuo et al., 1993, Blood, 82:845. The retroviruses are integrating viruses which infect dividing cells. The retrovirus genome includes two LTRs, an encapsidation sequence and three coding regions (gag, pol and env). Replication defective non-infectious retroviral vectors are manipulated to destroy the viral packaging signal, but retain the structural genes required to package the co-introduced virus engineered to contain the heterologous gene and the packaging signals. Thus, in recombinant replication defective retroviral vectors, the gag, pol and env genes are generally deleted, in whole or in part, and replaced with a heterologous nucleic acid sequence of interest. These vectors can be constructed from different types of retroviruses, such as HIV (human immuno-deficiency virus), MoMuLV (murine Moloney leukaemia virus), MSV (murine Moloney sarcoma virus), HaSV (Harvey sarcoma virus), SNV (spleen necrosis virus), RSV (Rous sarcoma virus), and Friend virus. Suitable packaging cell lines have been described in the prior art, in particular, the cell line PA317 (U.S. Pat. No. 4,861,719); the PsiCRIP cell line (PCT Publication No. WO 90/02806) and the GP+envAm-12 cell line (PCT Publication No. WO 89/07150). In addition, recombinant retroviral vectors can contain modifications within the LTRs for suppressing transcriptional activity as well as extensive encapsidation sequences which may include a part of the gag gene (Bender et al., J. Virol. 1987, 61:1639). Recombinant retroviral vectors are purified by standard techniques known to those having ordinary skill in the art.

Retrovirus vectors can also be introduced by DNA viruses, which permits one cycle of retroviral replication and amplifies transfection efficiency (see PCT Publications No. WO 95/22617, WO 95/26411, WO 96/39036, WO 97/19182).

In some embodiments of the disclosure, lentiviral vectors can be used as agents for the direct delivery and sustained expression of a transgene in several tissue types, including brain, retina, muscle, liver, and blood. This subtype of retroviral vectors can efficiently transduce dividing and nondividing cells in these tissues, and maintain long-term expression of the gene of interest (for a review, see, Naldini, Curr. Opin. Biotechnol. 1998, 9:457-63; Zufferey, et al., J. Virol. 1998, 72:9873-80). Lentiviral packaging cell lines are available and known generally in the art (see, e.g., Kafri, et al., J. Virol., 1999, 73: 576-584).

Non-Viral Vectors.

In some embodiments, the disclosure provides non-viral vectors that can be introduced in vivo, provided that these vectors contain a targeting peptide, protein, antibody, etc. that specifically binds HALR. For example, compositions of synthetic cationic lipids, which can be used to prepare liposomes for in vivo transfection of a vector carrying an anti-tumor therapeutic gene, are described in Felgner et. al., Proc. Natl. Acad. Sci. USA 1987, 84:7413-7417; Felgner and Ringold, Science 1989, 337:387-388; Mackey, et al., Proc. Natl. Acad. Sci. USA 1988, 85:8027-8031; and Ulmer et al, Science 1993, 259:1745-1748. Useful lipid compounds and compositions for transfer of nucleic acids are described, e.g., in PCT Publications No. WO 95/18863 and WO96/17823, and in U.S. Pat. No. 5,459,127. Targeting peptides, e.g., laminin or HALR-binding laminin peptides, and proteins such as anti-HALR antibodies, or non-peptide molecules can be coupled to liposomes covalently (e.g., by conjugation of the peptide to a phospholipid or cholesterol; see also Mackey et al., supra) or non-covalently (e.g., by insertion via a membrane binding domain or moiety into the bilayer membrane).

Alphaviruses are well known in the art, and include without limitation Equine Encephalitis viruses, Semliki Forest virus and related species, Sindbis virus, and recombinant or ungrouped species (see Strauss and Strauss, Microbiol. Rev. 1994, 58:491-562, Table 1, p. 493).

As used herein the term "replication deficient virus" has its ordinary meaning, i.e., a virus that is propagation incompetent as a result of modifications to its genome. Thus, once such recombinant virus infects a cell, the only course it can follow is to express any viral and heterologous protein contained in its genome. In a specific embodiment, the replication defective vectors of the disclosure may contain genes encoding nonstructural proteins, and are self-sufficient for RNA transcription and gene expression. However, these vectors lack genes encoding structural proteins, so that a helper genome is needed to allow them to be packaged into infectious particles. In addition to providing therapeutically safe vectors, the removal of the structural proteins increases the capacity of these vectors to incorporate more than 6 kb of heterologous sequences. In another embodiment, propagation incompetence of the adenovirus vectors of the disclosure is achieved indirectly, e.g., by removing the packaging signal which allows the structural proteins to be packaged in virions being released from the packaging cell line. As discussed above, viral vectors used to transfect cells and express TatNrf2mer polypeptide may be used, and in a specific embodiment, the viral vectors involve a replication deficient virus.

Other Delivery Vehicles

Many nonviral techniques for the delivery of a nucleic acid sequence into a cell can be used, including direct naked DNA uptake (e.g., Wolff et al., Science 247: 1465-1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429-4432, 1987; Wu et al., J. Biol. Chem. 266: 14338-14342, 1991), and liposome-mediated delivery (e.g., Kaneda et al., Expt. Cell Res. 173: 56-69, 1987; Kaneda et al., Science 243: 375-378, 1989; Zhu et al., Science 261: 209-211, 1993). Many of these physical methods can be combined with one another and with viral techniques; enhancement of receptor-mediated DNA uptake can be effected, for example, by combining its use with adenovirus (Curiel et al., Proc. Natl. Acad. Sci. USA 88: 8850-8854, 1991; Cristiano et al., Proc. Natl. Acad. Sci. USA 90: 2122-2126, 1993).

Methods of Treatment and Compositions

Other aspects of the disclosure relate to a method of treating a disease or disorder associated with inflammation. In some embodiments, the method comprises administering a recombinant polypeptide as described herein or an expression construct as described herein (e.g., a nucleotide sequence encoding a recombinant polypeptide in an AAV or lentivirus) to a subject having a disease or condition characterized by or involving inflammation, such as dry AMD, diabetic retinopathy (DR), ALS, Arthritis, Uveitis (e.g., autoimmune or recurrent uveitis), Vasculitis, Behçet's Disease, Lupus erythematosus, or Nephritis.

The recombinant polypeptide as described herein or expression construct as described herein may be delivered in the form of a composition, such as a composition comprising the active ingredient, such as a recombinant polypeptide as described herein or an expression construct as described herein (e.g., in a AAV or lentivirus), and a therapeutically or pharmaceutically acceptable carrier. The recombinant polypeptide as described herein or an expression construct as described herein (e.g., in a AAV or lentivirus) may be prepared in a variety of compositions, and may also be formulated in appropriate pharmaceutical vehicles for administration to human or animal subjects.

The disclosure also provides compositions comprising one or more of the disclosed recombinant polypeptides as described herein or expression constructs as described herein (e.g., a nucleotide sequence encoding a recombinant polypeptide in an AAV or lentivirus). As described herein, such compositions may further comprise a pharmaceutical excipient, buffer, or diluent, and may be formulated for administration to an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof.

In some embodiments, the number of viral particles (e.g., lentivirus or AAV particles) administered to a subject may be on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, viral particles of higher than $10^{13}$ particles/ml are be administered. In some embodiments, the number of viral particles administered to a subject may be on the order ranging from $10^6$ to $10^{14}$ vector genomes(vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, viral particles of higher than $10^{13}$ vgs/ml are be administered. The viral particles can be administered as a single dose, or divided into two or more administrations as may be required to achieve therapy of the particular disease or disorder being treated. In some embodiments, 0.0001 ml to 10 mls are delivered to a subject.

In some embodiments, the disclosure provides formulations of one or more viral-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, recombinant polypeptides as described herein or expression constructs as described herein (e.g., a nucleotide sequence encoding a recombinant polypeptide in an AAV or lentivirus) may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravitreal, intravenous, intranasal, intraarticular, and intramuscular administration and formulation.

Typically, these formulations may contain at least about 0.1% of the therapeutic agent (e.g., recombinant polypeptide) or more, although the percentage of the active ingredient(s) may, of course, be varied and may conveniently be between about 1 or 2% and about 70% or 80% or more of the weight or volume of the total formulation. Naturally, the amount of therapeutic agent(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver recombinant polypeptides as described herein or expression constructs as described herein (e.g., a nucleotide sequence encoding a recombinant polypeptide in an AAV or lentivirus) in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. The pharmaceutical forms of the compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage may occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the recombinant polypeptides as described herein or expression constructs as described herein (e.g., a nucleotide sequence encoding a recombinant polypeptide in an AAV or lentivirus) in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, exemplary methods of preparation are vacuum-drying and freeze-drying techniques which yield a powder of the active ingredient plus any additional desired ingredient from a previously sterile-filtered solution thereof.

The amount of rAAV particle or nucleic acid vector compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of viral particles to provide therapeutic benefit to the patient undergoing such treatment. Alternatively, in some circumstances, it may be desirable to provide multiple, or successive administrations of the compositions, either over a relatively short, or a relatively prolonged period of time, as may be determined by the medical practitioner overseeing the administration of such compositions.

The composition may include recombinant polypeptides as described herein or expression constructs as described herein (e.g., a nucleotide sequence encoding a recombinant polypeptide in an AAV or lentivirus), either alone, or in combination with one or more additional active ingredients, which may be obtained from natural or recombinant sources or chemically synthesized. In some embodiments, the recombinant polypeptide is administered in combination, either in the same composition or in the same treatment regimen, with corticosteroids (e.g., for uveitis), VEGF inhibitors (e.g., ranibizumab or bevacizumab, such as for wet AMD or diabetic retinopathy), or blood glucose control agents such as insulin (e.g., for diabetic retinopathy).

Other Exemplary Embodiments

Other non-limiting, exemplary embodiments are provided below:

Embodiment 1

A method for the prevention, amelioration, or treatment of a disease or condition associated with oxidative stress or inflammation in a subject comprising administration of a therapeutically effective amount of a compound to the subject, wherein the compound is an Nrf2 polypeptide (e.g., a recombinant Nrf2 polypeptide).

Embodiment 2

The method of embodiment 1, wherein the Nrf2 polypeptide is TatNrf2-14 mer.

Embodiment 3

The method of embodiment 1, where said administration comprises secretion of TatNrf2-14 mer from cells transfected with a vector comprising a nucleotide sequence encoding TatNrf2-14 mer.

Embodiment 4

The method of embodiment 3, wherein the vector is administered to cells in the subject via intravitreal injection, subretinal injection, injection into the anterior chamber of the eye, injection or application locally to the cornea, subconjunctival injection, subtenon injection, or eye drops.

Embodiment 5

The method of embodiment 1, wherein said inflammation is ocular inflammation.

Embodiment 6

The method of embodiment 1, wherein the subject comprises an eye, and the disease or condition associated with oxidative stress comprises an ocular disease and the Nrf2 polypeptide reduces secretion of IL-1β.

Embodiment 7

A composition comprising a TatNrf2-14mer polypeptide and a pharmaceutically acceptable carrier.

Embodiment 8

The composition of embodiment 7, wherein the composition is contained in a syringe.

Embodiment 9

A viral vector comprising an expression construct comprising a nucleotide sequence encoding a TatNrf2mer polypeptide.

Embodiment 10

The viral vector of embodiment 9, wherein said viral vector is an AAV vector or lentiviral.

Embodiment 11

The viral vector of embodiment 9, wherein the expression construct further comprises a secretion signal peptide.

Embodiment 12

A cell engineered to express TatNrf2-14mer.

Embodiment 13

The cell of embodiment 12 transfected with a vector comprising a nucleotide sequence encoding a TatNrf2mer polypeptide.

Embodiment 14

The cell of embodiment 13, wherein said vector is vector is a retroviral vector, a lentiviral vector, an adenoviral vector, a Herpes viral vector, a Hepatitis viral vector, an SV40 vector, an EBV vector, an adeno-associated virus (AAV) vector or a nonviral vector.

Embodiment 15

The method of embodiment 1, wherein the disease is selected from the group consisting of macular degeneration, age-related macular degeneration (AMD), geographic atrophy, wet AMD, dry AMD, drusen formation, dry eye, diabetic retinopathy, vitreoretinopathy, corneal inflammation, uveitis, ocular hypertension or glaucoma.

Embodiment 16

An ocular device loaded with the viral vector of embodiment 9.

Embodiment 17

The method of embodiment 1, wherein the Nrf2 polypeptide is TatNrf2mer delivered locally to cells of the eye.

EXAMPLES

Example 1. Studies Related to Secretable TatNrf2-14mer

Figure 2:
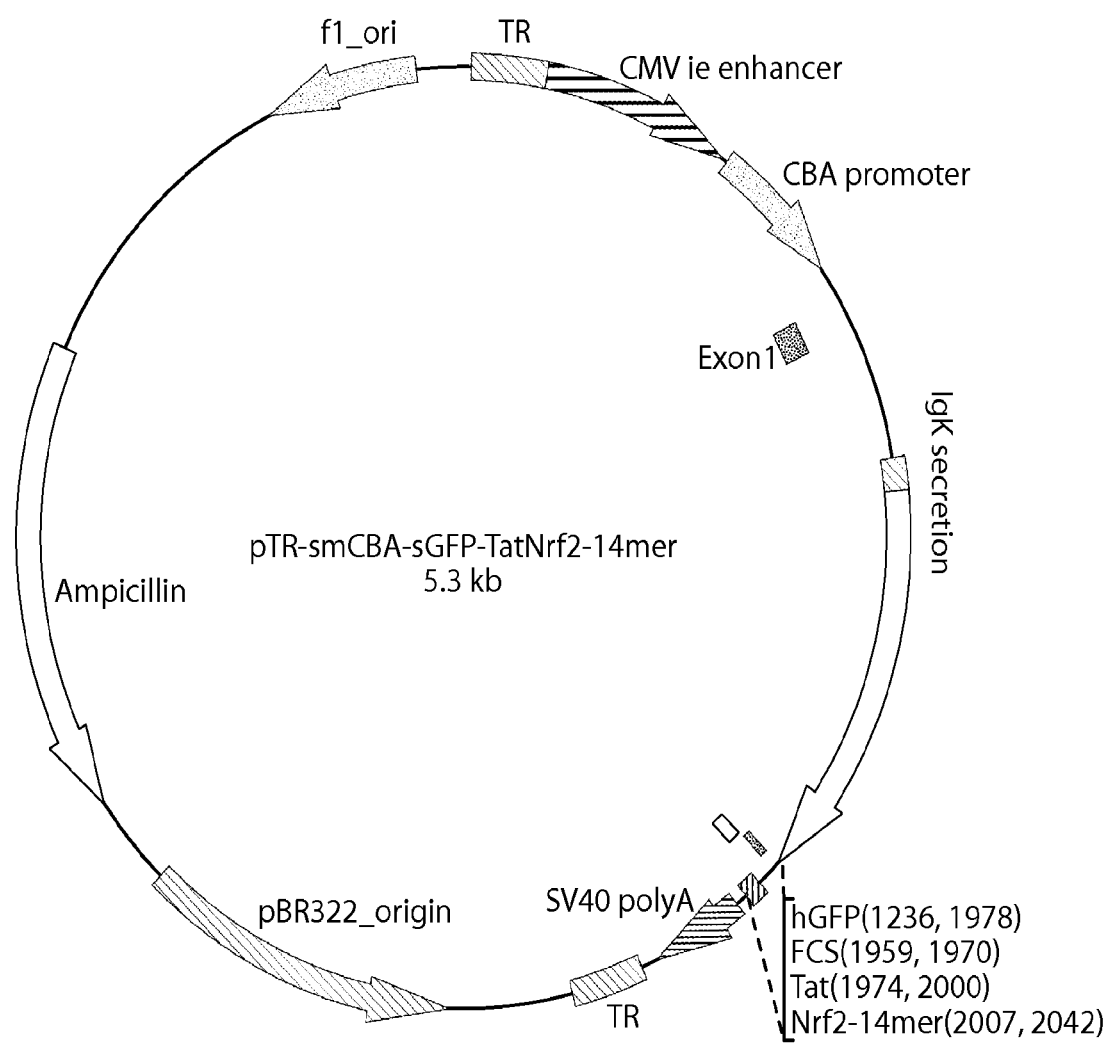
FIG. 2 is a diagram of an exemplary TatNrf2-14mer plasmid construct. The plasmid contains the CMV-chicken beta actin promoter driving the expression of a secreted GFP fused to the Tat-Nrf2 peptide gene through a furin cleavage site sequence. The insert is surrounded by terminal repeat (TR) sites for packaging in AAV.
Figure 3:
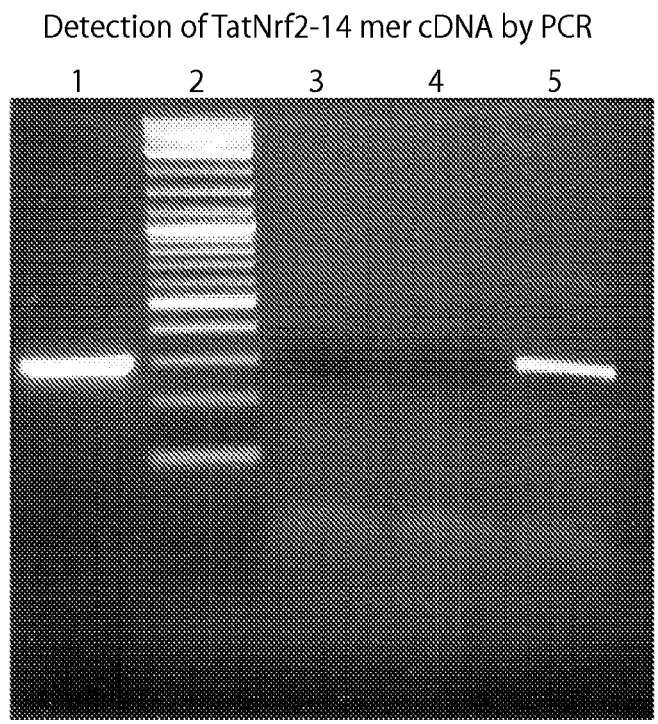
FIG. 3 is a photograph of a gel showing detection of exemplary TatNrf2-14mer cDNA by PCR. The mRNA encoding the Tat-Nrf2-14mer peptide could be detected in cells transfected with pTRsmCBA-sGFP-TatNrf2 14mer (lane 5) but not in untransfected cells (lane 3) or in cells transfected with pTRsmCBA-sGFP plasmid (lane 4).
Figure 4:
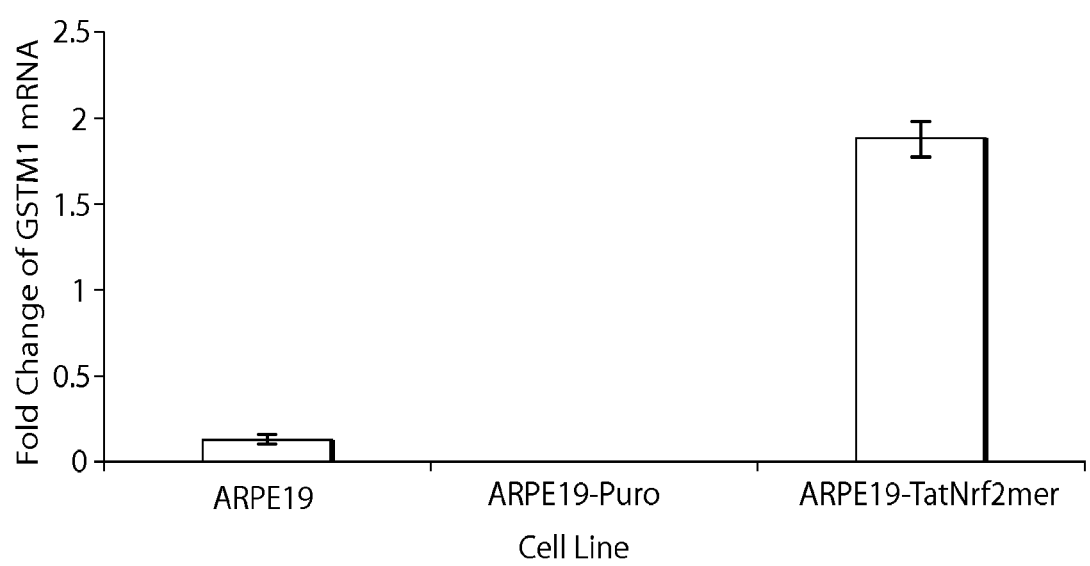
FIG. 4 is a graph showing that the exemplary TatNrf2-14mer Peptide Enhances GSTM1 Gene Transcription. Human retinal pigment epithelial cells treated with the TatNrf2 plasmid produce 18 fold more GSTM1 mRNA than untreated cells. GSTM1 is an antioxidant enzyme and marker of the ARE response.
Figure 5:
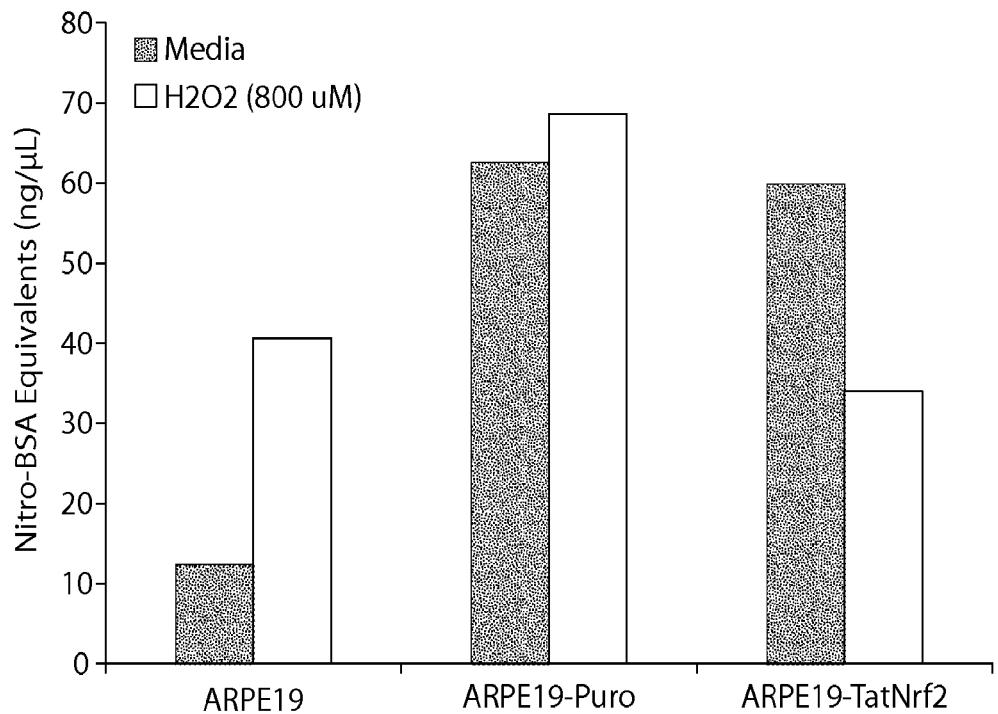
FIG. 5 is a graph showing that exemplary TatNrf2-14mer Peptide Expression Decreases Cell Nitrotyrosine Modification in $H_2O_2$ Treated ARPE-19 cells. Human retinal pigment epithelial cells treated with the TatNrf2 plasmid produce less oxidized protein than control cells following treatment with hydrogen peroxide ($H_2O_2$-red bars).
Figure 6:
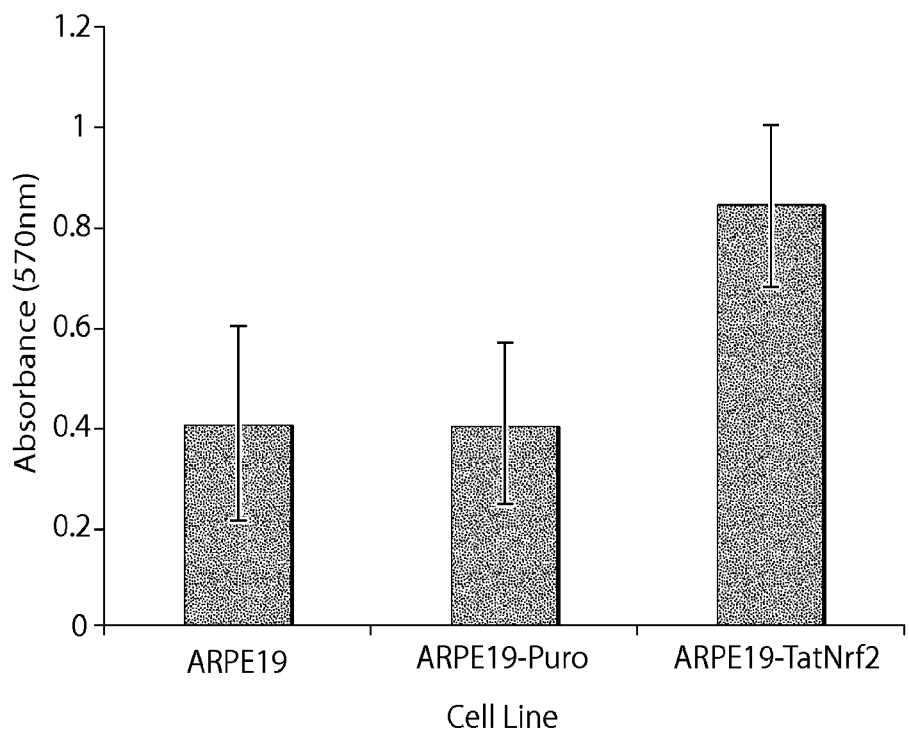
FIG. 6 is a graph showing that exemplary TatNrf2-14mer Peptide Expression Increases Cell Viability of $H_2O_2$ Treated ARPE-19 Cells. Human retinal pigment epithelial cells treated with the TatNrf2 plasmid remain more viable than control cells following treatment with hydrogen peroxide.
Figure 7:
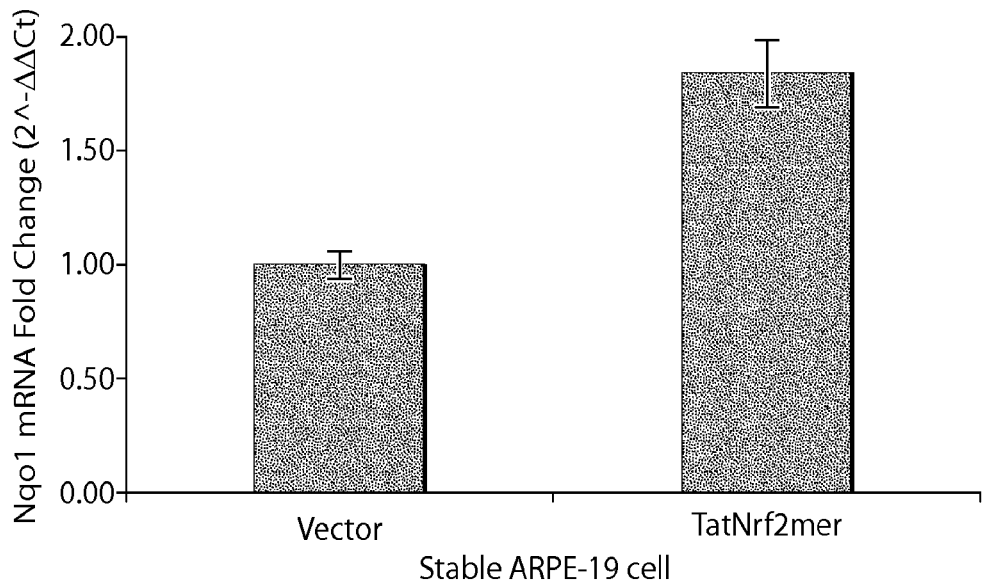
FIG. 7 is a graph showing that expression of an exemplary Tat-Nrf2 peptide fusion (TatNrf2mer) in ARPE-19 cells increases Nqo1 mRNA levels. ARPE-19 cells transduced with lentiviral vectors delivering either the TatNrf2mer or the puromycin resistance gene only (Vector) were selected in media containing puromycin (1 µg/mL). Total RNA was isolated from these stable cells and a cDNA library was generated. Using an equal amount of each cDNA library, the levels of NqO1 (an ARE-regulated gene) was measured by RT-PCR with primers specific for NqO1 and GAPDH (control). Fold change was determined using the delta-delta Ct method and standardizing values to GAPDH expression. Stable expression of TatNrf2mer increases the levels of NqO1 mRNA in ARPE-19 cells.
Figure 8:
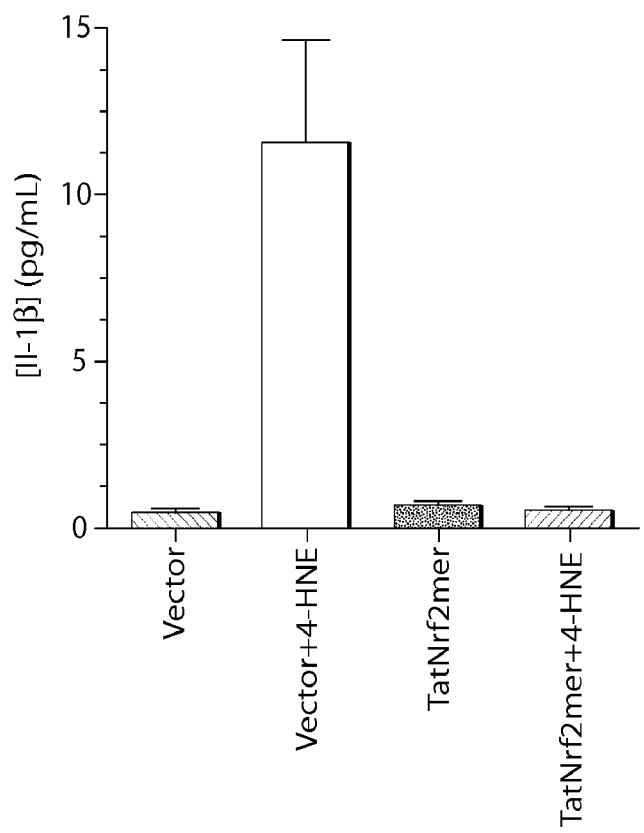
FIG. 8 is a graph showing that stable expression of exemplary TatNrf2mer blocks induced IL-1β secretion in ARPE-19 cells. ARPE-19 cells stably expressing only the puromycin resistance gene (vector) or the TatNrf2mer gene were challenged with 30 µM of the reactive aldehyde 4-hydroxynonenal (4-HNE) for 18 hrs. The levels of IL-1β in the conditioned media were quantified by ELISA. Cells expressing the TatNrf2mer showed lower concentrations of secreted IL-1β after induction with 4-HNE.
Figure 9:
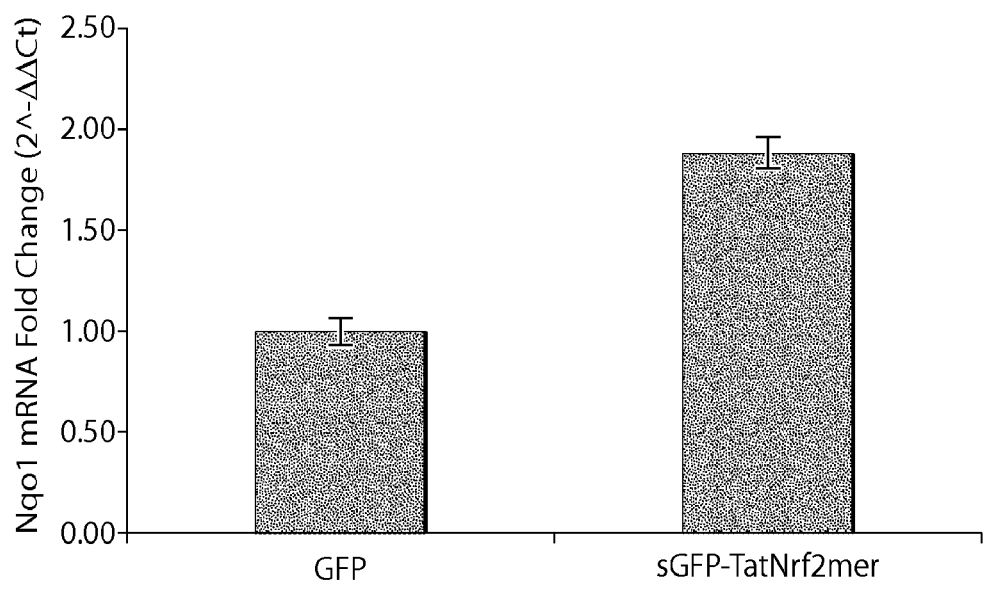
FIG. 9 is a graph showing that transient expression of an exemplary sGFP-TatNrf2mer increases NqO1 mRNA levels in vitro. HEK293T cells were transfected either with GFP or sGFP-TatNrf2mer AAV plasmid. Total RNA was isolated from these cells and a cDNA library was generated. Using an equal amount of each cDNA library, the levels of Nqo1 (an ARE-regulated gene) was measured by RT-PCR with primers specific for Nqo1 and GAPDH (control). Fold change was determined using the delta-delta Ct method and standardizing values to GAPDH expression. Transfection with the sGFP-TatNrf2mer plasmid increased the levels of NqO1 mRNA.
Figure 10:
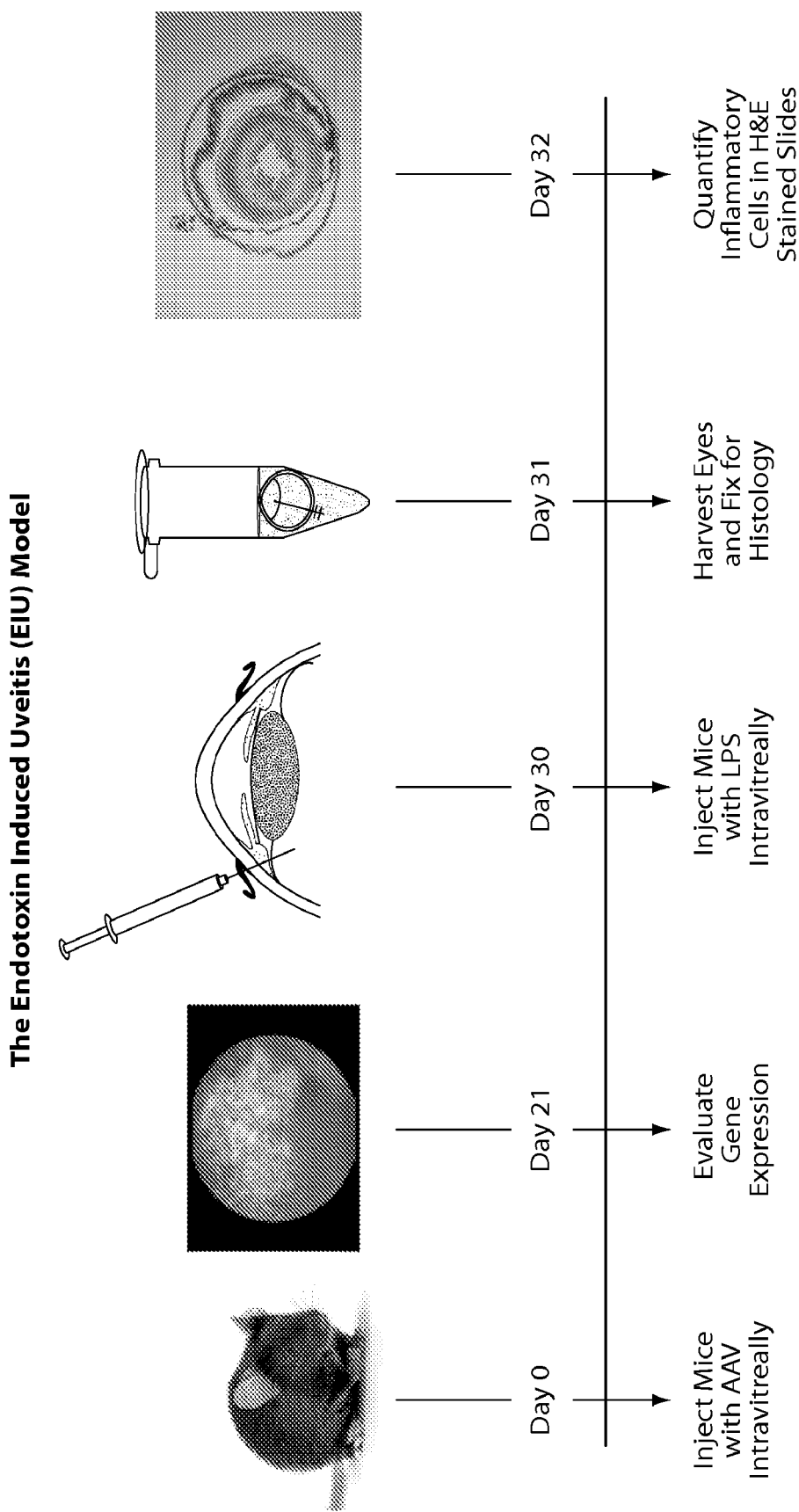
FIG. 10 is a diagram showing that the exemplary secretable TatNrf2mer ameliorates the inflammatory response of the endotoxin-induced uveitis (EIU) mouse model. Mice from the C57BL/6 strain were injected intravitreally with rAAV2QUAD/smCBA-GFP in the left eye and with rAAV2QUAD/smCBA-sGFP-TatNrf2mer in the right eye ($3 \times 10^9$ vector genomes/eye). Three weeks after the injection, the gene expression was assessed by fluorescence fundoscopy. At one month post injection, mice were injected bilaterally with 25 ng of LPS (lipopolysaccharide). After 24 hours the eyes were harvested and fixed for histological analysis. Eyes were sectioned and stained with hematoxylin and eosin (H&E) and the infiltrative cells in the vitreous body were quantified under a microscope. Eyes treated with the TatNrf2mer AAV vector had significantly lower number of infiltrative cells in the vitreous body when compared to its control GFP treated eye.
Figure 11A:
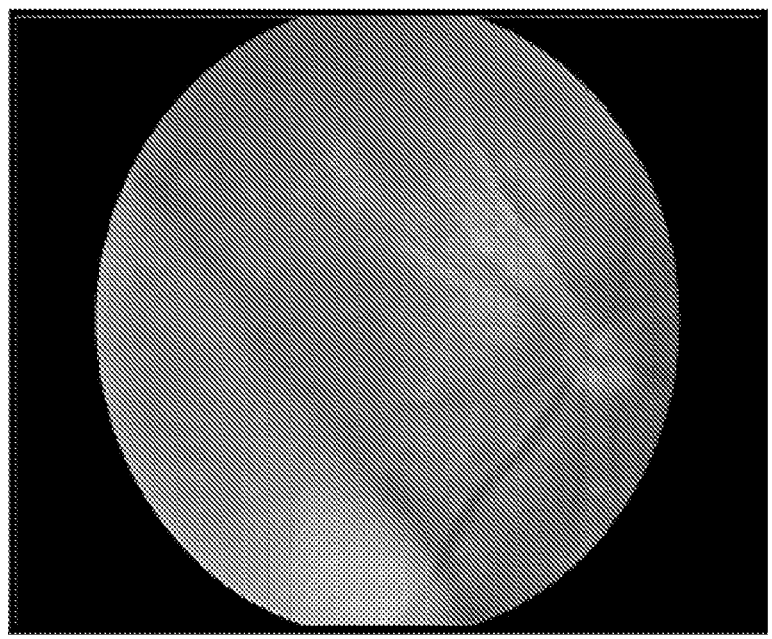
FIGS. 11A and 11B are two photographs showing fundus evaluation at month after AAV vector injection. Mice were injected intravitreally with $3 \times 10^9$ vector genomes in of AAV2QUAD/smCBA-GFP (left eye, 11A) and AAV2QUAD/smCBA-sGFP-TatNrf2mer (right eye, 11B). One month after the vector injection, mice were evaluated by fundoscopy to determine the presence of any abnormality in their eyes.
Figure 11B:
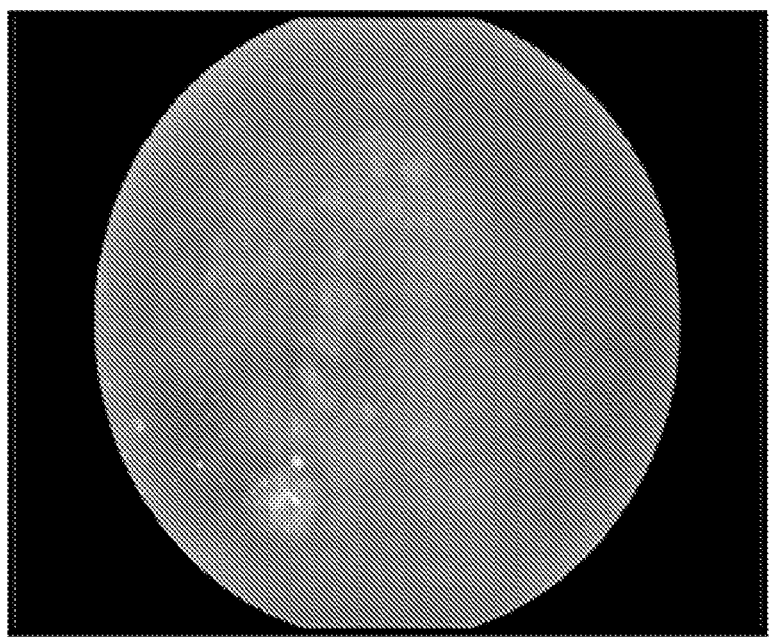
Figure 12A:
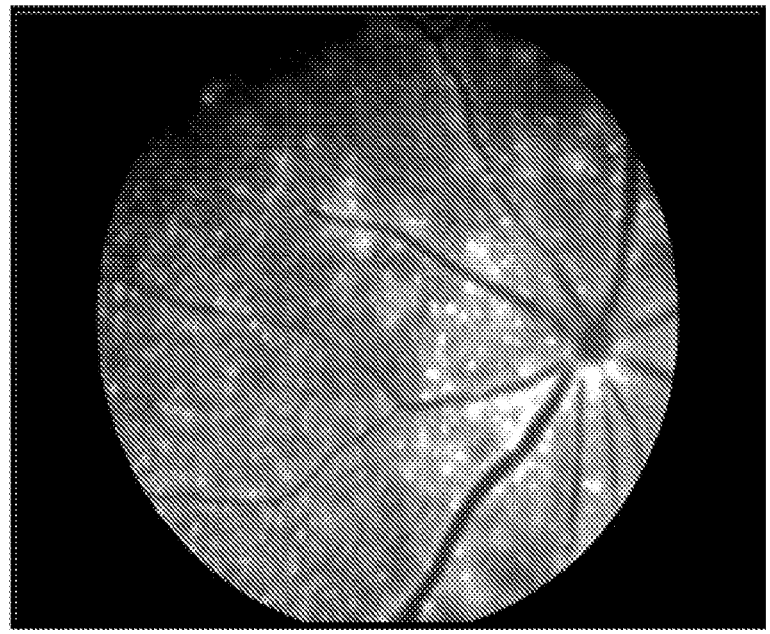
FIGS. 12A and 12B are two photographs showing fluorescence fundus evaluation at month after AAV vector injection. Mice were injected intravitreally with $3 \times 10^{\wedge 9}$ vector genomes of AAV2QUAD/smCBA-GFP (left eye, 12A) and AAV2QUAD/smCBA-sGFP-TatNrf2mer (right eye, 12B). One month after the vector injection, mice were evaluated by fluorescence fundoscopy to determine the presence of GFP in their eyes. The diffuse pattern of fluorescence observed in the eyes treated with the AAV2QUAD/smCBA-sGFP-TatNrf2mer suggest the secretion of the TatNrf2mer peptide.
Figure 12B:
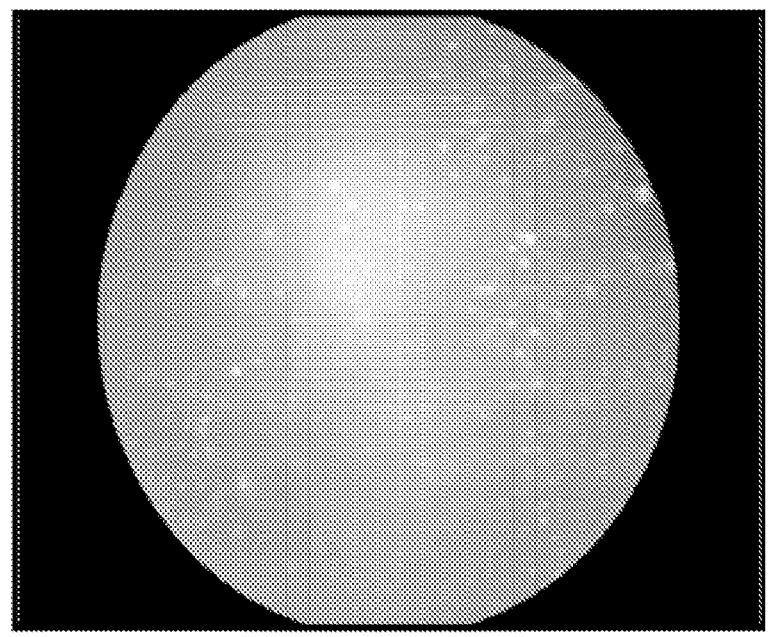
Figure 13A:
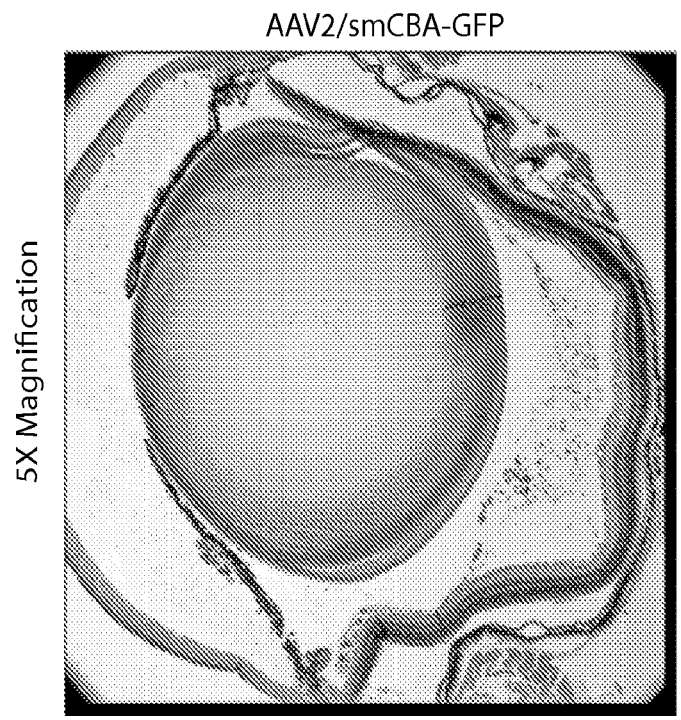
FIGS. 13A and B are two photographs showing histological evaluation of LPS-induced inflammation in the vitreous body. Mice previously injected with both AAV vectors received an intravitreal injection of 25 ng of lipopolysaccharide (LPS) in both eyes. After 24 hrs, mice were sacrificed and their eyes harvested and fixed in 4% paraformaldehyde. Eyes were embedded in paraffin and step section through the cornea-optic nerve axis were collected and stained with hematoxylin and eosin. Infiltrative cells in the vitreous body were counted.
Figure 13B:
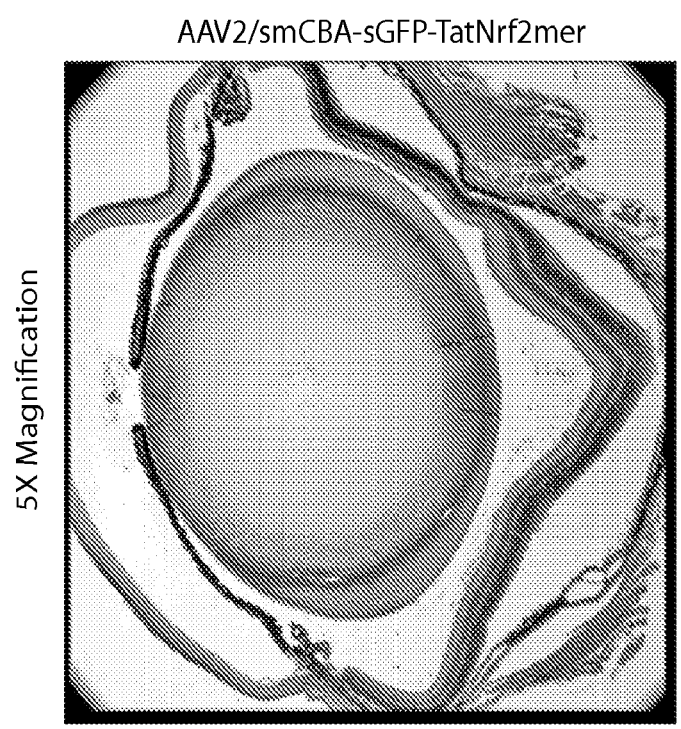
Figure 14:
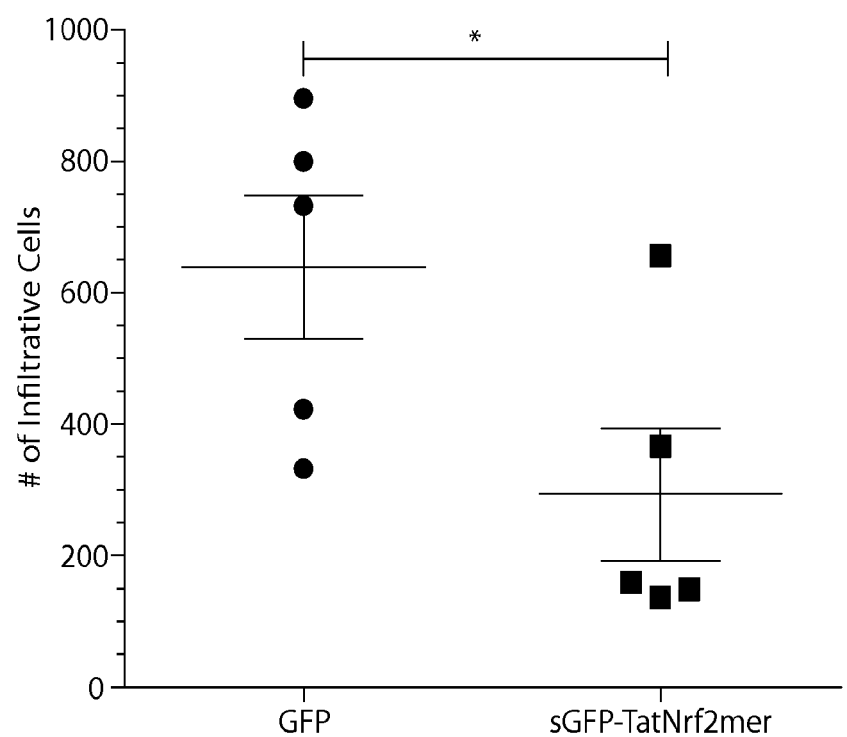
FIG. 14 is a graph showing that the expression of exemplary TatNrf2mer decreases the inflammatory response in the EIU mouse model. Infiltrative cells in the vitreous body were quantified. Individual dots represent mice eyes. Bars represent the Average±SEM. Samples were compared by Student's t-test for paired data. (p=0.03, n=5 mice).
Figure 15A:
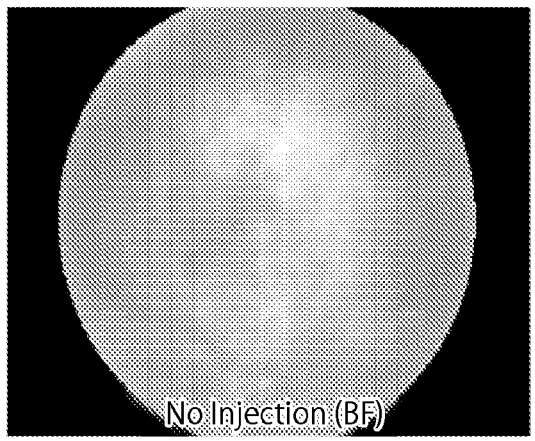
FIGS. 15A-F are six photographs showing In vivo expression of secretable GFP (sGFP) fused to the exemplary TatNrf2mer. C57BL6J mice were injected intravitreally with 3×10^9 vector genomes per eye delivering either GFP or sGFP-TatNrf2mer. One month after vector injection, gene expression was determined by fluorescent fundoscopy (F). As a control, a non-injected mouse was also screened by fluorescent fundoscopy. Mice injected with the GFP vector had a distinct expression of fluorescence; however, mice injected with the sGFP-TatNrf2mer vector showed a diffused pattern of fluorescence that is not observed in the uninjected eye. Top images show the bright field (BF) fundus images of the same eyes.
Figure 15B:
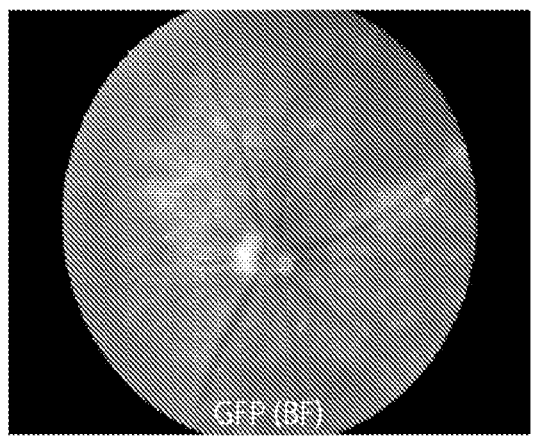
Figure 15C:
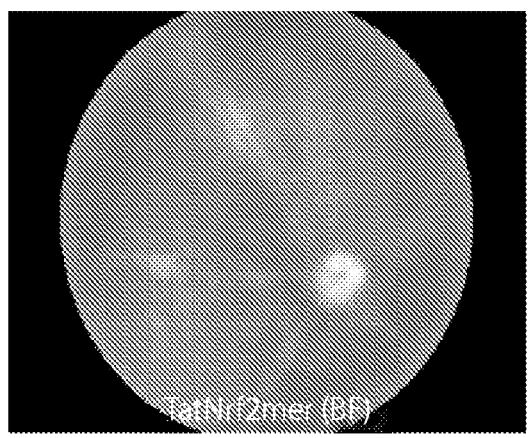
Figure 15D:
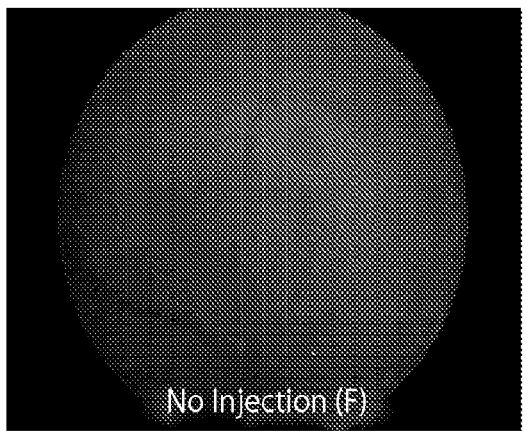
Figure 15E:
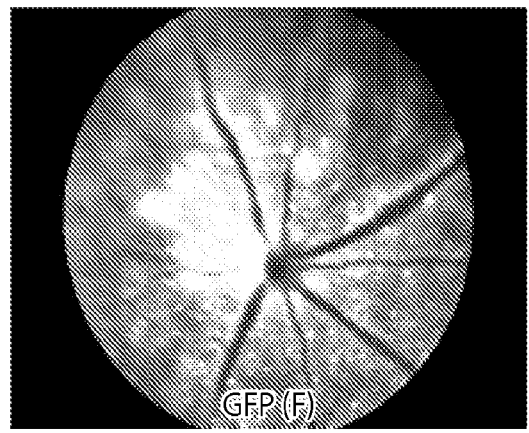
Figure 15F:
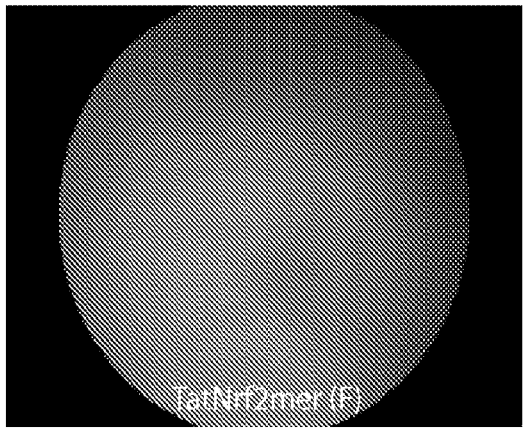

FIGS. 1-18 show a number of examples demonstrating the efficacy of various embodiments described herein. The data from FIGS. 1-18 is summarized as follows. The construct used in the study was an expression cassette containing secretable GFP fused to a TatNrf2-14mer (FIGS. 1 and 2), which was shown to be detectable in cells transfected with the construct (FIG. 3). It was found that human retinal pigment epithelial cells treated with the TatNrf2 plasmid produced 18 fold more GSTM1 mRNA (an antioxidant enzyme and marker of the ARE response) than untreated cells (FIG. 4). Cells treated with the plasmid also produced less oxidized protein (FIG. 5) and remained more viable (FIG. 6) than control cells following treatment with hydrogen peroxide. Stable expression of TatNrf2mer via lentiviral delivery increased the levels of Nqo1 mRNA (an ARE-regulated gene) in ARPE-19 cells (FIG. 7). HEK293T cells transiently expressing the same construct also showed increased Nqo1 mRNA levels (FIG. 9). Cells stably expressing the TatNrf2mer also showed lower concentrations of secreted IL-1β after induction with reactive aldehyde 4-hydroxynonenal (4-HNE) (FIG. 8).

Figure 16A:
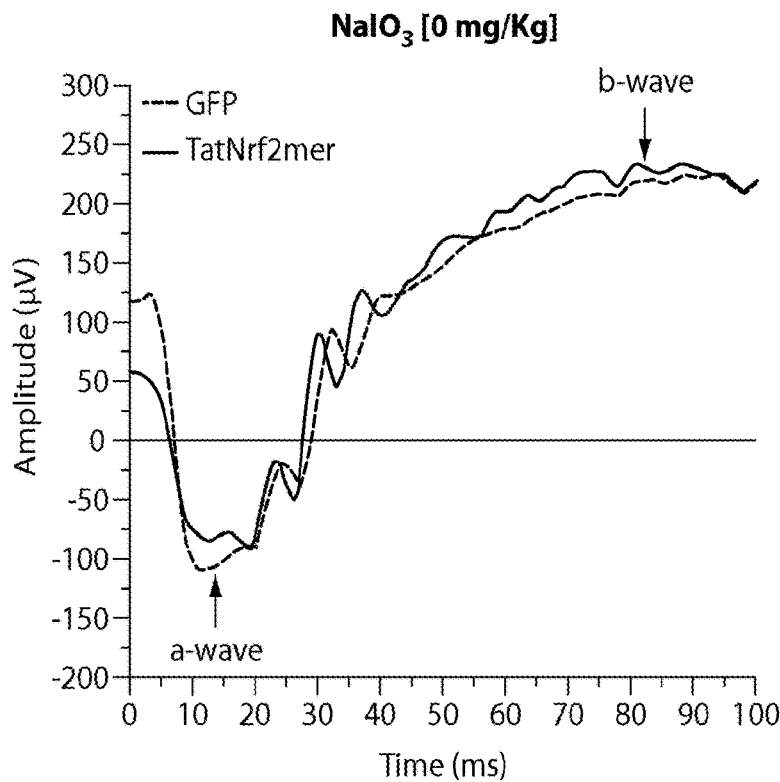
FIGS. 16A and B are two graphs showing the effect of exemplary TatNrf2mer AAV vector on retina electrophysiology in the absence or presence of NaIO3. C57BL6J mice injected intravitreally with 3×10^9 vector genomes per eye of either GFP (left eye) or sGFP-TatNrf2mer (TatNrf2mer, right eye) vector. After one month, mice were injected intraperitoneally with either phosphate buffer saline (NaIO3 0 mg/kg) or NaIO3 in PBS (35 mg/kg). Seven days after these injections, mice were evaluated by electroretinogram (ERG). Mice that did not receive NaIO3 (left graph, FIG. 16A) showed no difference in their a-wave response from photoreceptor cells or b-wave response from bipolar cells of the retina, thus suggesting that the expression of TatNrf2mer in the retina does not affect the ERG response in the absence of injury. However, injection of NaIO3 obliterated both the a-wave and b-wave response in the eye treated with GFP vector while it only dampened these responses in the eye treated with the TatNrf2mer vector (right, FIG. 16B). These are representative ERG responses from a single mouse of each dose of NaIO3.
Figure 16B:
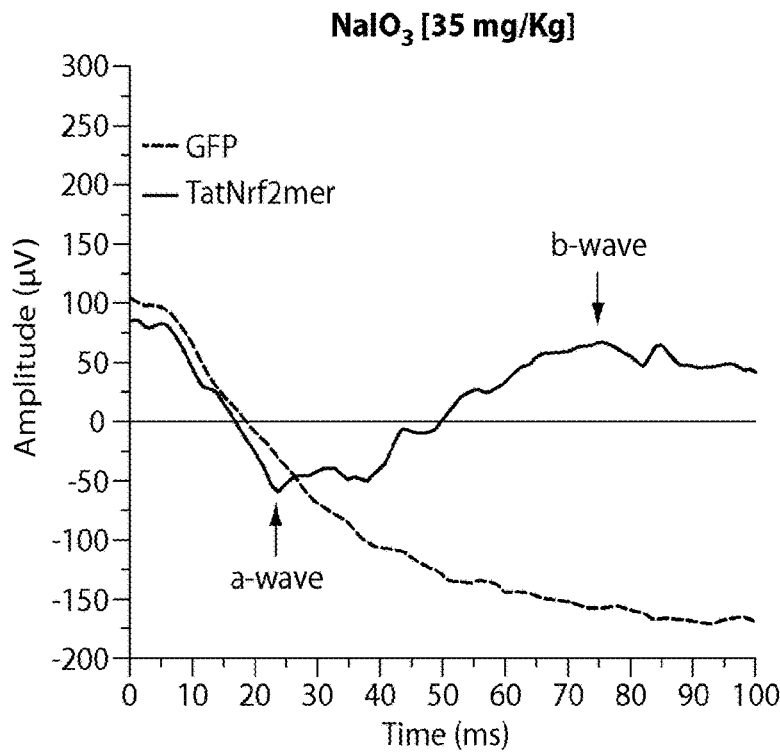
Figure 17:
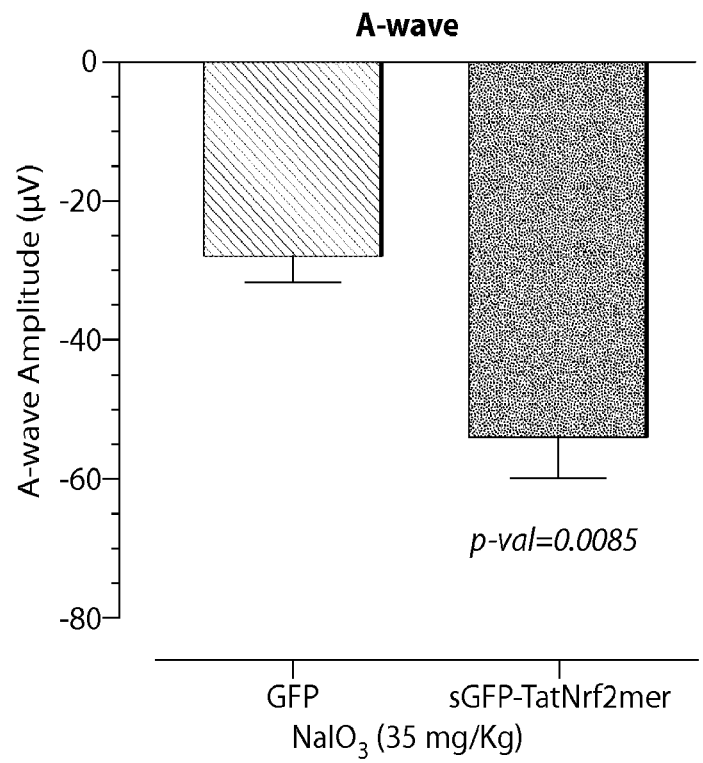
FIG. 17 is a graph showing exemplary TatNrf2mer rescue of a-wave function. The TatNrf2mer AAV vector rescues the a-wave function of the electroretinogram in mice injected with NaIO3. C57BL6J mice were injected intravitreally with 3×10^9 vg of either AAV2QUAD T-F/smCBA-sGFP-TatNrf2mer (right eyes) or AAVQUAD T-F/smCBA-GFP (left eyes). One month later, mice were injected intraperitoneally with NaIO3 (35 mg/Kg). A week after NaIO3 injection, mice were evaluated by full-field ERG. Average a-wave amplitudes were compared by paired-Student's t-test. (n=4 mice, error bars represent SEM).
Figure 18:
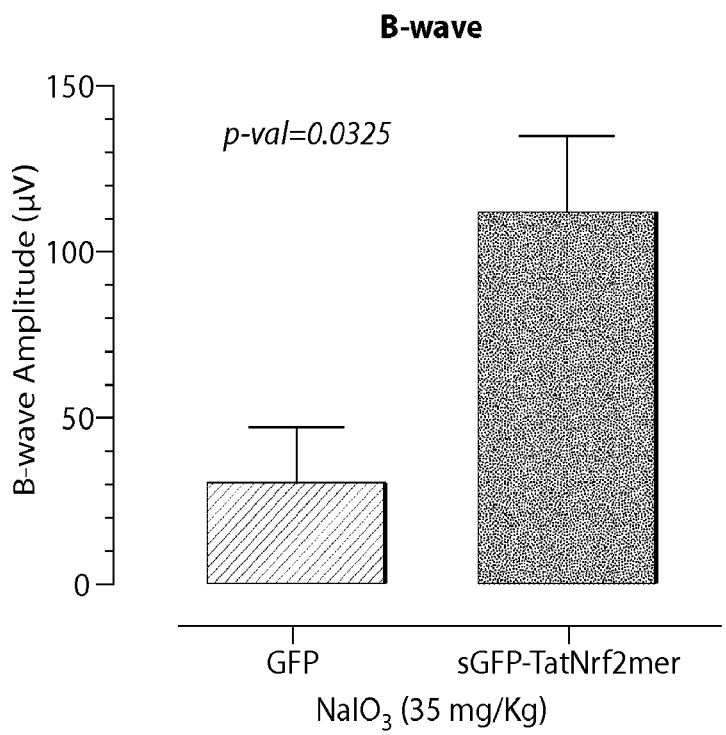
FIG. 18 is a graph showing exemplary TatNrf2mer rescue of b-wave function. The TatNrf2mer AAV vector rescues the b-wave function of the electroretinogram in mice injected with NaIO3. C57BL6J mice were injected intravitreally with 3×10^9 vg of either AAV2QUAD T-F/smCBA-sGFP-TatNrf2mer (right eyes) or AAVQUAD T-F/smCBA-GFP (left eyes). One month later, mice were injected intraperitoneally with NaIO3 (35 mg/Kg). A week after NaIO3 injection, mice were evaluated by ERG. Average b-wave amplitudes were compared by paired-Student's t-test. (n=4, error bars represent SEM).

The construct was then studied in vivo using an AAV delivery system. A mouse model of endotoxin-induced uveitis (EIU) treated intravitreally with rAAV2QUAD/smCBA-sGFP-TatNrf2mer had significantly lower number of infiltrative cells in the vitreous body when compared to its control GFP treated eye (FIGS. 10-14). Secretable GFP was also detected as a diffuse pattern in the eye of mice injected with the construct, confirming that the construct was being properly secreted (FIGS. 15A-F). The effect of the TatNrf2mer AAV vector on retina electrophysiology was then tested in the absence or presence of NaIO3. Mice that did not receive NaIO3 showed no difference in their a-wave response from photoreceptor cells or b-wave response from bipolar cells of the retina, thus suggesting that the expression of TatNrf2mer in the retina did not affect the ERG response in the absence of injury (FIG. 16A). However, injection of NaIO3 obliterated both the a-wave and b-wave response in the eye treated with control GFP vector while it only dampened these responses in the eye treated with the TatNrf2mer vector (FIG. 16B). Upon further study, it was found that the TatNrf2mer AAV vector rescued both the a-wave and b-wave function in mice injected with NaIO3 (FIGS. 17 and 18).

These data show that the secretable TatNrf2mer was expressed and functional both in vitro and in vivo and that the construct was able to combat oxidative stress in vitro and in vivo.

Provided below are protocols related to the experiments represented in FIGS. 1-18.

Materials and Methods

Cell Culture

The HEK293T cell line was grown in Dulbecco's Modified Eagle's Medium (DMEM) supplemented with 10% fetal bovine serum (FBS) and 1% penicillin-streptomycin (Pen-Strep) solution. The ARPE-19 cell line was grown in DMEM/F12 (50/50) media supplemented with 10% FBS and 1% Pen-Strep. All the cell cultures were maintained in an incubator at 37° C. with 5% $CO_2$. All stable cell lines generated by lentiviral vector transduction were grown in the corresponding media supplemented with puromycin at a dose of 1 µg/mL.

Design and Cloning the TatNrf2-14Mer Sequence into the pCDH-EF1-MCS-T2A-puroR Lentiviral Vector Plasmid The Nrf2 sequence that interacts with the Keap-1 protein has been reported to have the following amino acid sequence: LQLDEETGEFLPIQ (SEQ ID NO: 1). This sequence was fused downstream to the HIV Tat-peptide sequence (RKKRRQRRR) (SEQ ID NO: 25) to provide the Nrf2 peptide (Nrf2mer) with cell-penetration properties. The complete amino acid sequence of the TatNrf2mer gene is as follow: RKKRRQRRRLQLDEETGEFLPIQ (SEQ ID NO: 131). Codons were selected and optimized for expression in mammalian cells using the JCat software (Grote et al. 2005). The following DNA oligomers were synthesized:

(1)

(SEQ ID NO: 132)

tatGAATTCgccaccatgaggaagaagaggaggcagag<u>GAGGAGGC TGCAGCTGGACGAG</u>;

(2)

(SEQ ID NO: 133)

ataGCGGCCGCctggatgggcaggaactcgccggtctc<u>CTCGTCCA GCTGCAGCCTCCTC</u>

The uppercase and underlined sequence of these oligos represent the complementary sequences which has a Tm of 65° C., while the uppercase and bold sequence represents the EcoRI (1) and NotI (2) restriction sites. These oligos were mixed and the single stranded sequences were filled with by Klenow fragment of DNA polymerase. A reaction mixture of 5 µg of each oligo, 2 µL of NEB buffer 2 (10×), 1 µL of dNTPs mix (10 mM each), and 6 µL of deionized $H_2O$. The hybridization of the oligos was achieved using the following conditions: Three cycles of 94° C. for 30 seconds, and 60° C. for 30 seconds. The reaction was cool down to 15° C. and 1 µL of Klenow fragment (5 U/µL) was added to the reaction which was incubated at room temperature for 15 minutes. The reaction was stopped by adding 1 µL of 210 mM EDTA and incubating at 72° C. for 20 minutes. This product was purified with the GenElute PCR clean-up kit (Sigma-Aldrich, St Louis, Mo.). The purified fragment and the pCDH-EF1-MCS-T2A-puroR plasmid (Systems Biosciences, Mountain View, Calif.) were digested with EcoRI and NotI for 2 hours at 37° C. and then purified as done previously. The digested products were ligated using the T4 ligase (New England Biolabs, Ipswich, Mass.) by incubating at room temperature for 2 hours. Ligation reactions were transformed into DH5α (Invitrogen, Grand Island, N.Y.).

Viral Vectors

All the lentiviral vectors were created using the pCDH-EF1-MCS-T2A-Puro plasmid (Systems Biosciences, Mountain View Calif.). The transgenes were clones using the EcoRI and the NotI restriction sites in the multiple cloning sites. Plasmids were grown in DH5α cells and sequenced by the Sanger method. To generate viral particles, the plasmids were co-transfected with the pPACKH1 lentivector packaging kit (Systems Biosciences, Mountain View Calif.) into HEK293T cells. The lentiviral vector containing media were harvested at 48 hours after the co-transfection and were centrifuged at 3,000 rpm for 5 minutes at 4° C. These vector containing media were filter using a 0.22 µm syringe filter.

Enzyme Linked Immunosorbent Assay (ELISA)

Medium was harvested from the indicated cultures and 100 µL were used to quantify IL-1β concentration. The ELISA kit for the human IL-1β was purchased from RayBiotech (Norcross, Ga.). The concentration of IL-1β was determined as per manufacturer's protocol.

Western Blot

The corresponding cells were lysed in NP-40 lysis buffer supplemented with Protease Inhibitors Cocktail (Thermo Fisher Scientific, Rockford Ill.) and 2 mM EDTA. The protein concentration of the samples was measured with the DC Protein Assay (Bio-Rad, Hercules Calif.) as per manufacturer's protocol. Protein lysates were diluted in Laemlli sample buffer containing 100 µM DTT and boiled for 5 minutes. Equal amounts of protein were separated by SDS polyacrylamide gel electrophoresis and transferred into a PVDF membrane using the iBlot system (Invitrogen, Grand Island, N.Y.) as per manufacturers' protocol. This membrane was blocked with a proprietary blocking buffer from Li-Cor (Li-Cor Biosciences, Lincoln, Nebr.) for 1 hour at room temperature and incubated overnight with the designated primary antibody at 4° C.

Endotoxin-Induced Uveitis (EIU) Mouse Model

Mice of the C57B/6 strain were injected intravitreally with the $3\times10^9$ vector genomes in each eye. One month after the injection GFP expression was observed by fluorescent fundoscopy. The next day mice were injected intravitreally in each eye with 25 ng of LPS. After 24, these mice were sacrificed and their eyes were enucleated and placed in 4% paraformaldehyde at 4° C. overnight. Eyes were embedded in paraffin were sectioned through the cornea-optic nerve axis with a thickness of 12 µm. The sections were collected in independent slides with sections on the same slide having a difference of 96 µm. Slides were stained with hematoxylin and eosin to visualize infiltrating cells. These cells were quantified, in images of the sections, by two independent individuals.

Sodium Iodate Mouse Model of RPE Damage

One month old C57BL/6J mice were injected intravitreally with $3\times10^9$ vector genomes of AAV vector delivering either GFP (left eye) or sGFP-TatNrf2mer (right eye). One month later mice were evaluated for gene expression using fluorescent fundoscopy. One week later mice were injected intraperitoneally with 35 mg/Kg of sodium iodate $NaIO_3$. One week afterwards, retina function was evaluated by ERG.

Electroretinography (ERG)

Scotopic ERG analysis was used to measure the loss of rod function according to previously described methods (Justilien et al., 2007; Mao et al., 2011). Mice were dark-adapted by placing them in a dark room overnight. The day of the assay the eyes were dilated with drops of 1% atropine and 10% phenylephrine solutions. Mice were then anesthetized with a solution of ketamine and xylazine. Electrodes were placed over the corneas of an anesthetized mouse, while two reference electrodes were placed in the mouth and tail respectively. While in a dark dome, mice were visually stimulated with dim flashes of light and the voltage changes occurring in their eyes are recorded as a function of time. The value of the a-wave was measured from 0 µV reference to the peak of the negative projected wave, while the b-wave was measured from the 0 µV reference to the peak of the positively projected wave.

Retina Funduscopy

Digital fundus imaging was performed with a Micron III retinal imaging microscope (Phoenix Research Laboratories, Pleasaton, Calif.) to monitor gene expression. Conscious mice had their eyes dilated with 1% atropine and 10% phenylephrine. Mice were then anesthetized with a mixture of ketamine and xylazine in normal saline. To avoid loss of moisture from the ocular surface during the procedure mice received a drop of 2.5% hypermellose ophthalmic demulcent solution (Gonak, AKORN, Lake Forest, Ill.). Bright field fundus image was acquired using the same exposition time. Using the fluorescein filters GFP fluorescence was measured using the same exposure time for all the eyes.

Transfection

Cells were plated at $8\times10^5$ cells per well in a 6-well plate with complete growth media and incubated for 24 hours. The next day complete growth medium was replaced in each well with 2 mL of serum and antibiotics free medium. Plasmid DNA complexes were generated by diluting 4 µg of the corresponding DNA in 100 µL of sterile PBS 1× and 10 µg of a 1 µg/µL of polyethyleneimine (PEI) in 100 µL of PBS 1×. Dilutions were incubated at room temperature for 5 minutes. DNA:PEI complexes were made by mixing the diluted DNA and PEI and incubating them for 20 minutes at room temperature. Complexes were overlay on the cells drop wise and cells were maintained at 37° C. for 18 hours. The transfection was stopped by removing the complex containing medium and replacing it with 3 mL of complete growth medium. Cells were grown for another 24 hours at 37° C. Afterwards, cells were harvested by trypsinization.

RNA Isolation

Total RNA was isolated from cell cultures using the RNeasy mini kit (QIAGEN, Valencia, Calif.) as per manufacturers' protocol. RNA was quantified by 260 nm absorbance and quality was verified by running an aliquot in a 1% agarose gel.

cDNA Synthesis cDNA was synthesize with the iScript cDNA synthesis kit (Bio-Rad). Briefly, 1 ng of total RNA (10 µL) was mixed with 4 µL of 5× iScript reaction mix, 5 µL of RNAse free water, and 1 µL of iScript reverse transcriptase. The following temperatures and times were used in the synthesis of the cDNA: 25° C. for 5 minutes, 42° for 30 minutes, and 85° C. for 5 minutes. cDNA was stored at −20° C. until needed.

Polymerase Chain Reaction (PCR) for the Detection of TatNrf2mer Expression

A PCR reaction was prepared using 1 uL of cDNA library made from total RNA isolated from wild type ARPE-19 cells or ARPE-19 cells expressing either puromycin resistance (puroR) gene only (control) or TatNrf2mer and the Taq polymerase using the 2× Taq Master Mix. The following primers binding to either the Tat region sequence or the puroR were used:

```
Tat F-
                                     (SEQ ID NO: 134)
AGT TCT TGC AGC TCG GTG
(Tm 55° C.)

PuroR R-
                                     (SEQ ID NO: 135)
TCG CCA CCA TGA GGA AG
(Tm 56° C.)
```

To amplify the desired sequence the following thermal condition was used: 93° C. for 3 minutes, 30 cycles of 93° C. for 30 seconds, 55° C. for 30 seconds, and 72° C. for 20 seconds, followed by 72° C. for 10 minutes. PCR products were separated in a 1.3% agarose gel.

Real-Time PCR (RT-PCR) for ARE Genes

The RT-PCR for both GSTM1 and NqO1 was performed using the SsoFast EvaGreen Supermix kit (Bio-Rad, Hercules Calif.). The following primers were used to detect the corresponding gene:

```
NqO1-F:
                                     (SEQ ID NO: 136)
AAAGGACCCTTCCGGAGTAA

NqO1-R:
                                     (SEQ ID NO: 137)
CCATCCTTCCAGGATTTGAA

GSTM1-F:
                                     (SEQ ID NO: 138)
CTACCTTGCCCGAAAGCAC

GSTM1-R:
                                     (SEQ ID NO: 139)
ATGTCTGCACGGATCCTCTC

GAPDH-F:
                                     (SEQ ID NO: 140)
ACAGTCCATGCCATCACTGCC
```

-continued

GAPDH-R:
GCCTGCTTCACCACCTTCTTG (SEQ ID NO: 141)

β-actin-F:
AGCGAGCATCCCCCAAAGTT (SEQ ID NO: 142)

β-actin-R:
GGGCACGAAGGCTCATCATT (SEQ ID NO: 143)

PCR reaction mixtures for each gene to be measured was prepared by adding 1 µL of a 1:10 dilution of cDNA library, 1 µL of F primer (5 µM) and 1 µL of R primer (5 µM), 5 µL of 2× SsoFast EvaGreen supermix, and 2 µL of dH$_2$O. Simultaneous amplification of all genes was done using the following conditions: 95° C. for 3 minutes, followed by 40 cycles of 95° C. for 10 seconds and 60° C. for 20 seconds. Fluorescence was measured at the end of each cycle by using the Bio-Rad CFX96 thermocycler. Fold changes in gene expression were determined by the ΔΔCt method.

Mil Assay

Cell were plated in a 96-well plate at 8×10$^4$ cells per well in 100 µL of complete growth media and were incubated overnight at 37° C. The next day, media was removed and cells were washed once with 100 µL of PBS 1×. Cells were then exposed to 200 µL of serum and antibiotic free medium containing 800 µM of H$_2$O$_2$. The cells were then incubated at 37° C. for six hours. After this incubation, cells were washed once with PBS 1× as done previously. Cells were then incubated with 200 µL of MTT (3-(4,5-dimethylthiazol-2-yl)-2,5-diphenyltetrazolium bromide) solution diluted in RPMI-1640 (500 µg/mL) at 37° C. for 4 hours. As a blank 3 wells with no cells but containing 200 µL of MTT were included in the plate. After the 4 hours, the MTT solution was carefully removed and 200 µL of DMSO was added to the wells. The plate was incubated at room temperature for 15 minutes. The absorbance at 570 nm was determined using a plate reader.

Nitrotyrosine Assay

Treated cells were harvested by trypsinization for 5 minutes and centrifugation at 5,000×g for 5 minutes at 4° C. Cell pellets were lysed in RIPA buffer supplemented with 2 µM EDTA and 1× Halts Protease Inhibitors Cocktail (Thermo Scientific, Waltham, Mass.). The concentration of nitrotyrosine in these samples was measured with the Nitrotyrosine ELISA Assay Kit (EMD Millipore, Billerica, Mass.) as per manufacturers' protocol.

Although more than one route can be used to administer a particular compound, a particular route can provide a more immediate and more effective reaction than another route. Accordingly, the described routes of administration are merely exemplary and are in no way limiting.

Example 2. Antioxidant Gene Therapy Vector for the Treatment of Age-Related Macular Degeneration Age-related macular degeneration (AMD) is the most common cause of blindness among the elderly in developed countries. This debilitating disease can be associated with the growth of new blood vessels into the retina (wet AMD) or with the accumulation of subretinal deposits (dry AMD). Although there is an approved therapy for wet AMD, there is no available therapy for dry AMD. The dry AMD form of the disease has been associated with increase oxidative stress within the retina. A potential therapeutic target against oxidative stress is the Nrf2 signaling pathway. This signaling pathway controls the expression of genes which are known to have antioxidant activity. As described herein, a viral vector was developed that delivers a secretable and cell-penetrating peptide that activates Nrf2 signaling. The goal of the present study was to develop a therapeutic agent for dry AMD that can decrease the oxidative stress within the retina. It was hypothesized that by manipulating the Nrf2 signaling pathway using gene therapy, a therapy for this form of AMD could be developed, which could maintain the vision of those affected. Such therapy could significantly improve the quality of life of the patients suffering from this devastating disease.

Introduction

Age related macular degeneration (AMD) is one of the most common causes of blindness affecting the elderly in developed countries (1). Although scientific advances have led to novel treatments for the exudative (wet) form of AMD (2-4) currently there are no treatments available for the much more common dry AMD. Dry AMD has been linked to increased oxidative stress in the retina (5). An increase in oxidative stress in the retina pigmented epithelium (RPE) of the eye and a low grade chronic inflammatory process have both been associated with dry-AMD. Some features of the disease are the accumulation of lipofuscin within the cells of the RPE, accumulation of drusen (protein/lipid deposits beneath the RPE cell layer), the death of RPE cells, and the presence of activated microglia.

The Nrf2 signaling pathway is a cellular mechanism of controlling the levels reactive oxygen species within cells. This transcription factor controls the expression of antioxidant genes such as heme oxygenase 1 (HO-1) or glutathione S-transferase mu 1(GSTM1). However, its activity is tightly regulated by its repressor Keap-1, which, upon binding to Nrf2, induces its proteasomal degradation through ubiquitination(6). The therapeutic value of targeting the Nrf2 signaling pathway has been studied in many diseases associated with increased oxidative stress. Several groups have demonstrated that certain natural compounds can activate this signaling pathway and protect against oxidative stress damage. One of this compounds called sulforaphane is found in certain vegetables and has been demonstrated be protective against liver (7) and brain (8, 9). Other studies have shown that the natural compound resveratrol found in wine can also activate this signaling pathway (10-12). However, the high doses needed to achieve protective effect make their transition into therapeutic agents complicated.

Figure 19:
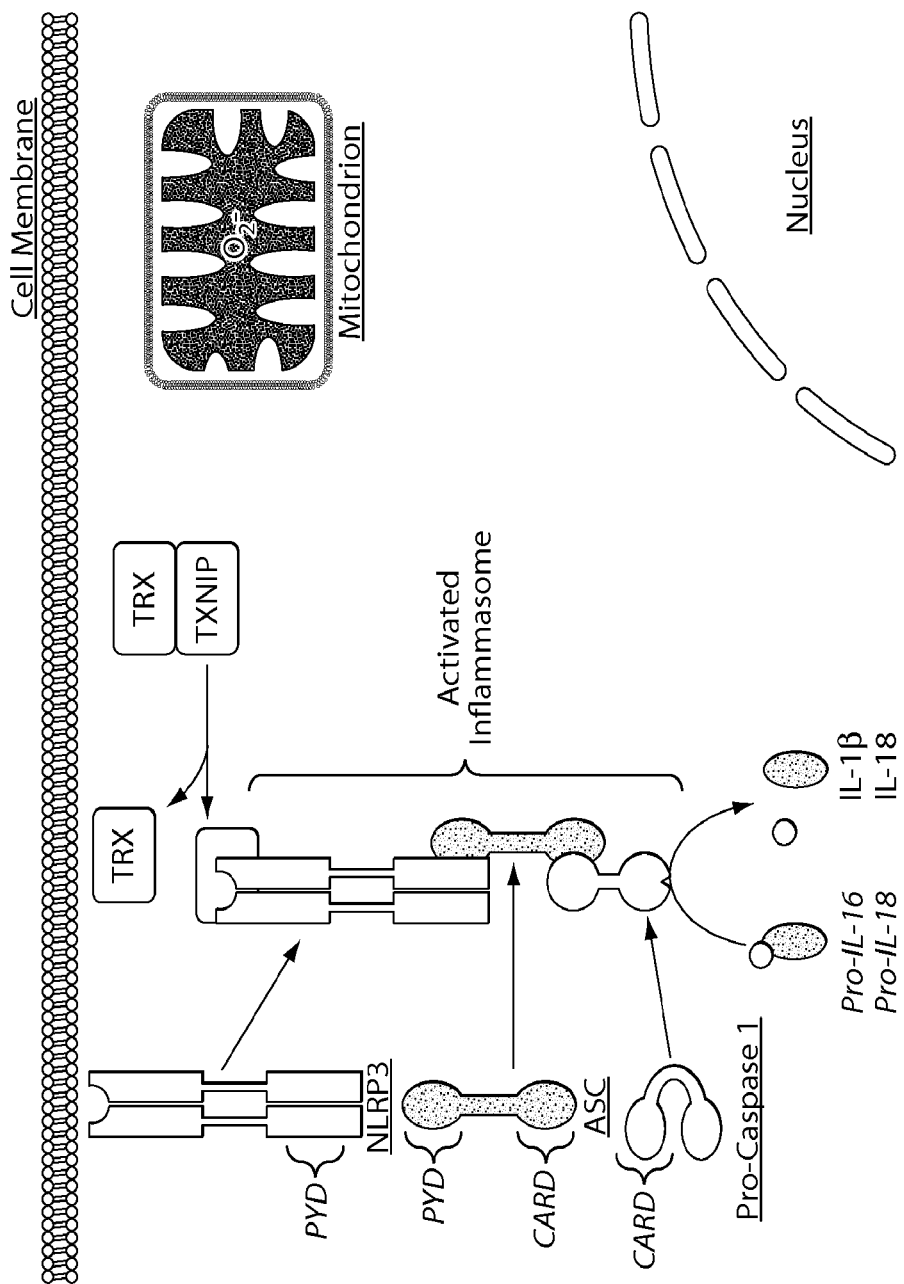
FIG. 19 is a diagram showing exemplary activation of the NLRP3 inflammasome by oxidative stress. Increases in oxidative stress within the cells are sensed by the thioredoxin protein (TRX) which then dissociates from the TRX interacting protein (TXNIP). The free TXNIP can then engage the NLRP3 receptor which then recruits the ASC protein and the pro-caspase-1 forming the active inflammasome complex. Finally, active caspase-1 can proteolyze the pro-forms of the IL-1β and IL-18 which are then secreted from the cell to and start a pro-inflammatory response.

A link between increases in oxidative stress and the activation of the inflammasome has been established (13, 14) (FIG. 19). This inflammasome activation leads to the secretion of the potent pro-inflammatory cytokines interleukin-1 beta (IL-1β) and IL-18 (15-17). The NLRP3 inflammasome has been found to be present in samples from AMD patients (18). Several compounds associated with oxidative stress and AMD such as 4-hydroxynonenal (4-HNE) (19) and carboxyethylpyrrole (CEP) (20) have been shown to activate the inflammasome. The CEP adducts have, for instance, been shown to induce the activation of the inflammasome (21) and activate macrophages (22) when delivered in vivo. These studies strongly suggest that the oxidative stress observed in AMD can be directly linked to the activation of the inflammasome and perhaps to further damage due to inflammation.

The study herein explores the role played by inflammation and oxidative stress in the development and progression of dry-AMD and provides characterization of viral vectors that deliver either anti-inflammatory or antioxidant gene with both secretable and cell penetrating characteristics. This study determined the pathological role that the inflammasome and oxidative stress have in the pathogenesis of AMD, and led to the development of two AAV vectors that are useful for therapy. The study herein showed the feasibility of targeting the inflammasome activity in the retina with a secretable and cell penetrating viral protein or a peptide capable of inducing the expression of antioxidant genes. The study benefits the study of AMD by advancing knowledge of inflammatory processes in the disease. This research will also likely benefit ocular diseases such as uveitis and diabetic retinopathy in which IL-1β mediated inflammatory processes are involved in the disease pathophysiology (23, 24). It is hypothesized that delivery of a TatNrf2mer can interrupt the progression of the retina degeneration. This blockade will prevent RPE demise and inflammatory cell recruitment in the face of oxidative damage to the RPE.

Results

Figure 20:
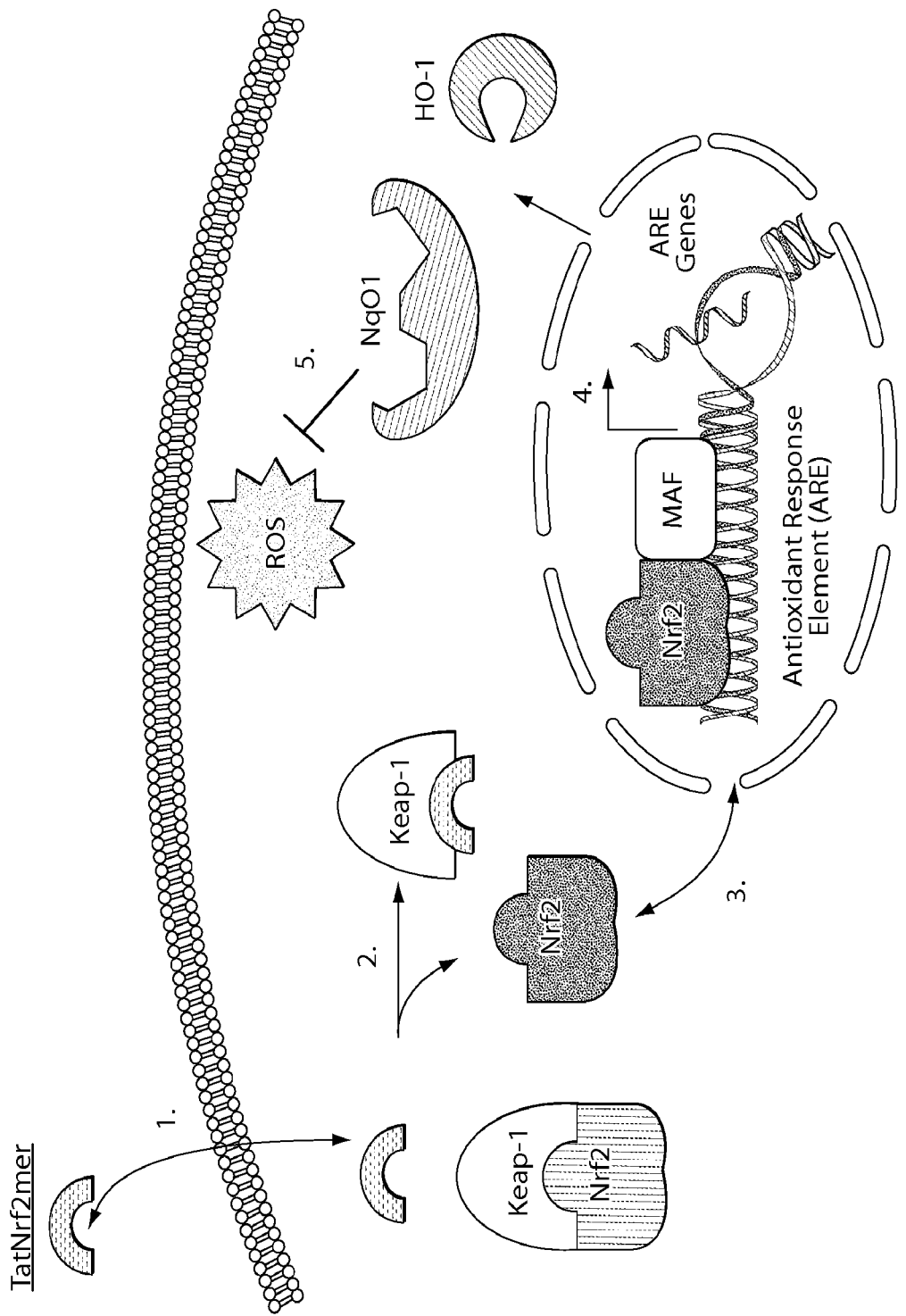
FIG. 20 is a diagram showing an exemplary mechanism of action of TatNrf2mer. The Nrf2mer peptide is derived from the Nrf2 gene domain that binds Keap-1 and penetrates cells when fused to the Tat peptide. The TatNrf2mer binds to Keap-1 liberating Nrf2, which moves to the nucleus and induces the expression of antioxidant genes (i.e. NqO1 and HO-1) which reduce reactive oxygen species.
Figure 21A:
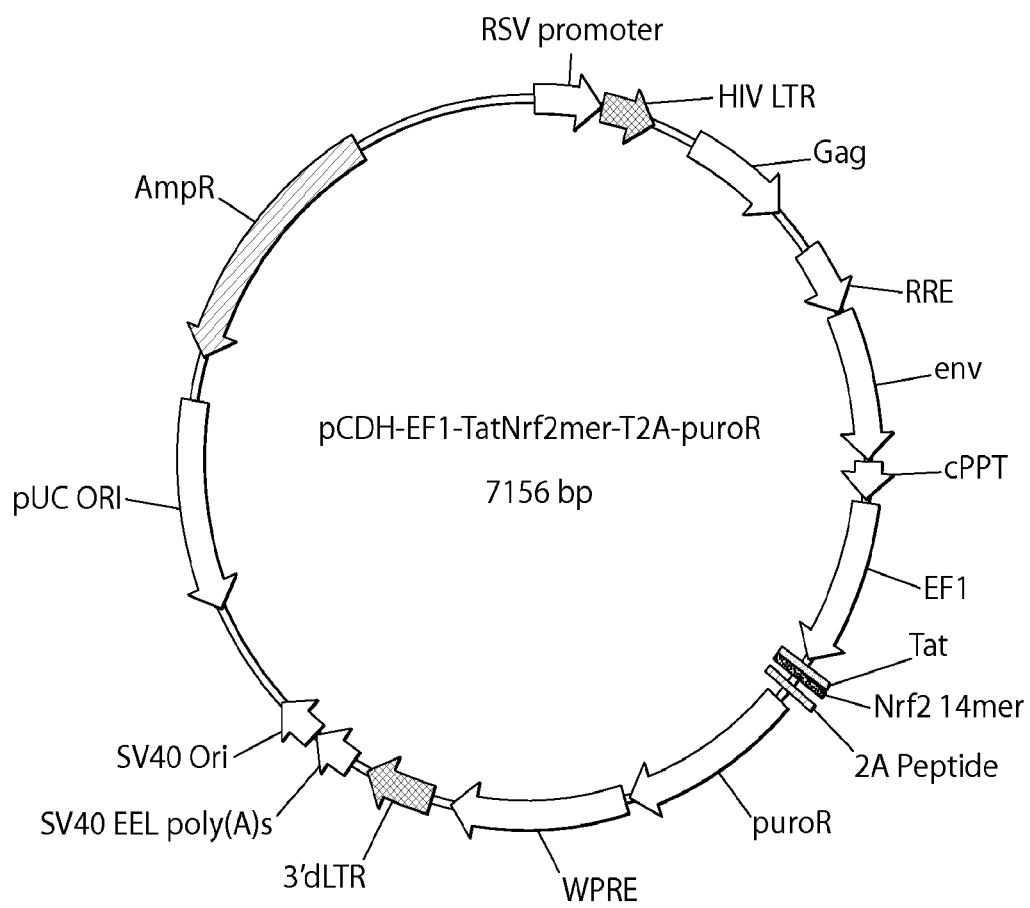
FIGS. 21A-D show that the exemplary TatNrf2mer peptide induces antioxidant genes and protects cells against oxidative stress.
Figure 21B:
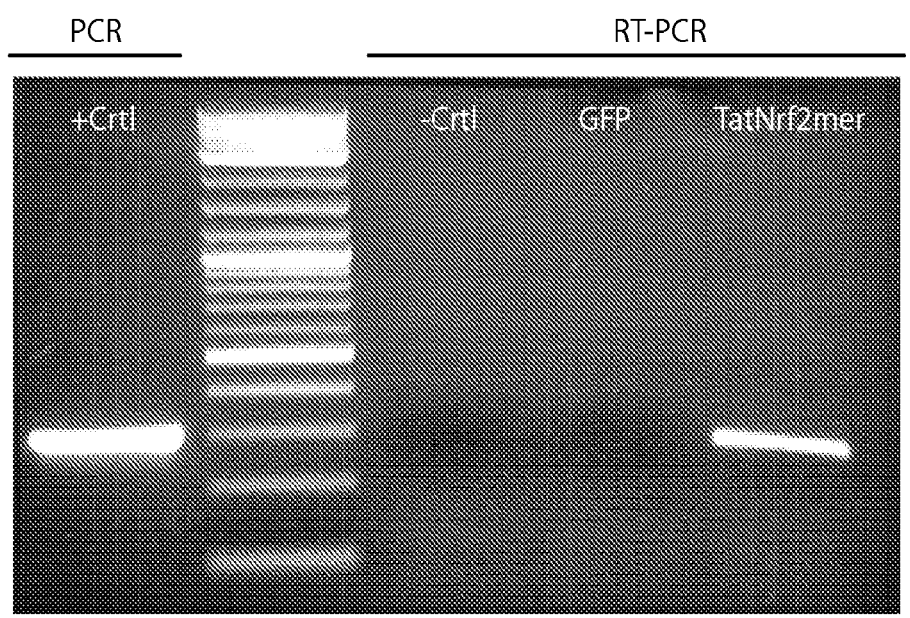
Figure 21C:
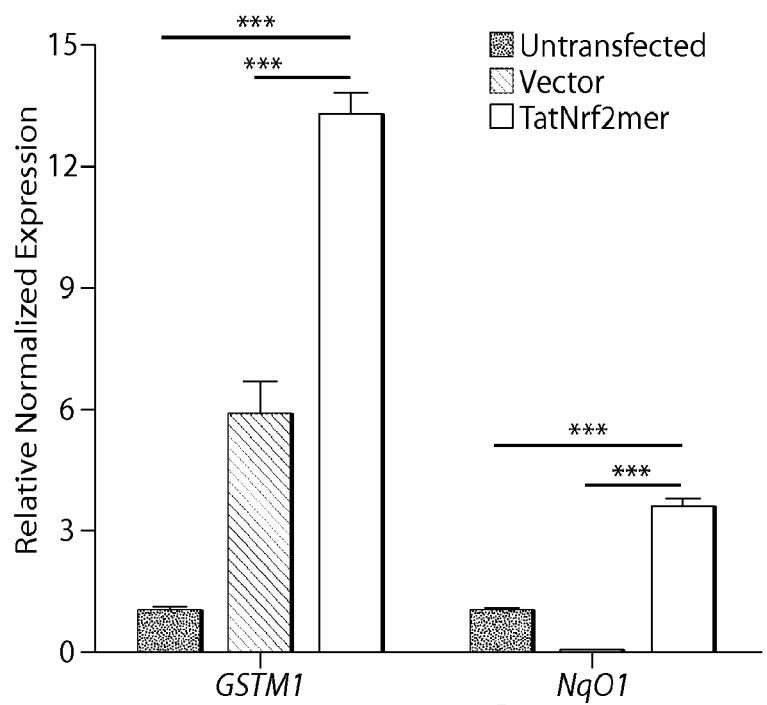
Figure 21D:
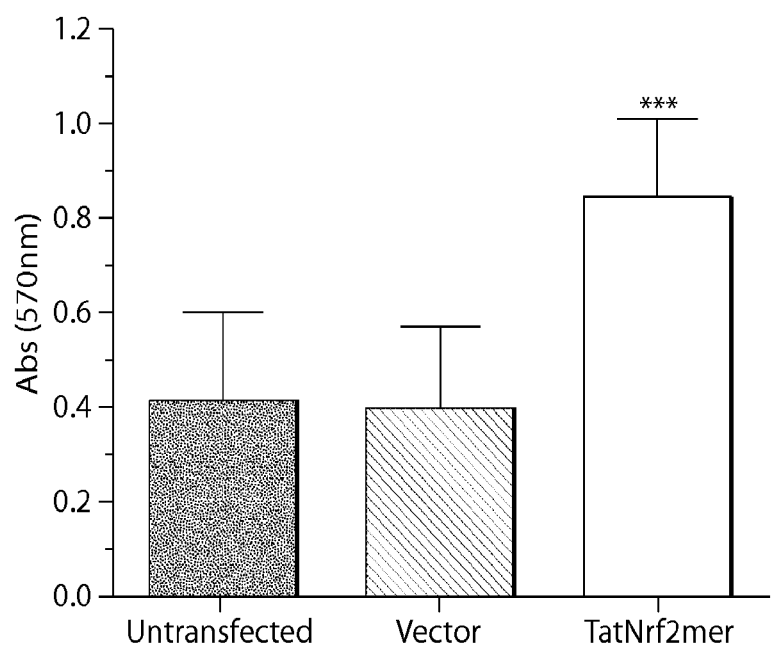

Oxidative stress within the retina is an important driving force for the development of dry-AMD (1,2). It has been reported that an Nrf2 derived peptide can induce the expression of antioxidant genes in vitro (25) (FIG. 20).

Figure 22:
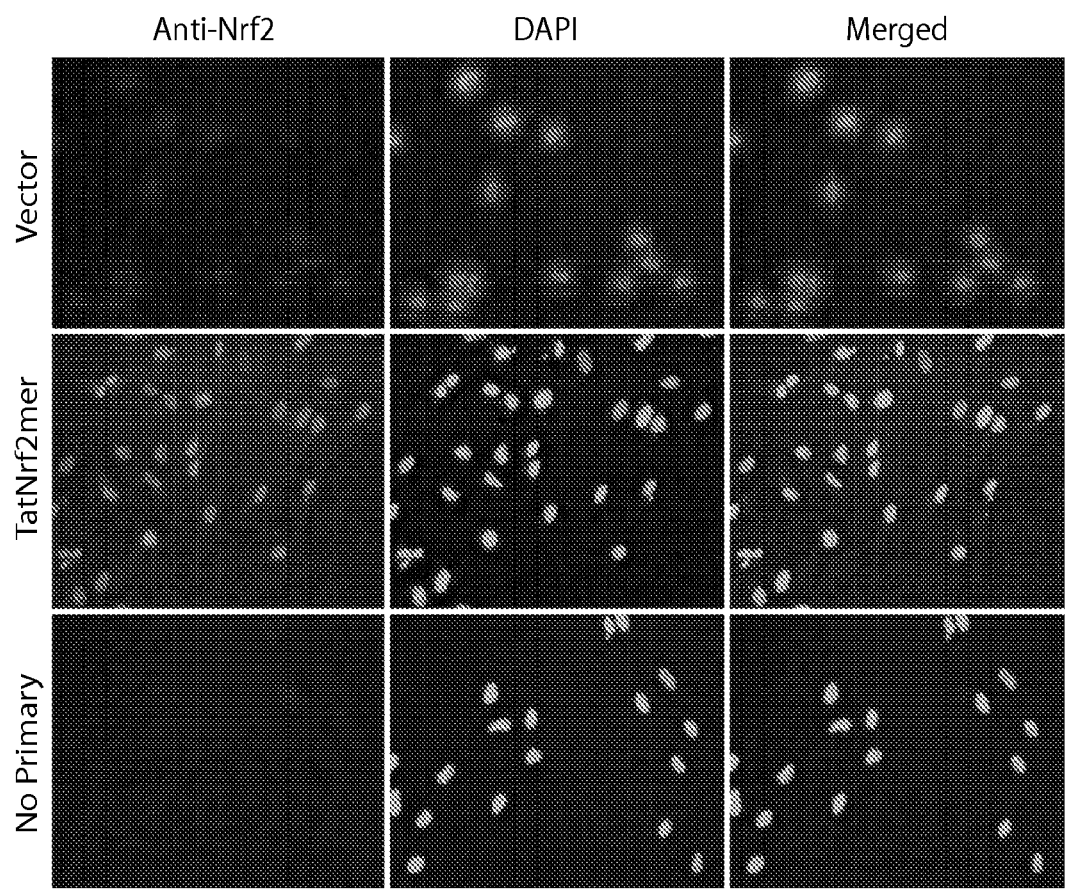
FIG. 22 is a series of photographs that shows expression of the exemplary TatNrf2mer induces the nuclear translocation of endogenous Nrf2 in ARPE-19 cells. ARPE-19 cells were transduced with lentiviral vectors delivering either TatNrf2mer-T2A-PuroR (TatNrf2mer) or T2A-PuroR and selected by the addition of puromycin. Stable cells were stained with an antibody against the Nrf2 protein. Secondary antibody conjugated to Cy3 chromophore (red) was used to detect the presence or absence of the anti-Nrf2 antibody. Nuclear staining with DAPI (blue) was done as a counter stain.

In the study herein, a genetic sequence was developed to deliver this peptide via gene transfer. In cell culture, it was observed that the expression of this TatNrf2mer gene can increase anti-oxidant genes (FIGS. 21A-D). RPE cells stably expressing the TatNrf2mer (Nrf2 peptide linked to the cell penetrating peptide of the HIV tat gene) exhibited increased expression of anti-oxidant genes GSTM1 and Nqo1 and showed increased resistance to peroxide injury. Expression of the TatNrf2mer also induced the nuclear translocation of endogenous Nrf2 in ARPE-19 cells (FIG. 22).

Figure 23A:
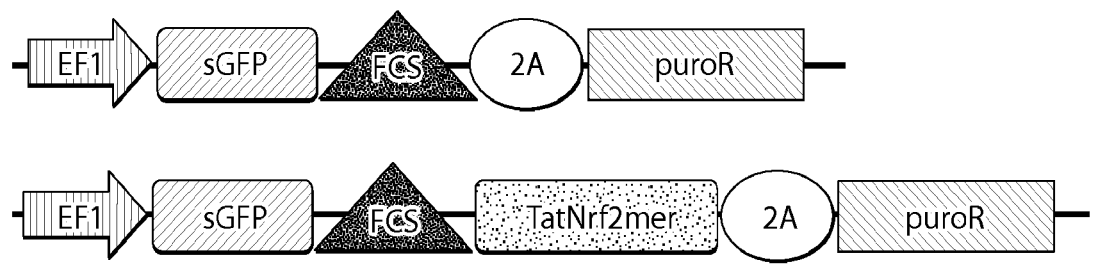
FIGS. 23A-C show that exemplary secretable TatNrf2mer induces the expression of ARE genes.
Figure 23B:
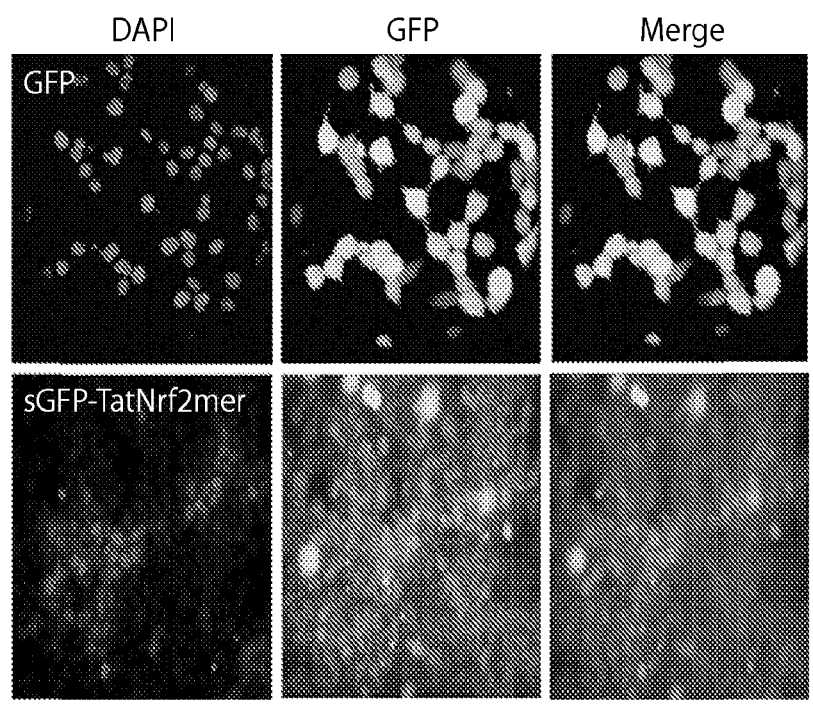
Figure 23C:
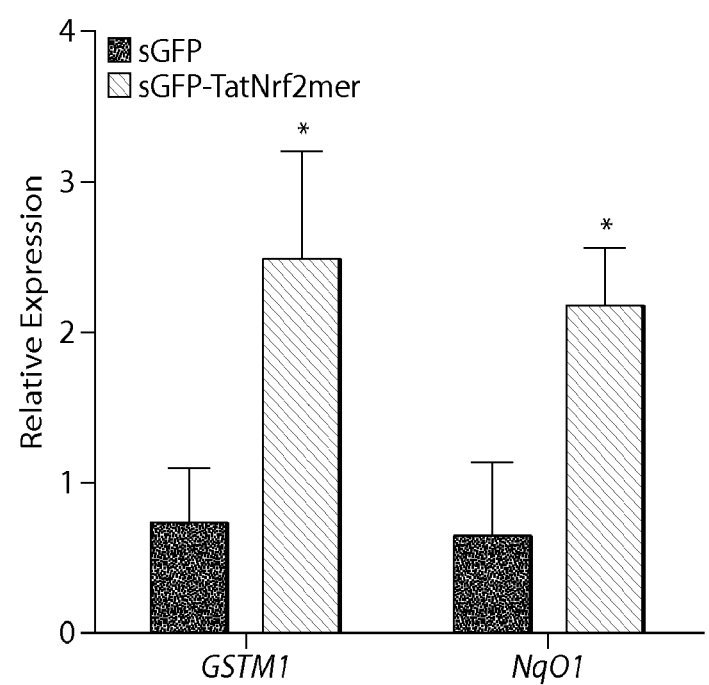

Based on these results, the gene was further modified by fusing it to a GFP (sGFP) rendered secretable by including an Igκ signal upstream of the coding sequence. A furin cleavage site (FCS) was used as a linker region between the sGFP and the TatNrf2mer gene. As a control, a sequence lacking the TatNrf2mer gene was created (FIG. 23A). Using lentiviral vectors, HEK293T cells were created that stably expressed GFP, sGFP-FCS, or sGFP-FCS-TatNrf2mer. Cell lines expressing sGFP-FCS-TatNrf2mer showed a different distribution of GFP when compared with cells expressing GFP (FIG. 23B). When ARPE-19 cells were incubated with the conditioned media from sGFP-FCS or sGFP-FCS-TatNrf2mer cells a significant increase in the expression of the antioxidant genes GSTM1 and NqO1 was observed, indicating that the TatNrf2mer peptide is secreted, penetrates and activates the Nrf2 signaling pathway in other cells (FIG. 23C). This construction provides a considerable advantage to the delivery of the peptide in that gene-delivery of a secreted protein provides continuous delivery of the therapeutic peptide and secretion permits a by-stander effect in which infected cells serve as depot for the production of the Nrf2 peptide.

Figure 24A:
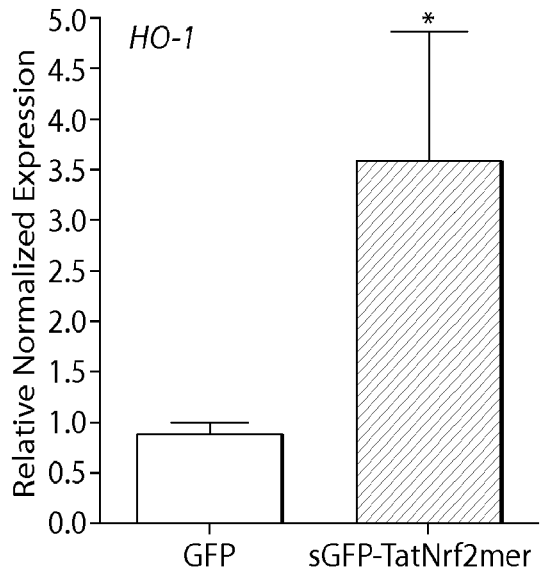
FIGS. 24A-D are a series of graphs that show that gene delivery of the exemplary TatNrf2mer protects the retina from oxidative stress.
Figure 24B:
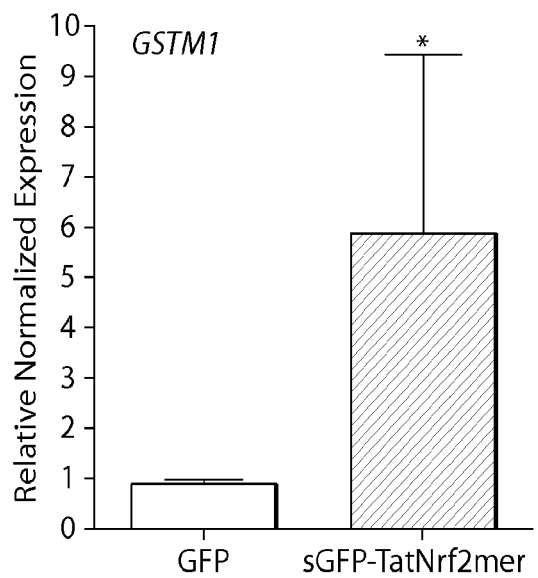
Figure 24C:
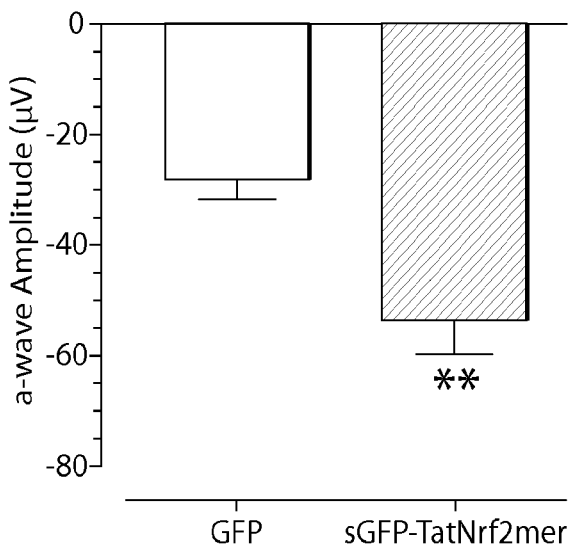
Figure 24D:
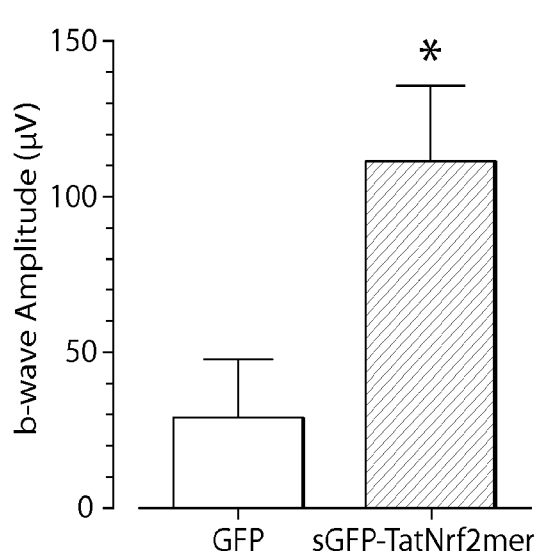

Next, an AAV vector was developed that could deliver a secreted and cell penetrating version of this peptide into the retina. Using the sodium iodate inducible model of the oxidative injury to the RPE (26), an increase in the expression of the ARE genes HO-1 and GSTM1 was observed in eyes treated with the TatNrf2mer AAV vector (FIG. 24A-B). These eyes also showed a partial protection of the ERG a- and b-wave amplitudes, suggesting protection of the photoreceptors and bipolar cells (FIG. 24C-D). These results strongly suggest that the TatNrf2mer vector can modulate the Nrf2 signaling pathway in the retina, and by doing so it can protect it from oxidative stress.

Figure 25A:
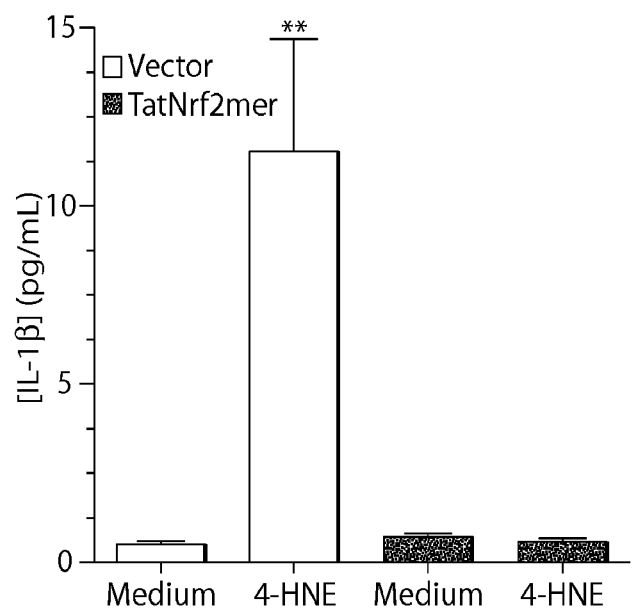
FIGS. 25A-C show that the exemplary secretable TatNrf2mer has anti-inflammatory properties in a mouse model of ocular inflammation.
Figure 25B:
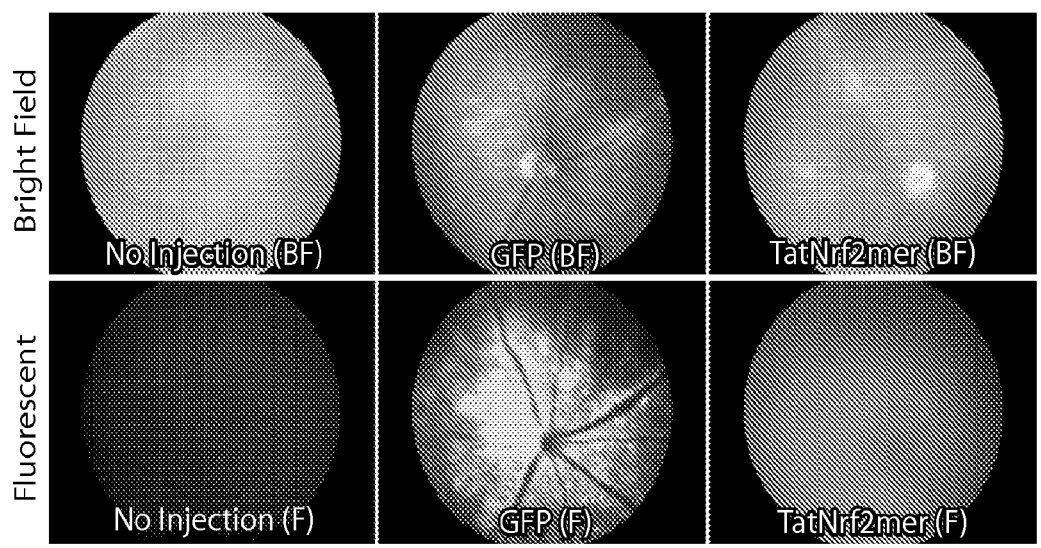
Figure 25C:
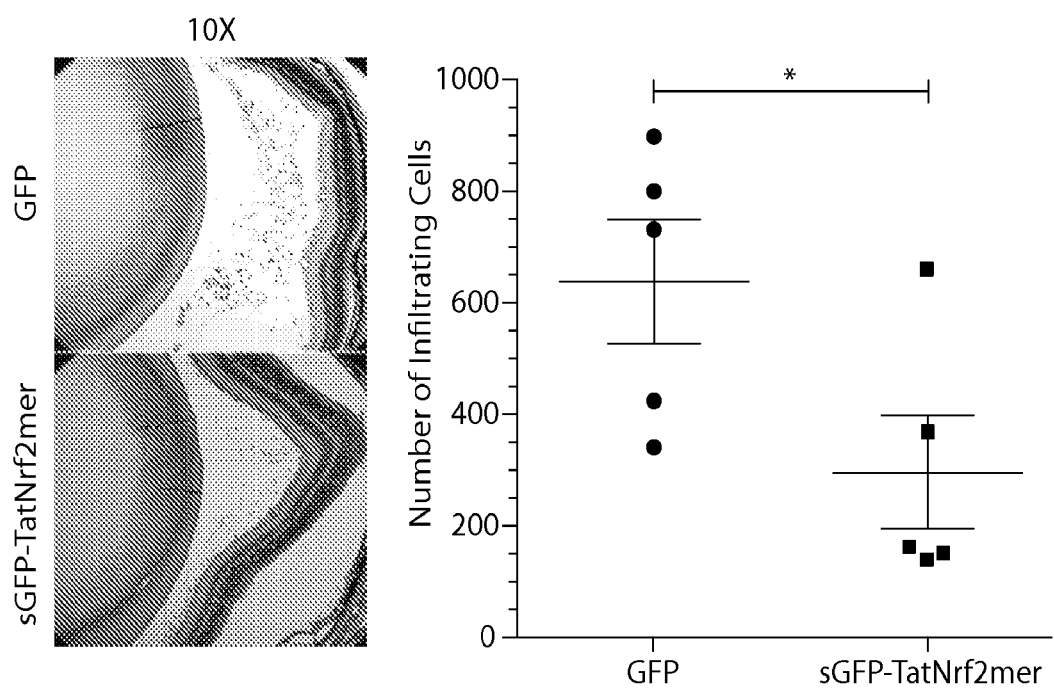

Current research on the etiology of dry-AMD has associated an inflammatory component with the disease. Therefore, the effect of the AAV vector was tested in modulating pro-inflammatory signals such as the cytokine IL-1β. When the stable ARPE-19 cells expressing either puroR or TatNrf2mer-puroR were challenged with 4-HNE, it was observed that cells expressing the TatNrf2mer peptide did not secreted significant amounts of IL-1β into their media when compared with control cells expressing only puroR resistance (FIG. 25A). This result indicates that the TatNrf2mer vector has anti-inflammatory properties as well as antioxidant properties. To test this hypothesis the endotoxin induced uveitis (EIU) mouse model (27) was used. Briefly, C57B/6J mice were injected intravitreally with AAV vectors delivering either GFP or sGFP-TatNrf2mer in the contralateral eye. Three weeks after the vector injection, gene expression was evaluated by fluorescent fundoscopy (FIG. 25B). Eyes treated with the sGFP-TatNrf2mer AAV vector showed a diffused pattern of GFP expression when compared to eyes treated with the GFP AAV vector, thus suggesting the secretion of the sGFP-TatNrf2mer construct. One week after fundus evaluation, mice were injected intravitreally with 25 ng of lipopolysaccharide (LPS) in both eyes. Mice were euthanized 24 hrs later and their eyes harvested and fixed for histological analysis. When the number of infiltrating cells within the vitreous were quantified by two independent individuals, it was observed that eyes treated with the TatNrf2mer AAV vector showed significantly lower number of cells (FIG. 25C).

These results suggest that the AAV vector delivering the secretable TatNrf2mer gene has anti-inflammatory properties in the eye. The use of the AAV vector to deliver the secreted form of the TatNrf2 peptide adds considerable utility to this approach to therapy, since AAV has can infect many different cell types leading to long-term production of the Nrf2mer. AAV vectors have a safety record documented in many pre-clinical and clinical trials. In non-dividing cells, such as those lining the interior surface of the eye, AAV-mediated therapy could be presumed to be life-long.

Materials and Methods

Cell Culture

The HEK293T cell line was grown in DMEM media supplemented with 10% fetal bovine serum (FBS) and 1% penicillin-streptomycin (Pen-Strep) solution. The ARPE-19 cell line was grown in DMEM/F12 (50/50) media supplemented with 10% FBS and 1% Pen-Strep. All the cell cultures were maintained in an incubator at 37° C. with 5% CO2. All stable cell lines generated by lentiviral vector transduction were grown in the corresponding media supplemented with puromycin at a dose of 1 μg/mL.

Design and Cloning the TatNrf2mer Sequence into the pCDH-EF1-MCS-T2A-puroR Lentiviral Vector Plasmid The Nrf2 sequence that interacts with the Keap-1 protein has been reported to have the following amino acid sequence: LQLDEETGEFLPIQ (SEQ ID NO: 1). This sequence was fused downstream to the HIV Tat-peptide sequence (RKKRRQRRR) (SEQ ID NO: 25) to provide the Nrf2 peptide (Nrf2mer) with cell-penetration properties. The complete amino acid sequence of the TatNrf2mer is as follows: RKKRRQRRRLQLDEETGEFLPIQ (SEQ ID NO: 131). Codons were selected and optimized for expression in mammalian cells using the JCat software. The following DNA oligomers were synthesized:

(1)

(SEQ ID NO: 132)
tatGAATTCgccaccatgaggaagaagaggaggcagag<u>GAGGAGGC
TGCAGCTGGACGAG</u>;

(2)

(SEQ ID NO: 133)
ataGCGGCCGCctggatgggcaggaactcgccggtctc<u>CTCGTCCA
GCTGCAGCCTCCTC</u>

The uppercase and underlined sequence of these oligos represent the complementary sequences which has a Tm of 65° C., while the uppercase and bold sequence represents the EcoRI (1) and NotI (2) restriction sites. These oligos were mixed and the single stranded sequences were filled with by Klenow fragment PCR sequence. A reaction mixture of 5 µg of each oligo, 2 µL of NEB buffer 2 (10×), 1 µL of dNTPs mix (10 mM each), and 6 µL of deionized H2O. The hybridization of the oligos was achieved using the following conditions: Three cycles of 94° C. for 30 seconds, and 60° C. for 30 seconds. The reaction was cool down to 15° C. and 1 µL of Klenow fragment (5 U/µL) was added to the reaction which was incubated at room temperature for 15 minutes. The reaction was stopped by adding 1 µL of 210 mM EDTA and incubating at 72° C. for 20 minutes. This product was purified with the GENELUTE™ PCR clean-up kit (Sigma-Aldrich, St Louis, Mo.). The purified fragment and the pCDH-EF1-MCS-T2A-puroR plasmid (Systems Biosciences, Mountain View, Calif.) were digested with EcoRI and NotI for 2 hours at 37° C. and then purified as done previously. The digested products were ligated using the T4 ligase (New England Biolabs, Ipswich, Mass.) by incubating at room temperature for 2 hours. Ligation reactions were transformed into DH5α (Invitrogen, Grand Island, N.Y.).

Lentiviral Vectors Production

All the lentiviral vectors were created using the pCDH-EF1-MCS-T2A-Puro plasmid (Systems Biosciences, Mountain View Calif.). The transgenes were clones using the EcoRI and the NotI restriction sites in the multiple cloning sites. Plasmids were grown in DH5α cells and sequenced by the Sanger method. To generate viral particles, the plasmids were co-transfected with the pPACKH1 lentivector packaging kit (Systems Biosciences, Mountain View Calif.) into HEK293T cells. The lentiviral vector containing media were harvested at 48 hours after the co-transfection and were centrifuged at 3,000 rpm for 5 minutes at 4° C. These vector containing media were filter using a 0.22 µm syringe filter.

Enzyme Linked Immunosorbent Assay (ELISA)

Medium was harvested from the indicated cultures and 100 µL were used to quantify IL-1β concentration. The ELISA kit for the human IL-1β was purchased from RayBiotech (Norcross, Ga.). The concentration of IL-1β was determined as per manufacturer's protocol.

Immunocytochemistry

Cells were grown in an 8-chamber slide at 2×10$^5$ cells per chamber for 24 hrs. Afterwards, cells were washed once with phosphate buffered saline (PBS) and incubated with 2% PFA in PBS for 15 minutes at room temperature. Cells were washed three times with PBS and then incubated in PBS with 0.1% Triton X-100 (PBST) for 10 minutes at room temperature. Cells were then washed three times as done previously. Cells were blocked by incubating with 1% BSA, 1% Goat Serum in PBS with 0.1% Tween-20 and 22.52 mg/mL glycine for 1 hour. The anti-Nrf2 was diluted to 1 µg/mL in PBST with 1% BSA and added to the cells which were then incubated for 1 hour at room temperature in a humidified chamber. Cells were washed as in previous steps and then incubated with an anti-rabbit antibody conjugated to Cy3 chromophore (1:500 dilution) and DAPI (1:1,000 dilution) diluted in PBST with 1% BSA for 1 hour at room temperature in the dark. Cells were then washed as in the previous step and mounted using Fluoromount-G. Pictures were taken using a fluorescence microscope.

Endotoxin-Induced Uveitis (EIU) Mouse Model

Mice of the C57B/6 strain were injected intravitreally with the 3×10$^9$ vector genomes (vgs) in each eye. One month after the injection GFP expression was observed by fluorescent fundoscopy. The next day mice were injected intravitreally in each eye with 25 ng of LPS. After 24 hours, these mice were sacrificed and their eyes were enucleated and placed in 4% paraformaldehyde at 4° C. overnight. Eyes were embedded in paraffin were sectioned through the cornea-optic nerve axis with a thickness of 12 µm. The sections were collected in independent slides with sections on the same slide having a difference of 96 µm. Slides were stained with hematoxylin and eosin to visualize infiltrating cells. These cells were quantified, in images of the sections, by two independent individual.

Sodium Iodate Mouse Model of RPE Damage

One month old C57BL/6J mice were injected intravitreally with 3×10$^9$ vector genomes of AAV vector delivering either GFP (left eye) or sGFP-TatNrf2mer (right eye). One month later mice were evaluated for gene expression using fluorescent fundoscopy. One week later mice were injected intraperitoneally with 35 mg/Kg of sodium iodate NaIO3. One week afterwards, retina function was evaluated by ERG.

Electroretinography (ERG)

Scotopic ERG analysis was used to measure the loss of rod function using methods previously described (Justilien et al., 2007;Mao et al., 2011). Mice are dark adapted by placing them in a dark room for 24 hours. The day of the assay the mice eyes are dilated with drops of 1% atropine and 10% phenylephrine solutions. Mice are then anesthetized with a solution of ketamine and xylazine. Electrodes are placed over the corneas of an anesthetized mouse, while two reference electrodes are placed in the mouth and tail respectively. While in a dark dome, mice are visually stimulated with dim flashes of light and the voltage changes occurring in their eyes are recorded as a function of time. The value of the a-wave is measured from 0 µV reference to the peak of the negative projected wave, while the b-wave is measured from the 0 µV reference to the peak of the positively projected wave.

Retina Funduscopy

Digital fundus imaging was performed with a Micron III retinal imaging microscope (Phoenix Research Laboratories, Pleasaton, Calif.) to monitor gene expression. Conscious mice had their eyes dilated with 1% atropine and 10% phenylephrine. Mice were then anesthetized with a mixture of ketamine and xylazine in normal saline. To avoid loss of moisture from the ocular surface during the procedure mice received a drop of 2.5% hypermellose ophthalmic demulcent solution (Gonak, AKORN, Lake Forest, Ill.). Bright field fundus image was acquired using the same exposition time. Using the fluorescein filters GFP fluorescence was measured using the same exposure time for all the eyes.

Transfection

Cells were plated at 8×10$^5$ cells per well in a 6-well plate with complete growth media and incubated for 24 hours. The next day complete growth medium was replaced in each well with 2 mL of serum and antibiotics free medium. Plasmid DNA complexes were generated by diluting 4 µg of the corresponding DNA in 100 µL of sterile PBS 1× and 10 µg of a 1 µg/µL of polyethyleneimine (PEI) in 100 µL of PBS 1×. Dilutions were incubated at room temperature for 5 minutes. DNA:PEI complexes were made by mixing the diluted DNA and PEI and incubating them for 20 minutes at room temperature. Complexes were overlaid on the cells drop wise and cells were maintained at 37° C. for 18 hours. The transfection was stopped by removing the complex containing medium and replacing it with 3 mL of complete growth medium. Cells were grown for another 24 hours at 37° C. Afterwards, cells were harvested by trypsinization.

RNA Isolation

Total RNA was isolated from cell cultures using the RNeasy mini kit (QIAGEN, Valencia, Calif.) as per manufacturers' protocol. RNA was quantified by 260 nm absorbance and quality was verified by running an aliquot in a 1% agarose gel.

cDNA Synthesis cDNA was synthesized with the iScript cDNA synthesis kit (Bio-Rad,). Briefly, 1 ng of total RNA (10 μL) was mixed with 4 μL of 5× iScript reaction mix, 5 μL of RNAse free water, and 1 μL of iScript reverse transcriptase. The following temperatures and times were used in the synthesis of the cDNA: 25° C. for 5 minutes, 42° for 30 minutes, and 85° C. for 5 minutes. cDNA was stored at −20° C. until needed.

Polymerase Chain Reaction (PCR) for the Detection of TatNrf2mer Expression

A PCR reaction was prepared using 1 uL of cDNA library made from total RNA isolated from wild type ARPE-19 cells or ARPE-19 cells expressing either puromycin resistance (puroR) gene only (control) or TatNrf2mer and the Taq polymerase using the 2× Taq Master Mix. The following primers binding to either the Tat region sequence or the puroR were used:

```
Tat-F:
(SEQ ID NO: 130) (SEQ ID NO: 134)
AGT TCT TGC AGC TCG GTG
(Tm 55° C.)

PuroR-R:
(SEQ ID NO: 131) (SEQ ID NO: 135)
TCG CCA CCA TGA GGA AG
(Tm 56° C.)
```

To amplify the desired sequence the following thermal conditions were used: 93° C. for 3 minutes, 30 cycles of 93° C. for 30 seconds, 55° C. for 30 seconds, and 72° C. for 20 seconds, followed by 72° C. for 10 minutes. PCR products were separated in a 1.3% agarose gel.

Real-Time PCR (RT-PCR) for ARE Genes

The RT-PCR for both GSTM1 and NqO1 was performed using the SSOFAST™ EVAGREEN® Supermix kit (Bio-Rad, Hercules Calif.). The following primers were used to detect the corresponding gene:

```
NqO1-F:
                                    (SEQ ID NO: 136)
AAAGGACCCTTCCGGAGTAA

NqO1-R:
                                    (SEQ ID NO: 137)
CCATCCTTCCAGGATTTGAA

GSTM1-F:
                                    (SEQ ID NO: 138)
CTACCTTGCCCGAAAGCAC

GSTM1-R:
                                    (SEQ ID NO: 139)
ATGTCTGCACGGATCCTCTC
```

```
GAPDH-F:
                                    (SEQ ID NO: 140)
ACAGTCCATGCCATCACTGCC

GAPDH-R:
                                    (SEQ ID NO: 141)
GCCTGCTTCACCACCTTCTTG

β-actin-F:
                                    (SEQ ID NO: 142)
AGCGAGCATCCCCCAAAGTT β-actin-R:
                                    (SEQ ID NO: 143)
GGGCACGAAGGCTCATCATT
```

PCR reaction mixtures for each gene to be measured was prepared by adding 1 μL of a 1:10 dilution of cDNA library, 1 μL of F primer (5 μM) and 1 μL of R primer (5 μM), 5 μL of the 2× supermix, and 2 μL of dH2O. Simultaneous amplification of all genes was done using the following conditions: 95° C. for 3 minutes, followed by 40 cycles of 95° C. for 10 seconds and 60° C. for 20 seconds. Fluorescence was measured at the end of each cycle by using the Bio-Rad CFX96 thermocycler. Fold changes in gene expression were determined by the ΔΔCt method.

MTT Assay

Cell were plated in a 96-well plate at $8 \times 10^4$ cells per well in 100 μL of complete growth media and were incubated overnight at 37° C. The next day, media was removed and cells were washed once with 100 μL of PBS 1×. Cells were then exposed to 200 μL of serum and antibiotic free medium containing 800 μM of $H_2O_2$. The cells were then incubated at 37° C. for six hours. After this incubation, cells were washed once with PBS 1× as done previously. Cells were then incubated with 200 μL of MTT (tetrazolium) solution diluted in RPMI-1640 (500 μg/mL) at 37° C. for 4 hours. As a blank 3 wells with no cells but containing 200 μL of MTT were included in the plate. After the 4 hours, the MTT solution was carefully removed and 200 μL of DMSO was added to the wells. The plate was incubated at room temperature for 15 minutes. The absorbance at 570 nm was determined using a plate reader.

REFERENCES

1. De Jong PTVM (2006) Age-related macular degeneration. N Engl J Med 355(14):1474-1485.
2. Dunavoelgyi R, et al. (2012) Retreatment with antivascular endothelial growth factor therapy based on changes in visual acuity after initial stabilization of neovascular age-related macular degeneration: 3-year follow-up results. Retina Phila Pa 32(8):1471-1479.
3. Eichler W, Yafai Y, Wiedemann P, Fengler D (2006) Antineovascular agents in the treatment of eye diseases. Curr Pharm Des 12(21):2645-2660.
4. El-Mollayess G M, Noureddine B N, Bashshur Z F (2011) Bevacizumab and neovascular age related macular degeneration: pathogenesis and treatment. Semin Ophthalmol 26(3):69-76.
5. Hollyfield J G, et al. (2008) Oxidative damage-induced inflammation initiates age-related macular degeneration. Nat Med 14(2):194-198.
6. Stachel I, et al. (2014) Modulation of Nuclear Factor E2-related Factor-2 (Nrf2) Activation by the Stress Response Gene Immediate Early Response-3 (IER3) in Colonic Epithelial Cells A NOVEL MECHANISM OF CELLULAR ADAPTION TO INFLAMMATORY STRESS. J Biol Chem 289(4):1917-1929.
7. Zhou R, Lin J, Wu D (2014) Sulforaphane induces Nrf2 and protects against CYP2E1-dependent binge alcohol-induced liver steatosis. Biochim Biophys Acta BBA—Gen Subj 1840(1):209-218.
8. Zhao X-D, Zhou Y-T, Lu X-J (2013) Sulforaphane enhances the activity of the Nrf2-ARE pathway and attenuates inflammation in OxyHb-induced rat vascular smooth muscle cells. Inflamm Res 62(9):857-863.
9. Ping Z, et al. (2010) Sulforaphane protects brains against hypoxic-ischemic injury through induction of Nrf2-dependent phase 2 enzyme. Brain Res 1343:178-185.
10. Kubota S, et al. (2009) Prevention of ocular inflammation in endotoxin-induced uveitis with resveratrol by inhibiting oxidative damage and nuclear factor-kappaB activation. Invest OphthalmolVisSci 50(1552-5783 (Electronic)):3512-3519.
11. Ren J, Fan C, Chen N, Huang J, Yang Q (2011) Resveratrol Pretreatment Attenuates Cerebral Ischemic Injury by Upregulating Expression of Transcription Factor Nrf2 and HO-1 in Rats. Neurochem Res 36(12):2352-2362.
12. He X, Wang L, Szklarz G, Bi Y, Ma Q (2012) Resveratrol Inhibits Paraquat-Induced Oxidative Stress and Fibrogenic Response by Activating the Nuclear Factor Erythroid 2-Related Factor 2 Pathway. J Pharmacol Exp Ther 342(1):81-90.
13. Devi T S, et al. (2012) TXNIP Links Innate Host Defense Mechanisms to Oxidative Stress and Inflammation in Retinal Muller Glia under Chronic Hyperglycemia: Implications for Diabetic Retinopathy. J Diabetes Res 2012: e438238.
14. Zhou R, Tardivel A, Thorens B, Choi I, Tschopp J (2010) Thioredoxin-interacting protein links oxidative stress to inflammasome activation. Nat Immunol 11(2):136-140.
15. Cao S, Walker G B, Wang X, Cui J Z, Matsubara J A (2013) Altered cytokine profiles of human retinal pigment epithelium: oxidant injury and replicative senescence. Mol Vis 19:718-728.
16. Liu R T, et al. (2013) Inflammatory Mediators Induced by Amyloid-Beta in the Retina and RPE In Vivo: Implications for Inflammasome Activation in Age-Related Macular Degeneration. Invest Ophthalmol Vis Sci 54(3): 2225-2237.
17. Tarallo V, et al. (2012) DICER1 Loss and Alu RNA Induce Age-Related Macular Degeneration via the NLRP3 Inflammasome and MyD88. Cell 149(4):847-859.
18. Kaneko H, et al. (2011) DICER1 deficit induces Alu RNA toxicity in age-related macular degeneration. Nature 471(7338):325-330.
19. Kauppinen A, et al. (2012) Oxidative stress activates NLRP3 inflammasomes in ARPE-19 cells—implications for age-related macular degeneration (AMD). Immunol Lett 147(1-2):29-33.
20. Crabb J W, et al. (2002) Drusen proteome analysis: An approach to the etiology of age-related macular degeneration. Proc Natl Acad Sci 99(23):14682-14687.
21. Doyle S L, et al. (2012) NLRP3 has a protective role in age-related macular degeneration through the induction of IL-18 by drusen components. Nat Med 18(5):791-798.
22. Cruz-Guilloty F, et al. (2014) T Cells and Macrophages Responding to Oxidative Damage Cooperate in Pathogenesis of a Mouse Model of Age-Related Macular Degeneration. PLoS ONE 9(2):e88201.
23. Demircan N, Safran B G, Soylu M, Ozcan A A, Sizmaz S (2006) Determination of vitreous interleukin-1 (IL-1) and tumour necrosis factor (TNF) levels in proliferative diabetic retinopathy. Eye Lond Engl 20(12):1366-1369.
24. Zhou J, Wang S, Xia X (2012) Role of intravitreal inflammatory cytokines and angiogenic factors in proliferative diabetic retinopathy. Curr Eye Res 37(5):416-420.
25. Steel R, Cowan J, Payerne E, O'Connell M A, Searcey M (2012) Anti-inflammatory Effect of a Cell-Penetrating Peptide Targeting the Nrf2/Keap1 Interaction. ACS Med Chem Lett 3(5):407-410.
26. Enzmann V, et al. (2006) Behavioral and anatomical abnormalities in a sodium iodate-induced model of retinal pigment epithelium degeneration. Exp Eye Res 82(3): 441-448.
27. Yadav U C, Ramana K V (2013) Endotoxin-induced uveitis in rodents. Methods MolBiol 1031(1940-6029 (Electronic)):155-162.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. An AAV vector comprising an expression construct comprising a nucleotide sequence encoding a recombinant polypeptide,
   wherein the recombinant polypeptide comprises a cell penetrating peptide comprising a Tat peptide, an Nrf2 peptide consisting of a 14-mer peptide having the amino acid sequence LQLDEETGEFLPIQ (SEQ ID NO: 1), and a secretion signal, and
   wherein the AAV vector is encapsidated in a viral particle comprising a modified AAV2 capsid protein having non-tyrosine residues corresponding to the positions Y272, Y444, Y500, and Y730 of a wild-type AAV2 capsid.

2. The AAV vector of claim 1, wherein the recombinant polypeptide further comprises a carrier protein.

3. The AAV vector of claim 2, wherein the secretion signal comprises a sequence selected from SEQ ID NOs: 2-14, the cell penetrating peptide comprises a sequence comprising SEQ ID NO: 25, and the carrier protein is selected from opticin, human serum albumin, dihidrofolate reductase (DHFR) destabilization domain, and FK506 binding protein (FKBP) destabilization domain.

4. The AAV vector of claim 2, wherein the carrier protein and cell penetrating peptide are linked to one another by an enzyme cleavage site.

5. The AAV vector of claim 4, wherein the enzyme cleavage site is a furin cleavage site.

6. The AAV vector of claim 3, wherein the secretion signal is an Igκ signal.

7. A composition comprising a pharmaceutically acceptable carrier and the AAV vector of claim 1.

8. A method for the amelioration or treatment of a disease or condition associated with oxidative stress or inflammation in a subject, the method comprising administration of a therapeutically effective amount of the AAV vector of claim 1 to the eye of the subject.

9. The method of claim 8, wherein the recombinant polypeptide of the AAV vector further comprises a carrier protein.

10. The method of claim 9, wherein the secretion signal comprises a sequence selected from SEQ ID NOs: 2-14, the cell penetrating peptide comprises a sequence comprising SEQ ID NO: 25, and the carrier protein is selected from opticin, human serum albumin, dihidrofolate reductase (DHFR) destabilization domain, and FK506 binding protein (FKBP) destabilization domain.

11. The method of claim 9, wherein the carrier protein and cell penetrating peptide are linked to one another by an enzyme cleavage site.

12. The method of claim 11, wherein the enzyme cleavage site is a furin cleavage site.

13. The method of claim 8, wherein said administration results in secretion of the recombinant polypeptide from cells transfected with the AAV vector.

* * * * *

SEQUENCE LISTING

<160> NUMBER OF SEQ ID NOS: 143

<210> SEQ ID NO 1
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1

Leu Gln Leu Asp Glu Glu Thr Gly Glu Phe Leu Pro Ile Gln
1               5                   10

<210> SEQ ID NO 2
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 3

Met Ala Ala Pro Val Pro Trp Ala Cys Cys Ala Val Leu Ala Ala Ala
1               5                   10                  15

Ala Ala Val Val Tyr Ala
            20

<210> SEQ ID NO 4
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 4

Met Gln Ala Leu Val Leu Leu Leu Cys Ile Gly Ala Leu Leu Gly His
1               5                   10                  15

Ser Ser Cys

<210> SEQ ID NO 5
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 5

Met Trp Lys Trp Ile Leu Thr His Cys Ala Ser Ala Phe Pro His Leu
1               5                   10                  15

Pro Gly Cys Cys Cys Cys Cys Phe Leu Leu Leu Phe Leu Val Ser Ser
            20                  25                  30

Val Pro Val Thr Cys

<210> SEQ ID NO 6
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 6

Met Arg Thr Leu Ala Cys Leu Leu Leu Gly Cys Gly Tyr Leu Ala
1               5                   10                  15

His Val Leu Ala
            20

<210> SEQ ID NO 7
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 7

Met Ala Pro Ser Leu Ser Pro Gly Pro Ala Ala Leu Arg Arg Ala Pro
1               5                   10                  15

Gln Leu Leu Leu Leu Leu Ala Ala Glu Cys Ala Leu Ala
            20                  25                  30

<210> SEQ ID NO 8
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 8

Met Thr Pro Trp Leu Gly Leu Ile Val Leu Leu Gly Ser Trp Ser Leu
1               5                   10                  15

Gly Asp Trp Gly Ala Glu Ala
            20

<210> SEQ ID NO 9
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 9

Met Asn Phe Leu Leu Ser Trp Val His Trp Ser Leu Ala Leu Leu Leu
1               5                   10                  15

Tyr Leu His His Ala Lys Trp Ser Gln Ala
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 10

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly
            20                  25

<210> SEQ ID NO 11
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 11

Met Arg Leu Leu Ala Lys Ile Ile Cys Leu Met Leu Trp Ala Ile Cys
1               5                   10                  15

Val Ala

<210> SEQ ID NO 12
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 12

Met Thr Ser Lys Leu Ala Val Ala Leu Leu Ala Ala Phe Leu Ile Ser
1               5                   10                  15

Ala Ala Leu Cys
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 13

Met Lys Val Ser Ala Ala Leu Leu Cys Leu Leu Leu Ile Ala Ala Thr
1               5                   10                  15

Phe Ile Pro Gln Gly Leu Ala
            20

<210> SEQ ID NO 14
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 14

Met Lys Leu Trp Asp Val Val Ala Val Cys Leu Val Leu Leu His Thr
1               5                   10                  15

Ala Ser Ala

<210> SEQ ID NO 15
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 15

Arg Lys Lys Arg Arg Arg Glu Ser Arg Lys Lys Arg Arg Arg Glu Ser
1               5                   10                  15

-continued

```
<210> SEQ ID NO 16
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 16

Gly Arg Pro Arg Glu Ser Gly Lys Lys Arg Lys Arg Lys Arg Leu Lys
1               5                   10                  15

Pro

<210> SEQ ID NO 17
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 17

Gly Lys Arg Lys Lys Lys Gly Lys Leu Gly Lys Lys Arg Asp Pro
1               5                   10                  15

<210> SEQ ID NO 18
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 18

Gly Lys Arg Lys Lys Lys Gly Lys Leu Gly Lys Lys Arg Pro Arg Ser
1               5                   10                  15

Arg

<210> SEQ ID NO 19
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 19

Arg Lys Lys Arg Arg Arg Glu Ser Arg Arg Ala Arg Arg Ser Pro Arg
1               5                   10                  15

His Leu

<210> SEQ ID NO 20
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 20

Ser Arg Arg Ala Arg Arg Ser Pro Arg Glu Ser Gly Lys Lys Arg Lys
1               5                   10                  15

Arg Lys Arg

<210> SEQ ID NO 21
<211> LENGTH: 19
<212> TYPE: PRT
<213> ORGANISM: Artificial Sequence
<220> FEATURE:
<223> OTHER INFORMATION: Synthetic Polypeptide
```

```
<400> SEQUENCE: 21

Val Lys Arg Gly Leu Lys Leu Arg His Val Arg Pro Arg Val Thr Arg
1               5                   10                  15

Met Asp Val

<210> SEQ ID NO 22
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 22

Ser Arg Arg Ala Arg Arg Ser Pro Arg His Leu Gly Ser Gly
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 23

Leu Arg Arg Glu Arg Gln Ser Arg Leu Arg Arg Glu Arg Gln Ser Arg
1               5                   10                  15

<210> SEQ ID NO 24
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 24

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 25
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 25

Arg Lys Lys Arg Arg Gln Arg Arg Arg
1               5

<210> SEQ ID NO 26
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 26

Arg Arg Arg Arg Asn Arg Thr Arg Arg Asn Arg Arg Arg Val Arg
1               5                   10                  15

<210> SEQ ID NO 27
<211> LENGTH: 17
```

```
<212> TYPE: PRT
<213> ORGANISM: Artificial Sequence
<220> FEATURE:
<223> OTHER INFORMATION: Synthetic Polypeptide

<400> SEQUENCE: 27

Thr Arg Gln Ala Arg Arg Asn Arg Arg Arg Trp Arg Glu Arg Gln
1               5                   10                  15

Arg

<210> SEQ ID NO 28
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 28

Thr Arg Arg Gln Arg Thr Arg Arg Ala Arg Arg Asn Arg
1               5                   10

<210> SEQ ID NO 29
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 29

Lys Met Thr Arg Ala Gln Arg Arg Ala Ala Arg Arg Asn Arg Trp
1               5                   10                  15

Thr Ala Arg

<210> SEQ ID NO 30
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 30

Asn Ala Lys Thr Arg Arg His Glu Arg Arg Lys Leu Ala Ile Glu
1               5                   10                  15

Arg

<210> SEQ ID NO 31
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 31

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 32
<211> LENGTH: 18
<212> TYPE: PRT
<213> ORGANISM: Artificial Sequence
<220> FEATURE:
<223> OTHER INFORMATION: Synthetic Polypeptide
```

```
<400> SEQUENCE: 32

Thr Ala Lys Thr Arg Tyr Lys Ala Arg Arg Ala Glu Leu Ile Ala Glu
1               5                   10                  15

Arg Arg

<210> SEQ ID NO 33
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 33

Thr Arg Arg Asn Lys Arg Asn Arg Ile Gln Glu Gln Leu Asn Arg Lys
1               5                   10                  15

<210> SEQ ID NO 34
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 34

Pro Arg Arg Arg Arg Ser Ser Ser Arg Pro Val Arg Arg Arg Arg Arg
1               5                   10                  15

Pro Arg Val Ser Arg Arg Arg Arg Arg Gly Gly Arg Arg Arg Arg
            20                  25                  30

<210> SEQ ID NO 35
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 35

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 36

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 37
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 37

Lys Arg Ala Arg Asn Thr Glu Ala Ala Arg Arg Ser Arg Ala Arg Lys
```

```
                1               5                  10                  15
Leu Gln Arg Met Lys Gln
                20

<210> SEQ ID NO 38
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 38

Arg Gln Ile Lys Ile Trp Phe Gln Asn Arg Arg Met Lys Trp Lys Lys
1               5                  10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 39

Arg Val Ile Arg Val Trp Phe Gln Asn Lys Arg Cys Lys Asp Lys Lys
1               5                  10                  15

<210> SEQ ID NO 40
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 40

Ser Lys Arg Thr Arg Gln Thr Tyr Thr Arg Tyr Gln Thr Leu Glu Leu
1               5                  10                  15

Glu Lys Glu Phe His Phe Asn Arg Tyr Ile Thr Arg Arg Arg Ile
            20                  25                  30

Asp Ile Ala Asn Ala Leu Ser Leu Ser Glu Arg Gln Ile Lys Ile Trp
        35                  40                  45

Phe Gln Asn Arg Arg Met Lys Ser Lys Lys Asp Arg
    50                  55                  60

<210> SEQ ID NO 41
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 41

Ser Gln Ile Lys Ile Trp Phe Gln Asn Lys Arg Ala Lys Ile Lys Lys
1               5                  10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 42

Arg Gln Val Thr Ile Trp Phe Gln Asn Arg Arg Val Lys Glu Lys Lys
1               5                  10                  15
```

```
<210> SEQ ID NO 43
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 43

Lys Gln Ile Asn Asn Trp Phe Ile Asn Gln Arg Lys Arg His Trp Lys
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 44

Arg His Ile Lys Ile Trp Phe Gln Asn Arg Arg Met Lys Trp Lys Lys
1               5                   10                  15

<210> SEQ ID NO 45
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 45

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 46
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 46

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 47
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 47

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 48
<211> LENGTH: 21
<212> TYPE: PRT
<213> ORGANISM: Artificial Sequence
```

```
<220> FEATURE:
<223> OTHER INFORMATION: Synthetic Polypeptide

<400> SEQUENCE: 48

Ala Ala Val Leu Leu Pro Val Leu Leu Ala Ala Pro Val Gln Arg Lys
1               5                   10                  15
Arg Gln Lys Leu Pro
            20

<210> SEQ ID NO 49
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 49

Ala Ala Val Leu Leu Pro Val Leu Leu Ala Ala Pro
1               5                   10

<210> SEQ ID NO 50
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 50

Arg Arg Ile Arg Pro Arg Pro Pro Arg Leu Pro Arg Pro Arg Pro Arg
1               5                   10                  15
Pro Leu Pro Phe Pro Arg Pro Gly
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 51

Val Asp Lys Gly Ser Tyr Leu Pro Arg Pro Thr Pro Pro Arg Pro Ile
1               5                   10                  15
Tyr Asn Arg Asn
            20

<210> SEQ ID NO 52
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 52

Lys Cys Phe Gln Trp Gln Arg Asn Met Arg Lys Val Arg Gly Pro Pro
1               5                   10                  15
Val Ser Cys Ile Lys Arg
            20

<210> SEQ ID NO 53
<211> LENGTH: 21
<212> TYPE: PRT
<213> ORGANISM: Artificial Sequence
<220> FEATURE:
<223> OTHER INFORMATION: Synthetic Polypeptide
```

```
<400> SEQUENCE: 53

Thr Arg Ser Ser Arg Ala Gly Leu Gln Trp Pro Val Gly Arg Val His
1               5                   10                  15

Arg Leu Leu Arg Lys
            20

<210> SEQ ID NO 54
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 54

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 55
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 55

Gly Ile Gly Lys Trp Leu His Ser Ala Lys Lys Phe Gly Lys Ala Phe
1               5                   10                  15

Val Gly Glu Ile Met Asn Ser
            20

<210> SEQ ID NO 56
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 56

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
        35

<210> SEQ ID NO 57
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 57

Arg Gly Gly Arg Leu Ser Tyr Ser Arg Arg Arg Phe Ser Thr Ser Thr
1               5                   10                  15

Gly Arg

<210> SEQ ID NO 58
<211> LENGTH: 14
<212> TYPE: PRT
```

```
<213> ORGANISM: Artificial Sequence
<220> FEATURE:
<223> OTHER INFORMATION: Synthetic Polypeptide

<400> SEQUENCE: 58

Tyr Lys Gln Cys His Lys Lys Gly Gly Lys Lys Gly Ser Gly
1               5                   10

<210> SEQ ID NO 59
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 59

Ala Leu Trp Lys Thr Leu Leu Lys Lys Val Leu Lys Ala Pro Lys Lys
1               5                   10                  15

Lys Arg Lys Val
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 60

His Ala Arg Ile Lys Pro Thr Phe Arg Arg Leu Lys Trp Lys Tyr Lys
1               5                   10                  15

Gly Lys Phe Trp
            20

<210> SEQ ID NO 61
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 61

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 62
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 62

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25

<210> SEQ ID NO 63
<211> LENGTH: 34
<212> TYPE: PRT
<213> ORGANISM: Artificial Sequence
<220> FEATURE:
```

<223> OTHER INFORMATION: Synthetic Polypeptide

<400> SEQUENCE: 63

Asn Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 64
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 64

Arg His Ser Arg Ile Gly Ile Ile Gln Gln Arg Arg Thr Arg Asn Gly
1               5                   10                  15

<210> SEQ ID NO 65
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 65

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 66
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 66

Pro Leu Ser Ser Ile Phe Ser Arg Ile Gly Asp Pro
1               5                   10

<210> SEQ ID NO 67
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 67

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 68
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 68

```
Arg Arg Ile Pro Asn Arg Arg Pro Arg Arg
1               5                   10
```

<210> SEQ ID NO 69
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 69

```
Arg Leu Arg Trp Arg
1               5
```

<210> SEQ ID NO 70
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 70

```
Met Val Arg Arg Phe Leu Val Thr Leu Arg Ile Arg Arg Ala Cys Gly
1               5                   10                  15

Pro Pro Arg Val Arg Val
            20
```

<210> SEQ ID NO 71
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 71

```
Met Val Thr Val Leu Phe Arg Arg Leu Arg Ile Arg Arg Ala Cys Gly
1               5                   10                  15

Pro Pro Arg Val Arg Val
            20
```

<210> SEQ ID NO 72
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 72

```
Leu Leu Ile Ile Leu Arg Arg Arg Ile Arg Lys Gln Ala His Ala His
1               5                   10                  15

Ser Lys
```

<210> SEQ ID NO 73
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 73

```
Leu Ser Thr Ala Ala Asp Met Gln Gly Val Val Thr Asp Gly Met Ala
1               5                   10                  15

Ser Gly
```

```
<210> SEQ ID NO 74
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 74

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 75
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 75

Lys Phe His Thr Phe Pro Gln Thr Ala Ile Gly Val Gly Ala Pro
1               5                   10                  15

<210> SEQ ID NO 76
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 76

Val Pro Thr Leu Lys
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 77

Pro Met Leu Lys Glu
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 78

Val Pro Ala Leu Arg
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 79

Val Ser Ala Leu Lys
```

```
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 80

Ile Pro Ala Leu Lys
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 81

Pro Phe Val Tyr Leu Ile
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 82

Pro Ile Glu Val Cys Met Tyr Arg Glu Pro
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 83

Arg Arg Arg Arg Arg Arg Arg Arg
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 84

Arg Arg Arg Arg Arg Arg Arg Arg Arg
1               5

<210> SEQ ID NO 85
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 85

Arg Arg Arg Arg Arg Arg Arg Arg Arg Arg
1               5                   10
```

<210> SEQ ID NO 86
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 86

Arg Arg Arg Arg Arg Arg Arg Arg Arg Arg Arg Arg
1               5                   10

<210> SEQ ID NO 87
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 87

Lys Glu Thr Trp Trp Glu Thr Trp Trp Thr Glu Trp Ser Gln Pro Lys
1               5                   10                  15

Lys Arg Lys Val
            20

<210> SEQ ID NO 88
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 88

Gly Leu Ala Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 89
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 89

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 90
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 90

Ala Gly Tyr Leu Leu Gly His Ile Asn Leu His His Leu Ala His Leu
1               5                   10                  15

Ala Ile Asx His His Ile Leu
            20

```
<210> SEQ ID NO 91
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 91

Lys Leu Ala Leu Lys Ala Leu Lys Ala Leu Lys Ala Ala Leu Lys Leu
1               5                   10                  15

Ala

<210> SEQ ID NO 92
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 92

Arg Arg Trp Trp Arg Arg Trp Arg Arg
1               5

<210> SEQ ID NO 93
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 93

Gly Leu Trp Arg Ala Leu Trp Arg Leu Leu Arg Ser Leu Trp Arg Leu
1               5                   10                  15

Leu Trp Arg Ala
            20

<210> SEQ ID NO 94
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 94

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 95
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 95

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 96
<211> LENGTH: 18
<212> TYPE: PRT
```

```
<213> ORGANISM: Artificial Sequence
<220> FEATURE:
<223> OTHER INFORMATION: Synthetic Polypeptide

<400> SEQUENCE: 96

Leu Lys Thr Leu Thr Glu Thr Leu Lys Glu Leu Thr Lys Thr Leu Thr
1               5                   10                  15

Glu Leu

<210> SEQ ID NO 97
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 97

Gln Leu Ala Leu Gln Leu Ala Leu Gln Ala Leu Gln Ala Ala Leu Gln
1               5                   10                  15

Leu Ala

<210> SEQ ID NO 98
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 98

Pro Pro Arg Pro Pro Arg Pro Pro Arg
1               5

<210> SEQ ID NO 99
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 99

Pro Pro Arg Pro Pro Arg Pro Pro Arg Pro Pro Arg
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 100

Pro Pro Arg Pro Pro Arg Pro Pro Arg Pro Pro Arg Pro Pro Arg
1               5                   10                  15

<210> SEQ ID NO 101
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 101

Pro Pro Arg Pro Pro Arg Pro Pro Arg Pro Pro Arg Pro Pro Arg Pro
1               5                   10                  15

Pro Arg
```

<210> SEQ ID NO 102
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 102

Pro Arg Arg Pro Arg Arg Pro Arg Arg
1               5

<210> SEQ ID NO 103
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 103

Pro Arg Arg Pro Arg Arg Pro Arg Arg Pro Arg Arg
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 104

Pro Arg Arg Pro Arg Arg Pro Arg Arg Pro Arg Arg Pro Arg Arg
1               5                   10                  15

<210> SEQ ID NO 105
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 105

Pro Arg Arg Pro Arg Arg Pro Arg Arg Pro Arg Arg Pro Arg Arg Pro
1               5                   10                  15

Arg Arg

<210> SEQ ID NO 106
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 106

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Asn Val Val Thr
            20                  25                  30

Arg His Arg Tyr
        35

<210> SEQ ID NO 107
<211> LENGTH: 36
<212> TYPE: PRT
<213> ORGANISM: Artificial Sequence

```
<220> FEATURE:
<223> OTHER INFORMATION: Synthetic Polypeptide

<400> SEQUENCE: 107

Gly Pro Ser Gln Pro Thr Tyr Pro Gly Asp Asp Ala Pro Val Arg Asp
1               5                   10                  15

Leu Ile Arg Phe Tyr Arg Asp Leu Arg Arg Tyr Leu Asn Val Val Thr
            20                  25                  30

Arg His Arg Tyr
        35

<210> SEQ ID NO 108
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 108

Gly Pro Ser Gln Pro Thr Tyr Pro Gly Asp Asp Ala Pro Val Arg Asp
1               5                   10                  15

Leu Arg Arg Phe Tyr Arg Asp Leu Arg Arg Tyr Leu Asn Val Val Thr
            20                  25                  30

Arg His Arg Tyr
        35

<210> SEQ ID NO 109
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 109

Gly Pro Leu Xaa Xaa Asn Pro Leu
1               5

<210> SEQ ID NO 110
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 110

Val Arg Leu Pro Pro Pro Val Arg Leu Pro Pro Pro Val Arg Leu Pro
1               5                   10                  15

Pro Pro

<210> SEQ ID NO 111
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 111

Val Glu Leu Pro Pro Pro Val Glu Leu Pro Pro Pro Val Glu Leu Pro
1               5                   10                  15

Pro Pro
```

<210> SEQ ID NO 112
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 112

Phe Lys Ile Tyr Asp Lys Lys Val Arg Thr Arg Val Val Lys His
1               5                   10                  15

<210> SEQ ID NO 113
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 113

Arg Ala Ser Lys Arg Asp Gly Ser Trp Val Lys Lys Leu His Arg Ile
1               5                   10                  15

Leu Glu

<210> SEQ ID NO 114
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 114

Lys Gly Thr Tyr Lys Lys Lys Leu Met Arg Ile Pro Leu Lys Gly Thr
1               5                   10                  15

<210> SEQ ID NO 115
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 115

Leu Tyr Lys Lys Gly Pro Ala Lys Lys Gly Arg Pro Pro Leu Arg Gly
1               5                   10                  15

Trp Phe His

<210> SEQ ID NO 116
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 116

His Ser Pro Ile Ile Pro Leu Gly Thr Arg Phe Val Cys His Gly Val
1               5                   10                  15

Thr

<210> SEQ ID NO 117
<211> LENGTH: 16
<212> TYPE: PRT
<213> ORGANISM: Artificial Sequence
<220> FEATURE:
<223> OTHER INFORMATION: Synthetic Polypeptide

```
<400> SEQUENCE: 117

Tyr Thr Ala Ile Ala Trp Val Lys Ala Phe Ile Arg Lys Leu Arg Lys
1               5                   10                  15

<210> SEQ ID NO 118
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 118

Ile Ala Trp Val Lys Ala Phe Ile Arg Lys Leu Arg Lys Gly Pro Leu
1               5                   10                  15

Gly

<210> SEQ ID NO 119
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 119

Arg Leu Ser Gly Met Asn Glu Val Leu Ser Phe Arg Trp Leu
1               5                   10

<210> SEQ ID NO 120
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 120

Ser Asp Leu Trp Glu Met Met Met Val Ser Leu Ala Cys Gln Tyr
1               5                   10                  15

<210> SEQ ID NO 121
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 121

Val Thr Trp Thr Pro Gln Ala Trp Phe Gln Trp Val
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 122

Gly Ser Pro Trp Gly Leu Gln His His Pro Pro Arg Thr
1               5                   10

<210> SEQ ID NO 123
<211> LENGTH: 13
<212> TYPE: PRT
<213> ORGANISM: Artificial Sequence
<220> FEATURE:
```

<223> OTHER INFORMATION: Synthetic Polypeptide

<400> SEQUENCE: 123

Gly Pro Phe His Phe Tyr Gln Phe Leu Phe Pro Val
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 124

Thr Ser Pro Leu Asn Ile His Asn Gly Gln Lys Leu
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 125

Cys Ala Tyr His Arg Leu Arg Arg Cys
1               5

<210> SEQ ID NO 126
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 126

Arg Cys Gly Arg Ala Ser Arg Cys Arg Val Arg Trp Met Arg Arg
1               5                   10                  15

Arg Ile

<210> SEQ ID NO 127
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 127

Pro Tyr Ser Arg Pro His Val Gln Leu Trp Tyr Pro Asn Arg Glu Ser
1               5                   10                  15

Cys Arg Ser Leu Ile Arg Ser Leu Gly Pro
            20                  25

<210> SEQ ID NO 128
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 128

Pro Leu Ile Leu Leu Arg Leu Leu Arg Gly Gln Phe
1               5                   10

<210> SEQ ID NO 129

```
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 129

Pro Leu Ile Tyr Leu Arg Leu Leu Arg Gly Gln Phe
1               5                   10

<210> SEQ ID NO 130
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 130

Lys Leu Trp Met Arg Trp Tyr Ser Pro Thr Thr Arg Arg Tyr Gly
1               5                   10                  15

<210> SEQ ID NO 131
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 131

Arg Lys Lys Arg Arg Gln Arg Arg Arg Leu Gln Leu Asp Glu Glu Thr
1               5                   10                  15

Gly Glu Phe Leu Pro Ile Gln
            20

<210> SEQ ID NO 132
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 132
tatgaattcg ccaccatgag gaagaagagg aggcagagga ggaggctgca gctggacgag      60

<210> SEQ ID NO 133
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 133
atagcggccg cctggatggg caggaactcg ccggtctcct cgtccagctg cagcctcctc      60

<210> SEQ ID NO 134
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 134
agttcttgca gctcggtg                                                    18

<210> SEQ ID NO 135
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 135
tcgccaccat gaggaag                                                      17

<210> SEQ ID NO 136
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 136
aaaggaccct tccggagtaa                                                   20

<210> SEQ ID NO 137
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 137
ccatccttcc aggatttgaa                                                   20

<210> SEQ ID NO 138
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 138
ctaccttgcc cgaaagcac                                                    19

<210> SEQ ID NO 139
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 139
atgtctgcac ggatcctctc                                                   20

<210> SEQ ID NO 140
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 140
acagtccatg ccatcactgc c                                                 21

<210> SEQ ID NO 141
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 141
```

```
gcctgcttca ccaccttctt g                                                    21

<210> SEQ ID NO 142
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 142
agcgagcatc ccccaaagtt                                                      20

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
gggcacgaag gctcatcatt                                                      20
```